US008841423B2

(12) United States Patent
Anderson et al.

(10) Patent No.: US 8,841,423 B2
(45) Date of Patent: Sep. 23, 2014

(54) MONOCLONAL ANTIBODIES SPECIFIC FOR OXIDIZED CALCIUM/CALMODULIN DEPENDENT PROTEIN KINASE II

(75) Inventors: Mark E. Anderson, Iowa City, IA (US); Peter J. Mohler, Iowa City, IA (US); Douglas R. Spitz, Jr., Iowa City, IA (US); Jeffrey Robert Erickson, Davis, CA (US)

(73) Assignee: University of Iowa Research Foundation, Iowa City, IA (US)

( * ) Notice: Subject to any disclaimer, the term of this patent is extended or adjusted under 35 U.S.C. 154(b) by 689 days.

(21) Appl. No.: 12/430,644

(22) Filed: Apr. 27, 2009

(65) Prior Publication Data

US 2010/0226929 A1 Sep. 9, 2010

Related U.S. Application Data

(60) Provisional application No. 61/048,259, filed on Apr. 28, 2008.

(51) Int. Cl.
| | |
|---|---|
| C07K 16/44 | (2006.01) |
| A61K 39/395 | (2006.01) |
| G01N 33/574 | (2006.01) |
| C07K 16/40 | (2006.01) |

(52) U.S. Cl.
CPC ............ *C07K 16/40* (2013.01); *C07K 16/44* (2013.01); *G01N 2800/2821* (2013.01); *G01N 2800/32* (2013.01); *G01N 33/57484* (2013.01); *G01N 2800/26* (2013.01)
USPC ............ 530/388.26; 530/389.8; 530/387.9

(58) Field of Classification Search
None
See application file for complete search history.

(56) References Cited

U.S. PATENT DOCUMENTS

| | | | | |
|---|---|---|---|---|
| 6,716,604 | B2* | 4/2004 | Shao et al. | 435/69.2 |
| 2003/0134777 | A1 | 7/2003 | Anderson et al. | |
| 2004/0266675 | A1 | 12/2004 | Anderson | |
| 2009/0011989 | A1 | 1/2009 | Anderson et al. | |

OTHER PUBLICATIONS

Campbell (Monoclonal Antibody Technology, 1984, Chapter 1, pp. 1-32).*
Backs et al., "CaM kinase II selectively signals to histone deacetylase 4 during cardiomyocyte hypertrophy", Journal of Clinical Investigation, Jul. 2006, pp. 1853-1864, vol. 116, No. 7.
Colbran, "Inactivation of Ca2+/Calmodulin-dependent Protein Kinase II by Basal Autophosphorylation", Journal of Biological Chemistry, Apr. 5, 1993, pp. 7163-7170, vol. 268, No. 10.
Cross et al., "Oxidative stress inhibits MEKK1 by site-specific glutathionylation in the ATP-binding domain", Biochemistry Journal, 2004, pp. 675-683, vol. 381.
Doerries et al., "Critical Role of the NAD(P)H Oxidase Subunit p47phox for Left Ventricular Remodeling/Dysfunction and Survival After Myocardial Infarction", Journal of the American Heart Association, 2007, pp. 894-903, vol. 100.
Erickson et al., "A dynamic pathway for calcium-independent activation of CaMKII by Methionine oxidation", National Institute of Health, May 2, 2008, pp. 462-474, vol. 133, No. 3.
Engers et al., "Rac upregulates tissue inhibitor of metalloproteinase-1 expression by redox-dependent activation of extracellular signal-regulated kinase signaling", FEBS Journal, 2006, pp. 4754-4769, vol. 273.
Grueter et al., "L-Type Ca2+ Channel Facilitation Mediated by Phosphorylation of the beta Subunit by CaMKII", Molecular Cell Journal, Sep. 1, 2006, pp. 641-650, vol. 23.
Hammond et al., "An RNA-directed nuclease mediates post-transcriptional gene silencing in *Drosophila* cells", Nature, Mar. 16, 2000, pp. 293-296, vol. 404.
Hare, "Oxidative Stress and Apoptosis in Heart Failure Progression", Journal of the American Heart Association, 2001, pp. 198-200, vol. 89.
Hoshi et al., "Regulation of cell function by methionine oxidation and reduction", Journal of Physiology, 2001, pp. 1-11, vol. 531, No. 1.
Howe et al., "Redox Regulation of the Calcium/Calmodulin-dependent Protein Kinases", Journal of Biological Chemistry, Oct. 22, 2004, pp. 44573-44581, vol. 279, No. 43.
Hudmon et al., "Structure-function of the multifunctional Ca2+/calmodulin-dependent protein kinase II", Biochemistry Journal, 2002, pp. 593-611, vol. 364.
Khoo et al., "Death, Cardiac Dysfunction, and Arrhythmias Are Increased by Calmodulin Kinase II in Calcineurin Cardiomyopathy", Journal of the American Heart Association, 2006, pp. 1352-1359, vol. 114.
Kinugawa et al., "Treatment With Dimethylthiourea Prevents Left ventricular Remodeling and Failure After Experimental Myocardia Infarction in Mice: Role of Oxidative Stress", Journal of the American Heart Association, 2000, pp. 392-398, vol. 87.
Kryukov et al., "Selenoprotein R is a zinc-containing stereo-specific methionine sulfoxide reductase", Biochemistry, Apr. 2, 2002, pp. 4245-4250, vol. 99, No. 7.
Lou et al., "Activation of the multifunctional Ca2+/calmodulin-dependent protein kinase by autophosphorylation: ATP modulates production of an autonomous enzyme", Proceedings of the National Academy of Science, Dec. 1986, pp. 9497-9501, vol. 83.
Lyle et al., "Modulation of Vascular Smooth Muscle Signaling by Reactive Oxygen Species", Physiology Journal, 2005, pp. 269-280, vol. 21.

(Continued)

*Primary Examiner* — Sharon Wen
(74) *Attorney, Agent, or Firm* — Andrus Intellectual Property Law, LLP

(57) ABSTRACT

Calcium/calmodulin dependent protein kinase II (CaMKII) has been found to be directly oxidized, and direct oxidation of CaMKII was observed to result in calcium independent activation of CaMKII. Antibodies that bind specifically to oxidized forms of CaMKII (oxCaMKII) were generated and were utilized to detect oxCaMKII in blood from: (1) mice with cancer; (2) mice with a knock out of the gene encoding methionine sulfoxide reductase; (3) mice injected with angiotensin II; (4) mice injected with bacterial endotoxin; (5) mice fed a pro-oxidant (ketogenic) diet; and (6) mice with cancer that had been treated with experimental therapy.

14 Claims, 32 Drawing Sheets

(56) References Cited

OTHER PUBLICATIONS

Maack et al., "Oxygen Free Radical Release in Human Failing Myocardium is Associated With Increased Activity of Rac1-GTPase and Represents a Target for Statin Treatment", Journal of the American Heart Association, 2003, pp. 1567-1574, vol. 108.

Mohler et al., "Defining the Cellular Phenotype of "Ankyrin-B Syndrome" Variants: Human ANK2 Variants Associated With Clinical Phenotypes Display a spectrum of Activites in Cardiomyocytes", Journal of American Heart Association, 2007, pp. 432-441, vol. 115.

Moskovitz et al., "Methionine sulfoxide reductase (MsrA) is a regulator of antioxidant defense and lifespan in mammals", Proceedings of the National Academy of Science, Nov. 6, 2001, pp. 12920-12925, vol. 98, No. 23.

Munzel et al.,"Are ACE Inhibitors a "Magic Bullet" Against Oxidative Stress?", Journal of American Heart Association, 2001, pp. 1571-1574, vol. 104.

Olivetti et al., "Apoptosis in the Failing Human Heart", The New England Journal of Medicine, Apr. 17, 1997, pp. 1131-1141, vol. 336, No. 16.

Patton et al., "Activation of Type II Calcium/Calmodulin-dependent Protein Kinase by Ca2+/Calmodulin Is Inhibited by Autophosphorylation of Threonine within the Calmodulin-binding Domain", Journal of Biological Chemistry, Jul. 5, 1990, pp. 11204-11212, vol. 265, No. 19.

Pfeffer et al., "Valsartan, Captopril, or Both in Myocardial Infarction complicated by Heart Failure, Left Ventricular Dysfunction, or Both", The New England Journal of Medicine, Nov. 13, 2003, pp. 1893-1907, vol. 349, No. 20.

Reynaert et al., "Dynamic redox control of NF-KB through glutaredoxin-regulated S-glutathionylation of inhibitory KB kinase beta", Proceedings of the National Academy of Science, Aug. 29, 2006, pp. 13086-13091, vol. 103, No. 35.

Rosenberg et al., "Structure of the Autoinhibited Kinase Domain of CaMKII and SAXS Analysis of the Holoenzyme", Cell, Dec. 2, 2005, pp. 849-860, vol. 123.

Ruan et al., "High-quality life extension by the enzyme peptide methionine sulfoxide reductase", Proceedings of the National Academy of Science, Mar. 5, 2002, pp. 2748-2753, vol. 99, No. 5.

Saitoh et al., "Phosphorylation-dependent Subcellular Translocation of a Ca2+/Calmodulin-dependent Protein Kinase Produces an Autonomous Enzyme in *Aplysia* Neurons", The Journal of Cell Biology, Mar. 1985, pp. 835-842, vol. 100.

Santarelli et al., "Three methionine residues located within the regulator of conductance for K+ (RCK) domains confer oxidative sensitivity to large-conductance Ca2+-activated K+ channels", Journal of Physiology, 2006, pp. 329-348, vol. 571, No. 2.

Schulman et al., "Ca2+-dependent proteing phosphorylation system in membranes from various tissues, and its activation by 'calcium-dependent regulator'," Proceedings of the National Academy of Science, Nov. 1978, pp. 5432-5436, vol. 75, No. 11.

Tojo et al., "Angiotensin II and Oxidative Stress in Dahl Salt-Sensitive Rat With Heart Failure", Journal of the American Heart Association, 2002, pp. 834-839, vol. 40.

Weiss et al., "Caldific Aortic Valve Stenosis in Old Hypercholesterolemic Mice", Journal of the American Heart Association, 2006, pp. 2065-2069, vol. 114.

Wu et al., "Calmodulin Kinase II and Arrhythmias in a Mouse Model of Cardiac Hypertrophy", Journal of American Heart Association, 2002, pp. 1288-1293, vol. 106.

Yang et al., "Calmodulin kinase II inhibition protects against myocardial cell apoptosis in vivo", American Journal of Physiological Heart Circulation, 2006, pp. H3065-H3075, vol. 291.

Zhabotinsky, "Bistability in the Ca2+/Calmodulin-Dependent Protein Kinase-Phosphatase System", Biophysical Journal, Nov. 2000, pp. 2211-2221, vol. 79.

Zhu et al., "Linkage of beta1-adrenergic stimulation to apoptotic heart cell death through protein kinase A-independent activation of Ca2+/calmodulin kinase II", Journal of Clinical Investigation, Mar. 2003, pp. 617-625, vol. 111, No. 5.

Zhu et al. Activation of CaMKII is a Common Intermediate of Diverse Death Stimuli-induced Heart Muscle Cell Apoptosis, Journal of Biological Chemistry, Apr. 6, 2007, pp. 10833-10839, vol. 282, No. 14.

Zimmerman et al., "Requirement for Rac1-Dependent NADPH Oxidase in the Cardiovascular and Dipsogenic Actions of Angiotensin II in the Brain", Journal of American Heart Association, 2004, pp. 532-539, vol. 95.

Zangerle et al., "Screening of Thiol Compounds: Depolarization-Induced Release of Glutathione and Cysteine from Rat Brain Slices", Journal of Neurochemistry, 1992, pp. 181-189, vol. 59, No. 1.

Zhang et al., "Calmodulin kinase II inhibition protects against structural heart disease", Nature Medicine, Apr. 2005, pp. 409-417, vol. 11, No. 4.

\* cited by examiner

FIG. 1
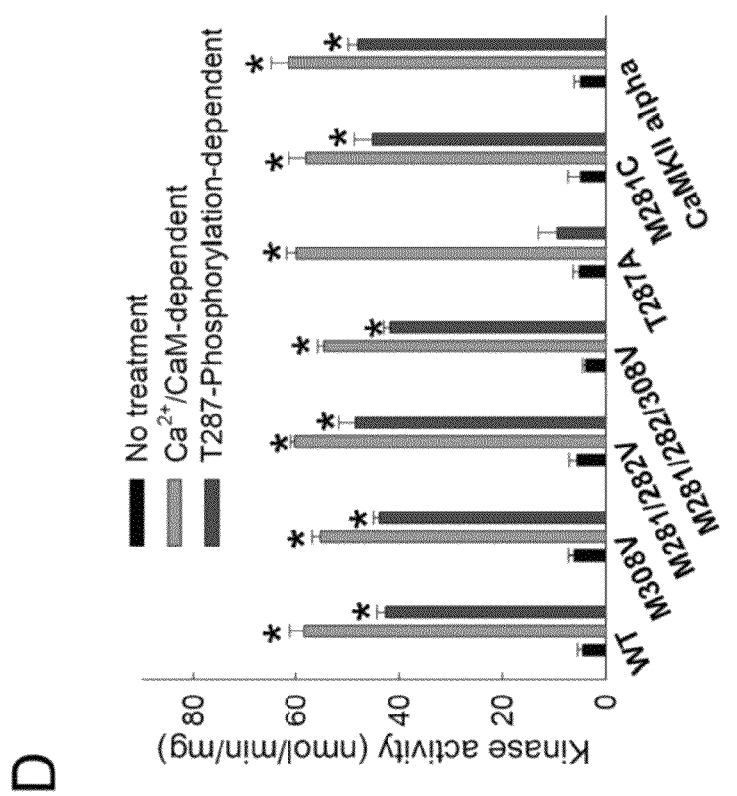
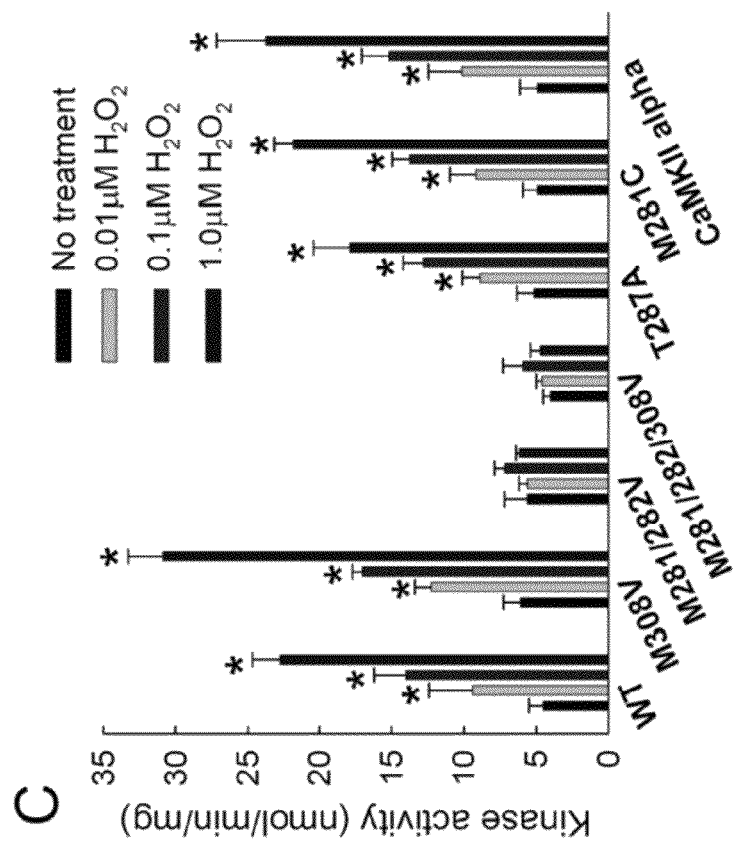

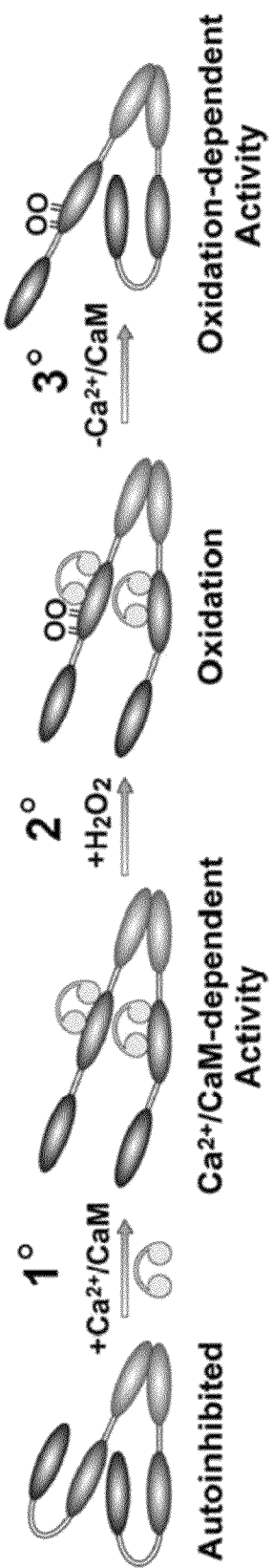

FIG. 6

Saline AngII

WT p47⁻/⁻

FIG. 8
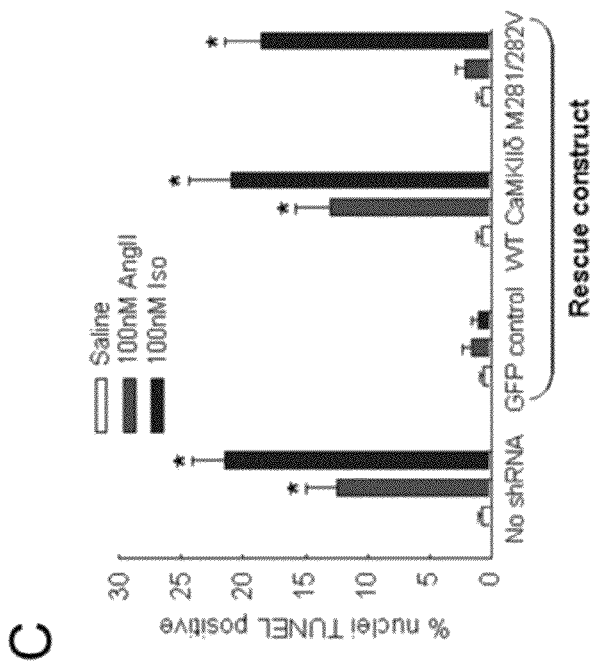
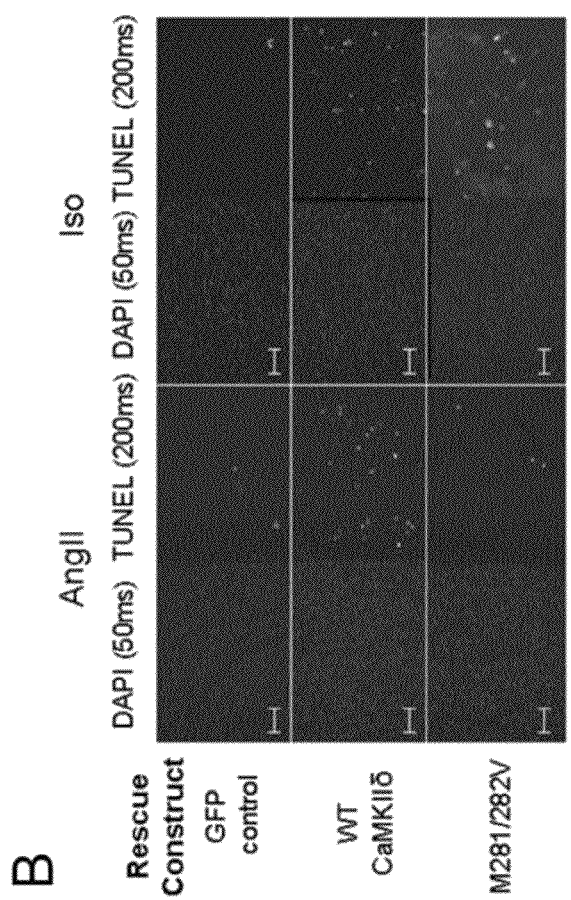

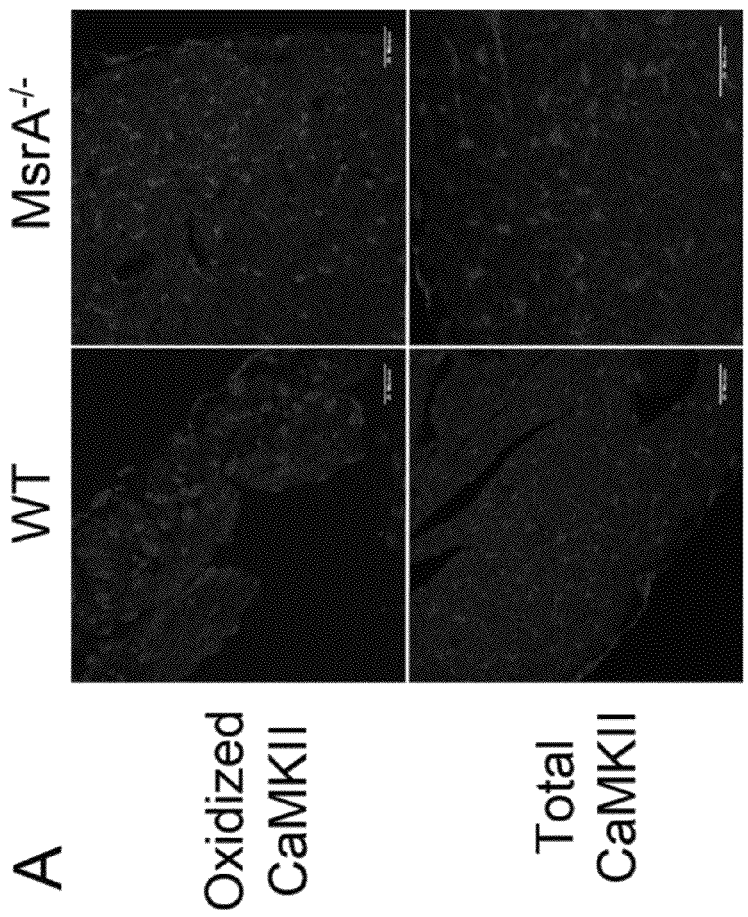

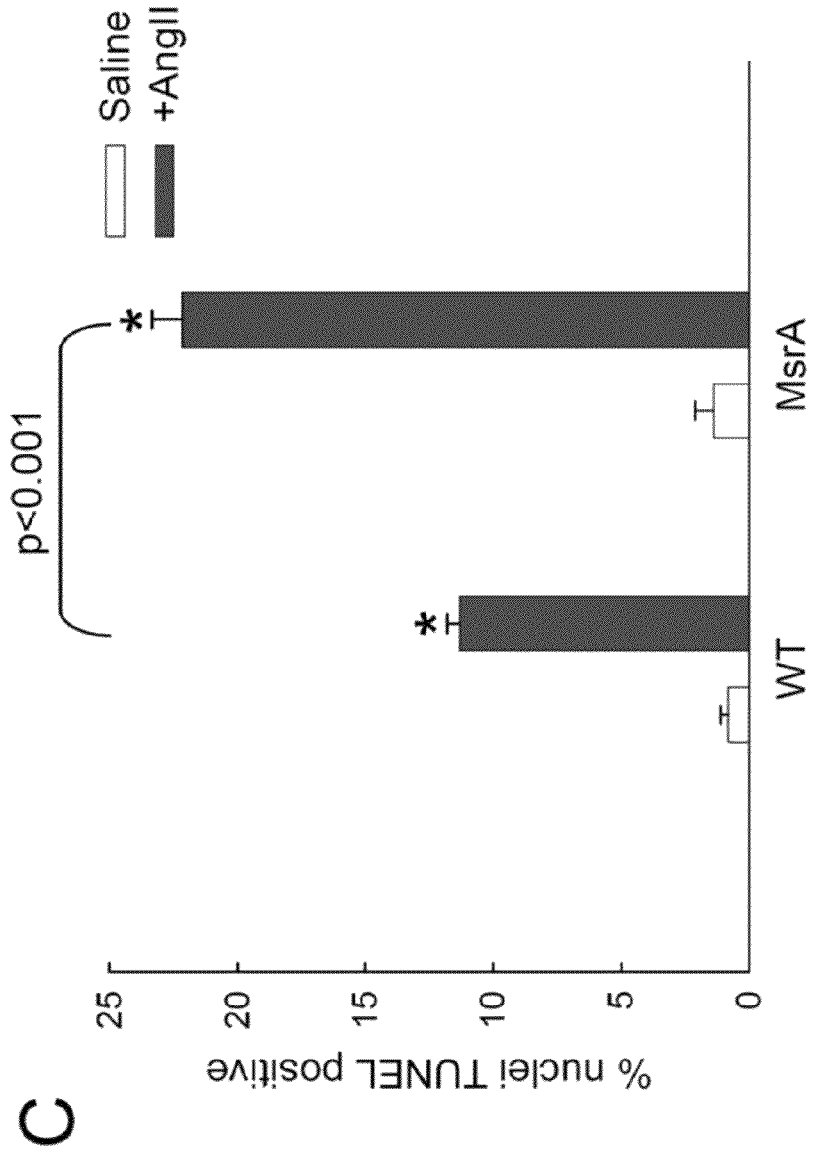

FIG. 12 Neonatal cardiomyocytes

FIG. 13 Mouse heart sections

| Mouse ID | Cancer | Treatment |
|---|---|---|
| 1L | Lung | Saline |
| 1B | None | Saline |
| 8R | FADU | Keto/Rad |
| 21TR | FADU | Keto |
| 1N | None | 2DG (87 days prior to bleed) |
| 10D | FADU | Saline/Rad |
| 21L | None | Keto |
| 11D | FADU | Saline |

US 8,841,423 B2

MONOCLONAL ANTIBODIES SPECIFIC FOR OXIDIZED CALCIUM/CALMODULIN DEPENDENT PROTEIN KINASE II

CROSS-REFERENCE TO RELATED APPLICATIONS

The present application claims the benefit under 35 U.S.C. §119(e) to U.S. Provisional Application No. 61/048,259, filed on Apr. 28, 2008, the content of which is incorporated herein by reference in its entirety.

STATEMENT REGARDING FEDERALLY SPONSORED RESEARCH OR DEVELOPMENT

This invention was made with U.S. Government Support from the following agency: NIH, Grant Nos. R01 HL 079031, R01 HL 62494, and R01 HL 70250. The U.S. Government has certain rights in the invention.

FIELD

The field of the invention relates to calcium/calmodulin dependent protein kinase II (CaMKII). In particular, the field relates to methods for detecting oxidized forms of CaMKII in order to characterize or diagnose a disease or condition. The field also relates to methods for modulating the activity of CaMKII, either directly or indirectly, to order to treat or prevent a disease or condition.

BACKGROUND

Excessive oxidation is thought to cause or contribute to heart failure and cardiac arrhythmias, cancer, premature aging, atherosclerosis, Alzheimer's disease, and sepsis. The multifunctional calcium and calmodulin-dependent protein kinase II (CaMKII) now has been identified as a novel molecular target for activation by oxidation. (See Erickson e.g., accepted for publication in Cell, projected publication date May 2, 2008 [hereinafter Erickson e.g., Cell 2008]).

Oxidation activates CaMKII (Erickson e.g., *Cell* 2008). Activated CaMKII can cause heart failure and arrhythmias and is implicated in progression of cancer, neurological disease, and sepsis. In particular, CaMKII oxidation has been shown to play a pivotal role in cardiac cell death during angiotensin II mediated apoptosis. CaMKII oxidation increases during myocardial ischemia and infarction (Erickson *Cell* 2008) and causes cellular damage (Yang *AJP* 2006) and cardiac dysfunction after myocardial infarction (Zhang *Nat Med* 2005). Additionally, regulation of CaMKII activity by oxidation may play a role in cancer, aging, sepsis, cell development and differentiation, because each of these conditions is marked by increased oxidation and CaMKII activity.

Although oxidation is a bona fide pathological signal in important human diseases, diagnostic measures of oxidative stress suitable for clinical applications are lacking. Another problem in utilizing alternative measures of oxidant stress is that they are not directly linked to disease progression. (See, e.g., Roberts Free Radical Biology and Medicine 2007, (discussing the molecular biology of isoprostanes).) Here, it is shown that oxidation of CaMKII causes enhanced CaMKII activity by preventing refolding of the enzyme into an inactive (resting) conformation. CaMKII is unusual because it is a target for oxidation and CaMKII's role in disease and the mechanism of activation by oxidation are understood. (See Erickson e.g., *Cell* 2008). Thus, measuring oxidized CaMKII may provide the first opportunity to track oxidation of a biologically active molecule present in peripheral blood or biopsy specimens. In contrast, other measures of oxidative stress are 'bystander' molecules not directly implicated in disease pathogenesis (e.g., isoprostanes). In addition to diagnostic clinical applications; researchers in the areas of nerve, muscle, heart, infectious disease and cancer biology may benefit from a reagent that can be used to measure oxidant burden, and in particular oxidant-activated CaMKII.

Although CaMKII is a validated target for heart failure and arrhythmias and is implicated as a causal agent in cancer, neurological diseases and aging, there are currently no available methodologies to non-invasively measure oxidized CaMKII activity. A method to detect oxidized CaMKII may be valuable as a diagnostic tool (e.g., to monitor the success of antioxidant therapy, antibacterial therapy, chemotherapy or future therapies that involve inhibiting CaMKII). In addition, the ability to measure oxidized CaMKII may be invaluable to researchers attempting to connect oxidative stress with CaMKII activation in these fields. Current antibodies only detect either total CaMKII or the phosphorylated form of CaMKII.

Here, an immune serum (rabbit) against the oxidized form of CaMKII was developed and purified by binding to protein A beads. This serum can be used to detect the presence of oxidized CaMKII in heart, blood and other tissues or body fluids using a number of techniques, including Western blot and immunofluorescent imaging. This antiserum may be used to measure oxidized CaMKII in patients from peripheral blood and/or biopsy specimens. In particular, the serum was utilized to detect elevated levels of oxidized CaMKII in blood from mice that serve as models for various human diseases or conditions.

SUMMARY

Calcium/calmodulin dependent protein kinase II (CaMKII) has been found to be directly oxidized. Furthermore, direct oxidation of CaMKII was observed to result in calcium independent activation oxCaMKII. Antibodies that bind specifically to oxidized forms of CaMKII (oxCaMKII) were generated and were utilized to detect oxCaMKII in blood from: (1) mice with cancer; (2) mice with premature aging due to knock out of the gene encoding methionine sulfoxide reductase A (MsrA−/−); (3) mice injected with angiotensin II (a cause of cardiac hypertrophy and failure); (4) mice injected with bacterial endotoxin (a model of sepsis); (5) mice fed a pro-oxidant (ketogenic) diet; and (6) mice with cancer that had been treated with experimental therapy (e.g., 2-deoxyglucose or radiation).

Disclosed is an isolated or purified antibody or an antigen-binding fragment thereof that binds specifically to oxidized calcium/calmodulin-dependent protein kinase II (ox-CaMKII) or a fragment thereof. The antibody may be monoclonal or polyclonal. In some embodiments, the antibody or antigen-binding fragment thereof is an Fab fragment, an F(ab')$_2$ fragment, a dAb fragment, or a single chain Fv (scFv).

The antibody may include a human, mouse, rat, guinea pig, rabbit, dog, cat, pig, goat, horse or cow antibody, and in some embodiments, the antibody or antigen-binding fragment may be chimeric. In further embodiments, the antibody or antigen-binding fragment may be humanized.

Typically, the antibody or antigen-binding fragment thereof binds specifically to oxCaMKII or a fragment thereof. In some embodiments, the antibody or antigen-binding fragment thereof binds specifically to a peptide consisting of an amino acid sequence selected from the consensus amino acid sequence {S,C}{H,Q}RSTVAS{C,M}MHRQETV{D,E} (SEQ ID NO:4) in which the cysteine or methionine at position 9 and the methionine at position 10 are oxidized. In further embodiments, the antibody or antigen-binding fragment thereof binds specifically to oxCaMKII delta having oxidized methionine residues at positions 281 and 282 (e.g., an oxidized peptide consisting of an amino acid sequence of CQRSTVASMMHRQETVD (SEQ ID NO:5)).

The antibody or antigen-binding fragment thereof may include a label such as a radiolabel, a fluorophore, an enzyme, a colloidal metal (e.g., gold), or a colored nanoparticle, and the labeled antibody may be utilized in an immunoassay to detect oxCaMKII in a biological sample from a patient. Biological samples may include, but are not limited to, tissue samples and blood products (e.g., plasma).

The antibody or antigen-binding fragment thereof may be immobilized. For example, the antibody or antigen-binding fragment thereof may be covalently or non-covalently bound to a solid support. The immobilized antibody or antigen-binding fragment thereof may be utilized in an immunoassay to detect oxCaMKII in a biological sample from a patient.

Also disclosed is an isolated or purified CaMKII polypeptide or an immunogenic fragment thereof that include one or more oxidized methionine residues at amino acid positions 281 or 282 (preferably both methionine residues at amino acid positions 281 and 282). The immunogenic fragment preferably includes at least about 8 amino acids (more preferably at least about 10, 12, 14, 16, 18, or 20 amino acids) that span amino acid positions 281 or 282 (e.g., an immunogenic fragment that includes amino acid sequences of SEQ ID NOS:1, 2, 3, 4, or 5).

Also disclosed are compositions that comprise the isolated or purified CaMKII polypeptide or an immunogenic fragment thereof that include one or more oxidized methionine residues at amino acid positions 281 or 282 (i.e., oxCaMKII). In some embodiments of the compositions, oxCaMKII represents at least about 50% of the total amount of CaMKII in the composition (preferably oxCaMKII represents at least about 70% of the total amount of CaMKII in the composition, more preferably oxCaMKII represents at least about 90% of the total amount of CaMKII in the composition).

Also disclosed is a method for preparing antisera that binds specifically to oxidized calcium/calmodulin-dependent protein kinase II (oxCaMKII). The method typically includes: (a) administering to an animal a composition comprising CaMKII or an immunogenic fragment thereof having one or more oxidized amino acids selected from a group consisting of oxidized methionine and oxidized cysteine; (b) and isolating antisera from the animal. Optionally, the composition further includes an adjuvant. The oxCaMKII or the immunogenic fragment thereof may be prepared by reacting CaMKII or an immunogenic fragment thereof with an oxidizing agent. Preferably, the one or more oxidized amino acids include oxidized methionine residues at positions 281 and 282 relative to the full-length CaMKII delta polypeptide or at corresponding positions in an immunogenic fragment of CaMKII delta polypeptide (e.g., oxidized methionine residues at amino acid positions 9 and 10 of SEQ ID NO:5).

Also disclosed are isolated or purified cells that produce antibody that binds specifically to oxCaMKII or an oxidized fragment thereof. Cells that produce antibody may include hybridomas or plasmacytomas.

The disclosed antibody or antigen binding fragment thereof may be utilized in methods for detecting oxCaMKII or fragments thereof. For example, a method of detecting oxCaMKII may include: (a) contacting a biological sample from a patient with an antibody or antigen-binding fragment thereof that binds specifically to oxCaMKII and forms a complex; and (b) detecting the complex. Suitable biological samples may include, but are not limited to, blood and plasma. The method may be utilized to characterize a disease or condition in the patient (e.g., a cardiac disease or condition, cancer, premature aging, atherosclerosis, Alzheimer's disease, or sepsis).

In one embodiment, the disclosed methods are utilized to detect oxCaMKII in a biological sample from a patient where the patient has or is at risk for developing a disease or condition selected from a group consisting of a cardiac disease, cancer, premature aging, atherosclerosis, Alzheimer's disease, or sepsis. The method further may include: (c) administering a therapeutic agent to the patient (or not administering a therapeutic agent to the patient) based on detecting oxCaMKII (or not detecting oxCaMKII) in the biological sample from the patient.

In a further embodiment, the method may be utilized to detect oxCaMKII in a patient that is undergoing pharmacological therapy (e.g., pharmacological therapy with an angiotensin converting enzyme (ACE) inhibitor, an antioxidant agent, an antibacterial agent, or an anticancer agent). In this further embodiment, the method further may include: (c) modulating the pharmacological therapy based on detecting or not detecting oxCaMKII. For example, modulating the therapy may include increasing or decreasing dosage of the pharmacological agent based on detecting or not detecting oxCaMKII. The methods may include assessing oxidative stress.

Also disclosed are kits for detecting oxCaMKII. The kits may include: (a) an antibody or antigen-binding fragment thereof that binds specifically to oxCaMKII to form a complex; and (b) a label for detecting the complex.

Further disclosed are pharmaceutical compositions. The compositions may include: (a) an antibody or antigen-binding fragment thereof that binds specifically to oxCaMKII; and (b) a pharmaceutically acceptable carrier.

Further disclosed are methods for treating or preventing structural heart disease in a patient. The methods include administering to the patient an antibody or antigen-binding fragment thereof that binds specifically to oxCaMKII, for example where the antibody or antigen-binding fragment inhibits activity of oxCaMKII. In some embodiments of the methods, the antibody or antigen-binding fragment binds specifically to oxCaMKII delta having oxidized methionine residues at positions 281 and 282.

Further disclosed are methods for treating or preventing structural heart disease in a patient, which methods include administering to the patient a therapeutic agent that specifically inhibits oxidation of CaMKII. For example, the therapeutic agent may specifically inhibit oxidation of CaMKII at methionine residues present at amino acid positions 281 and 282. In some embodiments, the methods include administering to the patient a therapeutic agent that increases methionine sulfoxide reductase (MSR) activity in the patient. The therapeutic agent may increase MSR activity (e.g., by increasing MSR expression) which subsequently augments the conversion of oxidized methionines in CaMKII to non-oxidized methionines (e.g., augmenting conversion of oxidized methionine residues present at amino acid positions 281 and 282 of CaMKII to non-oxidized states).

BRIEF DESCRIPTION OF THE DRAWINGS

FIG. 6. Wild type heart sections have increased T287-phosphorylated CaMKII after AngII treatment. Wild type and p47$^{-/-}$ mice were treated with AngII (3 mg/kg/day) for 1 week. Heart sections from these mice were stained with an antibody against T287-phosphorylated or total CaMKII.

DETAILED DESCRIPTION

Definitions

Figure 1:
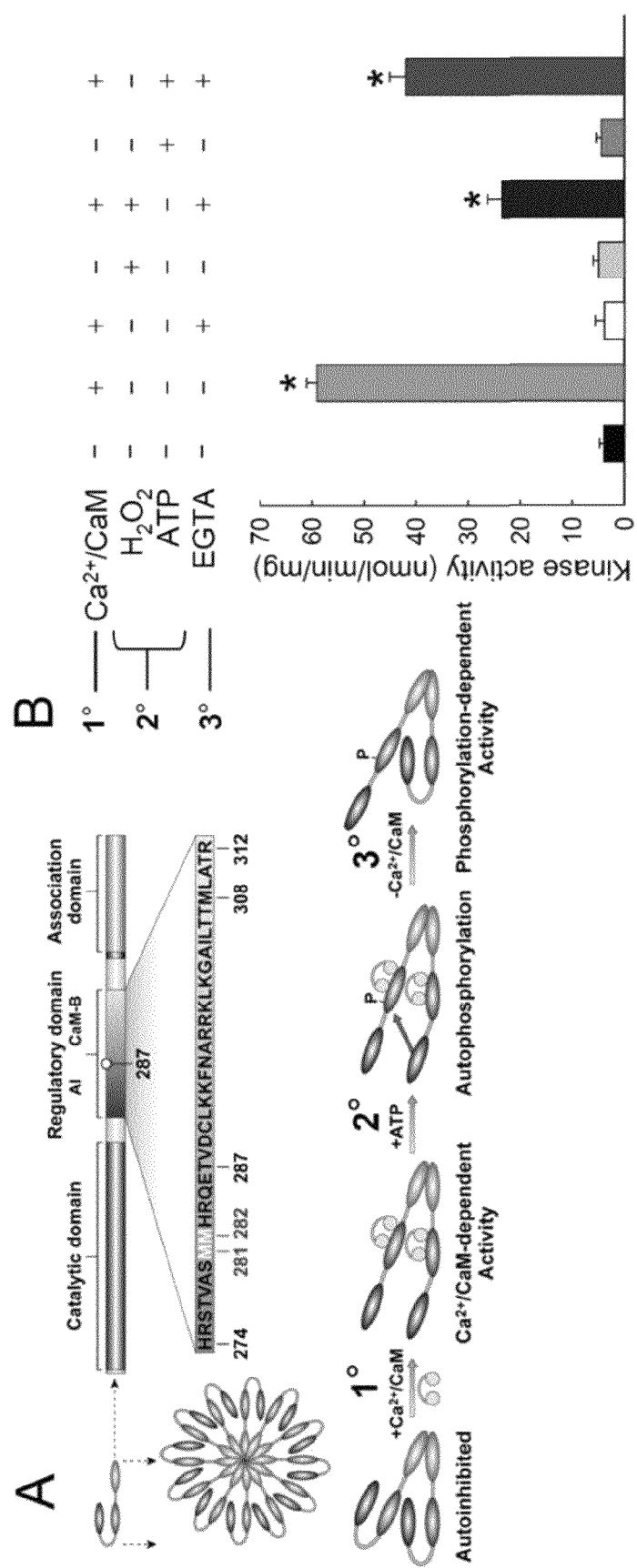
FIG. 1. CaMKII is activated by reactive oxygen species (ROS). (A) General structure of a subunit from the multimeric holoenzyme CaMKII and mechanism of CaMKII activation by autophosphorylation. The amino acid sequence of the regulatory domain is highlighted to show the autoinhibitory (AI) and calmodulin-binding (CaM-B) regions. Yellow symbols represent CaM. Pretreatment with $Ca^{2+}$/CaM (1°) followed by phosphorylation at T287 (2°) yields persistent activity even after the removal of $Ca^{2+}$/CaM (3°). (B) Kinase assays were performed after three distinct treatment steps: (1°)±$Ca^{2+}$/CaM, (2°)±$H_2O_2$ or ATP, and (3°)±EGTA. (n=6 assays/group, * p<0.05 vs. WT no treatment). (C) CaMKII is activated by $H_2O_2$ in a dose-dependent manner after pretreatment with $Ca^{2+}$/CaM. Oxidation-dependent CaMKII activity is ablated in M281/282V mutants (n=6 assays/group, * p<0.05 vs. WT no treatment). (D) M281/282V mutants have normal $Ca^{2+}$/CaM-dependent and T287-autophosphorylation-dependent activation (n=6 assays/group, * p<0.05 vs. WT no treatment). (E) Proposed mechanism for activation of CaMKII by oxidation. After initial activation of the holoenzyme by $Ca^{2+}$/CaM (1°), oxidation at M281/282 (2°) blocks re-association of the catalytic domain, yielding persistent CaMKII activity (3°).

The present invention is described herein using several definitions, as set forth below and throughout the application.

As used herein, "a," "an," and "the" mean "one or more" unless the context clearly dictates otherwise. For example, reference to "an antibody" includes one or more antibodies. Reference to "an inhibitor" includes one or more inhibitors.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, a "patient" may be interchangeable with "subject" and includes human and non-human animals. Non-human animals may include dogs, cats, horses, cows, pigs, sheep, and the like.

A "patient in need thereof" may include a patient in need of diagnosis, characterization, treatment, prognosis, or prevention with respect to a disease or condition associated with oxidation of calcium/calmodulin dependent protein kinase II. Examples of diseases or conditions may include, but are not limited to, cardiac diseases or conditions, cancer, premature aging, atherosclerosis, Alzheimer's disease, and sepsis. A "patient in need thereof" may include a patient undergoing therapy to treat a disease or condition that may include, but is not limited to, a cardiac disease or condition, cancer, premature aging, atherosclerosis, Alzheimer's disease, and sepsis. For example, a "patient in need thereof" may include a patient having heart failure, where the patient is undergoing a pharmacological treatment to reduce cardiac dysfunction or mortality (e.g., treatment with angiotensin-converting enzyme (ACE) inhibitors). Furthermore, a "patient in need thereof" may include a patient having a cardiac disease or condition, cancer, premature aging, atherosclerosis, Alzheimer's disease, or sepsis, where the patient is undergoing a pharmacological therapy selected from an anti-oxidant therapy, an anti-bacterial therapy, or an anti-cancer therapy.

As used herein, "cardiac diseases or conditions" may include structural heart diseases (e.g., myocardial infarction, cardiac dysfunction following myocardial infarction, reduced myocardial contractility, end-stage valve disease, and dilated cardiomyopathy). Cardiac diseases or conditions may include those diseases or conditions associated with ischemic injury, which means the damage or potential damage to an organ or tissue that results from the interruption of blood flow to the organ or tissue (i.e., an "ischemic event"). A "patient in need thereof" can be a patient diagnosed as having a myocardial infarction. The subject can be a patient diagnosed as having post-infarction cardiac dysfunction. The subject can be a patient who has been diagnosed as having had a myocardial infarction who is, thus, at increased risk of developing post-infarction cardiac dysfunction. Furthermore, the subject can be a patient diagnosed as having dilated cardiomyopathy or symptoms of heart failure from any cause associated with a phenotype of cardiac chamber dilation and reduced myocardial contractile function. The subject can be a patient diagnosed as having reduced myocardial contractility. The subject can be a patient diagnosed with atrial fibrillation.

As used herein, "CaMKII" refers to the enzyme "calcium/calmodulin dependent protein kinase II." In humans, there are four separate, highly homologous genes for CaMKII called alpha, beta, delta, or gamma (or α, β, δ and γ). Multiple isoforms of these genes are expressed through alternative splicing mechanisms. Representative sequences for the isoforms of these genes have been submitted to public depositories such as GenBank and include: GenBank Accession No. NP_741960, CaMKII alpha isoform 2; GenBank Accession No. NP_057065, CaMKII alpha isoform I; GenBank Accession No. NP_742079, CaMKII beta isoform 6; GenBank Accession No. NP_742080, CaMKII beta isoform 7; GenBank Accession No. NP_742077, CaMKII beta isoform 4; GenBank Accession No. NP_001211, CaMKII beta isoform I; GenBank Accession No. NP_742081, CaMKII beta isoform 8; GenBank Accession No. NP_742078, CaMKII beta isoform 5; GenBank Accession No. NP_742076, CaMKII beta isoform 3; GenBank Accession No. NP_742075, CaMKII beta isoform 2; GenBank Accession No. NP_001212, CaMKII delta isoform 3; GenBank Accession No. NP_742126, CaMKII delta isoform 2; GenBank Accession No. NP_742125, CaMKII isoform 1; GenBank Accession No. NP_742113, CaMKII isoform 1; GenBank Accession No. NP_001020609, CaMKII delta isoform 2 (SEQ ID NO:12); NP_751910, CaMKII gamma isoform 3; GenBank Accession No. NP_751913, CaMKII gamma isoform 6; GenBank Accession No. NP_751913, CaMKII gamma isoform 6; GenBank Accession No. NP_751911, CaMKII gamma isoform 1; GenBank Accession No. NP_751909, CaMKII gamma isoform 2; GenBank Accession No. NP_751909, CaMKII gamma isoform 2; GenBank Accession No. NP_001213, CaMKII gamma isoform 4; all of which GenBank entries are incorporated herein by reference in their entireties.

CaMKIIα and β are neuronal, while CaMKIIδ and γ are expressed in neurons and in peripheral (non-neuronal) tissue. In some embodiments, the disclosed antiserum detects oxidation of a Met pair at positions 281/282 in CaMKIIδ, the predominant peripheral form of CaMKII. Based on the fact that this Met pair is conserved in CaMKIIβ, δ and γ, it is expected that the disclosed antiserum will detect the oxidized forms of these other isoforms. In CaMKIIα, which is a neuronally expressed CaMKII, a Cys is substituted for the first Met at position 280 (corresponding to Met position 281 in CaMKIIβ, δ and γ). However, it is known that CaMKIIα is activated by oxidation with a similar $H_2O_2$ dose-activity relationship compared to CaMKIIδ and that mutation of Met281Cys in CaMKIIδ (to mimic the Cys-Met in CaMKIIα at positions 280/281) does not affect oxidative activation. Therefore, all of the four CaMKII isoforms are activated by oxidation via a similar mechanism (i.e., oxidation of Mets 281/282 in β, γ and δ or oxidation of Cys280 and Met281 in α). Because the Cys side chain is a well-recognized target for oxidation, it is expected that the disclosed antisera will be effective against each of the CaMKII isoforms (α-γ).

The CaMKII polypeptides disclosed herein may include the consensus sequence {S,C}{H,Q}RSTVAS{C,M}MHRQETV{D,E} (SEQ ID NO:4). For example, full-length CaMKII polypeptides may include the consensus sequence {S,C}{H,Q}RSTVAS{C,M}MHRQETV{D,E} (SEQ ID NO:4) at about amino acid positions 272-288 in a full-length isoform of CaMKII alpha or at about amino acid positions 273-289 in a full-length isoform of CaMKII beta, delta, or gamma. The CaMKII polypeptides disclosed herein may comprise an oxidized cysteine or methionine residue at positions 9 and 10 of the consensus sequence {S,C}{H,Q}RSTVAS{C,M}MHRQETV{D,E} (SEQ ID NO:4), which oxidized residue or methionine residue may be present at about amino acid positions 280 and 281 in a full-length isoform of CaMKII alpha or at about amino acid positions 281 and 282 in a full-length isoform of CaMKII beta, delta, or gamma.

Disclosed herein are antibodies or antigen binding fragments thereof that bind specifically to an oxidized form of CaMKII or a fragment thereof. The term "antibody" as used herein refers to an immunoglobulin molecule or an immunologically active portion thereof (i.e., an antigen-binding portion). As used herein, the term "antibody" refers to a protein comprising at least one, and preferably two, heavy (H) chain variable regions (abbreviated as VH), and at least one and preferably two light (L) chain variable regions (abbreviated as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined. (See, e.g., Kabat, E. A., e.g. (1991) Sequences of Proteins of Immunological Interest, Fifth Edition, U.S. Department of Health and Human Services, NIH Publication No. 91 3242; and Chothia, C. e.g. (1987) J. Mol. Biol. 196: 901-917; which are incorporated herein by reference). Each VH and VL is composed of three CDR's and four FRs, arranged from amino-terminus to carboxy-terminus in the following order: FR 1, CDR1, FR2, CDR2, FR3, CDR3, FR4.

The term "antigen-binding fragment" of an antibody (or simply "antibody portion" or "fragment"), as used herein, refers to one or more fragments of a full-length antibody that retain the ability to specifically bind to the antigen (e.g., oxidized CaMKII or a fragment thereof). Examples of antigen-binding fragments of the disclosed antibodies include, but are not limited to: (i) an Fab fragment or a monovalent fragment consisting of the VL, VH, CL and CH1 domains; (ii) an F(ab')$_2$ fragment or a bivalent fragment comprising two Fab fragments linked by a disulfide bridge at the hinge region; (iii) an Fd fragment consisting of the VH and CH1 domains; (iv) a Fv fragment consisting of the VL and VH domains of a single arm of an antibody, (v) a dAb fragment (Ward e.g., (1989) Nature 341:544 546), which consists of a VH domain; and (vi) an isolated complementarity determining region (CDR). Even though the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv or "scFv." (See, e.g., Bird e.g. (1988) Science 242:423 426; and Huston e.g. (1988) Proc. Natl. Acad. Sci. USA 85:5879 5883). Single chain Fv or "scFv" are encompassed within the term "antigen-binding fragment" of an antibody.

The disclosed antibodies can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')$_2$ or scFV fragment, or one or more CDRs). The antibodies disclosed herein may be a polyclonal or monoclonal antibodies. The disclosed antibodies may be monospecific, (e.g., a monoclonal antibody, or an antigen-binding fragment thereof), or may be multispecific (e.g., bispecific recombinant diabodies). In some embodiments, the antibody can be recombinantly produced (e.g., produced by phage display or by combinatorial methods). In some embodiments, the antibodies (or fragments thereof) are recombinant or modified antibodies (e.g., a chimeric, a humanized, a deimmunized, or an in vitro generated antibody).

The disclosed antibodies or antigen binding fragments thereof bind specifically to oxidized CaMKII or an oxidized fragment thereof (e.g., an oxidized peptide comprising an amino acid sequence of SEQ ID NO:1, 2, 3, 4, or 5). As disclosed herein, an antibody that binds specifically to oxidized CaMKII will bind to oxidized CaMKII and will not bind to non-oxidized CaMKII. For example, an antibody that binds to CaMKII (beta, delta, or gamma) having oxidized methionine residues at positions 281/282 and that does not bind to CaMKII (beta, delta, or gamma) having non-oxidized methionine residues at positions 281/282 is an antibody that binds specifically to oxidized CaMKII. An antibody that binds to CaMKII alpha having oxidized cysteine and methionine residues at positions 280/281 and that does not bind to CaMKII alpha having non-oxidized cysteine and methionine residues at positions 280/281 is an antibody that binds specifically to oxidized CaMKII.

The disclosed antibodies or antigen binding fragments thereof may include a label. Labels may include, but are not limited to radioisotopes, bioluminescent compounds, chemiluminescent compounds, fluorescent compounds, metal chelates, an enzymes, colloidal metals (e.g., gold), and colored nanoparticles.

The presently disclosed methods may include performing immunoassays that utilize an antibody or antigen binding fragment thereof against oxCaMKII. The term "immunoassay" as used herein refers to a method of detecting or measuring antigens, in this case oxCaMKII, by using antibodies or antigen binding fragments thereof as reagents. The antibodies can be polyclonal or, preferably, monoclonal. The terms "polyclonal antibodies" and "monoclonal antibodies" have the standard meanings understood by those skilled in the art and refer to antibodies, either a mixture of different antibodies in the case of polyclonal antibodies, or a single antibody in the case of monoclonal antibodies, both of which are produced, in general, by immunization of an animal with an antigen. In the case of monoclonal antibodies, antibody-producing cells are selected from the animal and fused with myeloma cells. These cells are then cultured. The antibodies of the present invention detect oxCaMKII to a desired level. Harlow, E. and Lane, D. (1988) Antibodies: A Laboratory Manual (Cold Spring Harbor Laboratory), which is incorporated by reference in its entirety herein teaches methods regarding the making and usage of antibodies. The anti-oxCaMKII antibodies and antigen binding fragments thereof may be labeled or immobilized as disclosed herein.

In the disclosed immunoassays, the antibodies or antigen binding fragments thereof may be utilized in liquid phase or bound to a solid phase carrier. Examples of types of immunoassays include competitive and non-competitive immunoassays in either a direct or indirect format. Further examples of such immunoassays are the radioimmunoassay (RIA) and the sandwich (immunometric) assay. Detection of the antigens using the monoclonal antibodies of the invention can be performed utilizing immunoassays which are run in either the forward, reverse, or simultaneous modes, including immunohistochemical assays on physiological samples. Alternatively, the antibody of the invention can be used to detect oxidized forms of CaMKII present in electrophoretically dispersed gel protocols such as Western blots and two-dimensional gels. The antibodies or antigen binding fragments thereof may be bound to carriers and used to detect the presence of oxidized forms of CaMKII. Examples of well-known carriers include glass, polystyrene, polypropylene, polyethylene, dextran, nylon, amylases, natural and modified celluloses, polyacrylamides, agaroses and magnetite.

The presently disclosed methods and immunoassays may include determining a control value for oxCaMKII. The term "control value" as used herein refers to a basal level of oxCaMKII that is normal (i.e., the amount present in a corresponding healthy cohort in the absence of any pathology (disease or disorder) which is associated with oxCaMKII). Such control values may account for the age of the individual and may be directed to certain age ranges. Such control values additionally may account for gender, race, and environmental exposures to pro-oxidants (e.g., smoking, diet, and the like).

Also disclosed are oxidized forms of CaMKII or immunogenic fragments thereof. The oxidized forms of CaMKII or immunogenic fragments thereof may be isolated or purified (e.g., where an isolated or purified, oxidized form of CaMKII or an immunogenic fragment thereof represents at least about 50% of total protein in an isolated or purified sample, and preferably at least about 70%, 90%, or 95% of total protein in an isolated or purified sample). In some embodiments, the oxidized forms of CaMKII or immunogenic fragments include at least one oxidized methionine or at least one oxidized cysteine. An oxidized methionine may be partially or fully oxidized and may include methionine sulfoxide and methionine sulfone. An oxidized cysteine may be partially or fully oxidized and may include cystine and cysteic acid. An oxidized, immunogenic fragment of CaMKII typically includes at least about 8 amino acids. In some embodiments, an oxidized, immunogenic fragment of CaMKII comprises or consists of an amino acid sequence selected from the consensus sequences STVAS{C,M}MHR (SEQ ID NO:2), TVAS{C,M}MHRQE (SEQ ID NO:3) or {S,C}{H,Q}RSTVAS{C,M}MHRQETV{D,E} (SEQ ID NO:4) and may be formulated as an immunogenic or pharmaceutical composition together with a carrier and optionally an adjuvant.

An oxidized, immunogenic fragment of CaMKII may be used in a method for preparing antibodies or antigenic binding fragments thereof that bind specifically to oxidized CaMKII or an oxidized fragment thereof. For example, an oxidized, immunogenic fragment of CaMKII may be administered to a host animal (e.g., together with an adjuvant) to generate an antibody response. Sera may be collected from the host animal, or antibody producing cells may be isolated from the immunized animal (e.g., spleen cells) to generate immortalized antibody producing cells (e.g., hybridomas or plasmacytomas). Accordingly, hybridomas or plasmacytomas that produce monoclonal antibodies that specifically bind to oxidized CaMKII or an oxidized fragment thereof are contemplated herein. Suitable host animals may include, but are not limited to, mice, rats, rabbits, and the like.

Oxidized forms of CaMKII or immunogenic fragments thereof may be prepared by reacting the CaMKII or immunogenic fragment thereof with an oxidizing agent that converts methionine to methionine sulfoxide or methionine sulfone under physiological conditions. An oxidizing agent also may convert cysteine to cystine or cysteic acid under physiological conditions. Oxidizing agents may include, but are not limited to hydrogen peroxide ($H_2O_2$), alkyl peroxide, peroxy acids, ozone ($O_3$), polyatomic oxygen $O_7$, polyatomic oxygen $O_8$, $NaIO_4$, and potassium peroxymonosulfate (oxone) (Wozniak e.g., Bioorg. Med. Chem. Lett., 8(19):2641 6 (1998)).

Also disclosed herein are mutant or variant forms of CaMKII and polynucleotides that encode mutant or variant forms of CaMKII. In some embodiments, a mutant CaMKII includes one or more amino acid substitutions with respect to the amino acid sequence of wild-type CaMKII. For example, a mutant CaMKII may include an amino acid substitution of a sulfur containing amino acid (e.g., a methionine or a cysteine) for a non-sulfur containing amino acid. Non-methionine and non-cysteine amino acids may include, but are not limited to, glycine, alanine, valine, leucine, isoleucine, phenylalanine, proline, serine, threonine, tyrosine, asparagine, glutamine, tryptophan, aspartic acid, glutamic acid, lysine, arginine, and histidine. In some embodiments, a mutant CaMKII includes one or more substitutions of methionine for a non-methionine residue (e.g., MetMet→ValVal at positions 281/282 in CaMKII beta, delta, or gamma, as indicated in the polypeptide of SEQ ID NO:13). In other embodiments, a mutant CaMKII includes one or more substitutions of cysteine and methionine for non-cysteine/non-methionine residues (e.g., CysMet→ValVal at positions 280/281 in CaMKII alpha).

In some embodiments, the disclosed antibodies or antigen binding fragments thereof, polypeptides, or polynucleotides (collectively "compounds") may be formulated as pharmaceutical compositions that include a therapeutically effective amount of the compounds and one or more pharmaceutically acceptable carriers, excipients, or diluents (i.e., agents), which are nontoxic to the cell or mammal being exposed thereto at the dosages and concentrations employed. Often a physiologically acceptable agent is an aqueous pH buffered solution. Examples of physiologically acceptable carriers include buffers such as phosphate, citrate, and other organic acids; antioxidants including ascorbic acid; proteins, such as serum albumin, or gelatin; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The disclosed pharmaceutical compositions may be immunogenic compositions that optionally include adjuvants. For example, the compositions may include oxCaMKII or a immunogenic fragment thereof and optionally may include an adjuvant. The term "adjuvant" refers to a compound or mixture that enhances the immune response to an antigen. An adjuvant can serve as a tissue depot that slowly releases the antigen and also as a lymphoid system activator that nonspecifically enhances the immune response. For example, adjuvants may include vitamin E acetate solubilisate, aluminum hydroxide, aluminum phosphate or aluminum oxide, (mineral) oil emulsions, non-ionic detergents, squalene and saponins. Other adjuvants which may be used include an oil based adjuvants such as Freund's complete adjuvant (FCA), and Freund's incomplete adjuvant (FIA). Other adjuvants include olefin cross-linked unsaturated carboxylic acid polymers, such as cross-linked acrylic acid polymers. As used herein the term "cross-linked acrylic acid polymer" refers to polymer and copolymers formed from a monomer mixture which includes acrylic acid as the predominant monomer in the mixture. Examples of suitable cross-linked acrylic acid polymers include those commercially available under the tradenames Carbopol® 934P and Carbopol® 971 (available from B.F.Goodrich Co., Cleveland, Ohio).

The presently disclosed antibodies and antigen binding fragments thereof may be utilized in methods for monitoring the course of a disease associated with elevated levels of oxCaMKII in a subject. The methods may include evaluating the level of oxCaMKII in a series of biological samples obtained at different time points from a subject, where a change in the level of oxCaMKII over time may be utilized to characterize a disease in the subject. For example, an increase in the level of oxCaMKII over time may be indicative of progression of the disease, and a decrease in the level of oxCaMKII over time may indicate a regression of the disease.

The presently disclosed antibodies and antigen binding fragments thereof also may be utilized in methods for monitoring a therapeutic treatment of a disease associated with elevated levels of oxCaMKII. The methods may include evaluating the level of oxCaMKII in a series of biological samples obtained at different time points from a subject undergoing a therapeutic treatment for a disease associated with elevated levels of oxCaMKII, where a change in the level of oxCaMKII over time may be utilized to characterize aspects of the therapeutic treatment including efficacy and undesirable side effects. For example, a decrease in the level of oxCaMKII over time may indicate an effective therapeutic outcome. Alternative, an increase in the level of oxCaMKII over time may indicate negative or undesirable side effects associated with the therapy. For example, the disclosed methods are utilized to detect oxCaMKII in a biological sample from a patient where the patient has or is at risk for developing a disease or condition selected from a group consisting of a cardiac disease, cancer, premature aging, (atherosclerosis, Alzheimer's disease, or sepsis. The method further may include: (c) administering a therapeutic agent to the patient (or not administering a therapeutic agent to the patient) based on detecting oxCaMKII (or not detecting oxCaMKII) in the biological sample from the patient. With respect to the role of CaMKII in cardiac arrhythmia, reference is made to Erickson et al., "CaMKII and its role in cardiac arrhythmia," J. Cardiovas. Electrophysiol. 2008 December; 19(12): 1332-6, Epub 2008 September, the content of which is incorporated herein in its entirety.

ILLUSTRATIVE EMBODIMENTS

The following embodiments are illustrative and are not intended to limit the scope of the disclosed subject matter.

Embodiment 1

A purified antibody or antigen-binding fragment thereof that binds specifically to oxidized calcium/calmodulin-dependent protein kinase II (oxCaMKII).

Embodiment 2

The antibody or antigen-binding fragment thereof according to embodiment 1, wherein the antibody is a human, mouse, rat, guinea pig, rabbit, dog, cat, pig, goat, horse or cow antibody.

Embodiment 3

The antibody or antigen-binding fragment thereof according to embodiment 1, wherein the antibody is monoclonal.

Embodiment 4

The antibody or antigen-binding fragment thereof according to embodiment 1, wherein the antibody is polyclonal.

Embodiment 5

The antibody or antigen-binding fragment thereof according to embodiment 1, wherein the antibody is chimeric.

Embodiment 6

The antibody or antigen-binding fragment thereof according to embodiment 1, wherein the antibody is humanized.

Embodiment 7

The antibody or antigen-binding fragment thereof according to embodiment 1, wherein the antibody is a human antibody.

Embodiment 8

The antibody or antigen-binding fragment thereof according to embodiment 1, wherein the antigen binding fragment is an Fab fragment.

Embodiment 9

The antibody or antigen-binding fragment thereof according to embodiment 1, wherein the antigen binding fragment is an F(ab')$_2$ fragment.

Embodiment 10

The antibody or antigen-binding fragment thereof according to embodiment 1, wherein the antigen binding fragment is a dAb fragment.

Embodiment 11

The antibody or antigen-binding fragment thereof according to embodiment 1, wherein the antigen binding fragment is a single chain Fv.

Embodiment 12

The antibody or antigen-binding fragment thereof according to embodiment 1, wherein the antibody or antigen-binding fragment binds specifically to a peptide consisting of an amino acid sequence selected from the consensus amino acid sequence {S,C}{H,Q}RSTVAS{C,M}MHRQETV{D,E} (SEQ ID NO:4) in which the cysteine or methionine at position 9 is oxidized and the methionine at position 10 is oxidized.

Embodiment 13

The antibody or antigen-binding fragment thereof according to embodiment 1, wherein the antibody or antigen-binding fragment binds specifically to oxCaMKII delta having oxidized methionine residues at positions 281 and 282.

Embodiment 14

A labeled antibody or antigen-binding fragment thereof comprising the antibody or antigen-binding fragment thereof according to embodiment 1 and a label.

Embodiment 15

An isolated CaMKII polypeptide or an immunogenic fragment thereof, comprising oxidized methionine residues at amino acid positions 281 and 282.

Embodiment 16

A method of preparing antisera that binds specifically to oxCaMKII, the method comprising: (a) administering to an animal a composition comprising CaMKII or an immunogenic fragment thereof having one or more oxidized amino acids selected from a group consisting of oxidized methionine and oxidized cysteine; (b) and isolating antisera from the animal.

Embodiment 17

The method of embodiment 16, wherein the composition further comprises an adjuvant.

Embodiment 18

The method of embodiment 16, wherein the CaMKII or an immunogenic fragment thereof is prepared by a process comprising treating the CaMKII or an immunogenic fragment thereof with an oxidizing agent.

Embodiment 19

An isolated cell that produces antibody that binds specifically to oxCaMKII.

Embodiment 20

The isolated cell of embodiment 19, wherein the cell is a hybridoma or a plasmacytoma.

Embodiment 21

A method of detecting oxCaMKII, comprising: (a) contacting a biological sample from a patient with an antibody or antigen-binding fragment thereof that binds specifically to oxCaMKII and forms a complex; and (b) detecting the complex.

Embodiment 22

The method of embodiment 21, wherein the biological sample is blood or plasma.

Embodiment 23

The method of embodiment 21, further comprising: (c) characterizing heart disease in the patient.

Embodiment 24

The method of embodiment 21, wherein the patient has or is at risk for developing a disease or condition selected from a group consisting of a cardiac disease or condition, cancer, premature aging, atherosclerosis, Alzheimer's disease, or sepsis, and the method further comprises: (c) administering a therapeutic agent based on detecting or not detecting oxCaMKII.

Embodiment 25

The method of embodiment 21, wherein the patient is undergoing therapy with an angiotensin converting enzyme (ACE) inhibitor and the method further comprises: (c) modulating the therapy based on detecting or not detecting oxCaMKII.

Embodiment 26

The method of embodiment 25, wherein modulating the therapy comprises increasing dosage of the ACE inhibitor.

Embodiment 27

The method of embodiment 25, wherein modulating the therapy comprises decreasing dosage of the ACE inhibitor or ceasing the therapy.

Embodiment 28

The method of embodiment 21, wherein the patient is undergoing anti-cancer therapy and the method further comprises: (c) modulating the therapy based on detecting or not detecting oxCaMKII.

Embodiment 29

The method of embodiment 28, wherein the anti-cancer therapy is selected from a group consisting of radiation therapy, chemotherapy, nutritional therapy, and combinations thereof.

Embodiment 30

A kit for detecting oxCaMKII, comprising: (a) an antibody or antigen-binding fragment thereof that binds specifically to oxCaMKII to form a complex; and (b) a label for detecting the complex.

Embodiment 31

A method of treating or preventing structural heart disease in a patient comprising administering to the patient an antibody or antigen-binding fragment thereof that binds specifically to oxCaMKII.

Embodiment 32

The method of embodiment 31, wherein the antibody or antigen-binding fragment binds specifically to oxCaMKII delta having oxidized methionine residues at positions 281 and 282.

Embodiment 33

A pharmaceutical composition comprising: (a) an antibody or antigen-binding fragment thereof that binds specifically to oxCaMKII; and (b) a pharmaceutically acceptable carrier.

Embodiment 34

A method of treating or preventing structural heart disease in a patient comprising administering a therapeutic agent that specifically inhibits oxidation of calcium/calmodulin-dependent protein kinase II.

Embodiment 35

A method for treating or preventing structural heart disease in a patient comprising increasing methionine sulfoxide reductase activity in the patient.

EXAMPLES

The following Examples are illustrative and are not intended to limit the disclosed subject matter. The experiments were performed using the methodology described below. With respect to the following Examples, reference is made to Erickson e.g., "A dynamic pathway for calcium-independent activation of CaMKII by methionine oxidation," Cell, 2008 May 2; 133(3):397-9, the content of which is incorporated herein by reference in its entirety. Direct Oxidation Results in $Ca^{2+}$ Independent Activation of CaMKII," to be published in Cell, projected publication date of May 2, 2008.

Example I

Direct Oxidation Results in $Ca^{2+}$ Independent Activation of CaMKII

A. Summary

Calcium/calmodulin ($Ca^{2+}$/CaM)-dependent protein kinase II (CaMKII) couples increases in cellular $Ca^{2+}$ to fundamental responses in excitable cells. CaMKII was identified over twenty years ago by activation dependence on $Ca^{2+}$/CaM, but recent evidence shows CaMKII activity is also enhanced by pro-oxidant conditions. The data presented here demonstrates that oxidation of paired regulatory domain methionine residues sustains CaMKII activity in the absence of $Ca^{2+}$/CaM. CaMKII is activated by angiotensin II (AngII) induced oxidation, leading to apoptosis in cardiomyocytes, both in vitro and in vivo. CaMKII oxidation is reversed by methionine sulfoxide reductase A (MsrA), and $MsrA^{-/-}$ mice show exaggerated CaMKII oxidation and myocardial apoptosis, impaired cardiac function, and increased mortality after myocardial infarction. These data demonstrate a novel, dynamic mechanism for CaMKII activation by oxidation and highlight the critical importance of oxidation-dependent CaMKII activation to AngII and ischemic cardiac apoptosis.

B. Introduction

The multifunctional calcium/calmodulin ($Ca^{2+}$/CaM)-dependent protein kinase II (CaMKII) couples increases in $Ca^{2+}$ to activation of ion channels (Grueter e.g., 2006), gene transcription (Backs e.g., 2006), and apoptosis (Zhu e.g., 2003; Yang e.g., 2006). CaMKII is activated by enhanced intracellular $Ca^{2+}$ from beta-adrenergic receptor (βAR) stimulation (Zhang e.g., 2005). Excessive βAR stimulation causes apoptosis by a $Ca^{2+}$, CaMKII, and caspase-3 dependent pathway (Zhu e.g., 2003). The CaMKII holoenzyme is assembled from subunits containing three key domains: the association domain, which directs multimeric assembly, the regulatory domain, which controls enzyme activation and autoinhibition, and the catalytic domain, which performs the kinase function of CaMKII. Under resting conditions CaMKII is inactive, but upon binding $Ca^{2+}/CaM$ a conformational change relieves the autoinhibitory effect of the regulatory domain on the kinase domain, activating the enzyme (Hudmon and Schulman, 2002; Rosenberg e.g., 2005). In the sustained presence of $Ca^{2+}/CaM$, CaMKII undergoes intersubunit autophosphorylation at T287 (or 286; specific numbering is isoform dependent), resulting in $Ca^{2+}/CaM$ independent activity (Hudmon and Schulman, 2002). T287 lies within the autoinhibitory region of CaMKII, and autophosphorylation at T287 produces $Ca^{2+}$ autonomous activity by preventing re-association of the kinase domain by the autoinhibitory region (Hudmon and Schulman, 2002). Interconversion between $Ca^{2+}$-dependent and $Ca^{2+}$-independent forms is a critical property of CaMKII that allows transformation of a transient $Ca^{2+}$ stimulus into sustained physiological or disease-causing activity.

CaMKII activity may also increase in pro-oxidant cellular environments (Howe e.g., 2004; Zhu e.g., 2007), suggesting CaMKII has broader functionality than originally envisioned by connecting 'upstream' oxidant stress and $Ca^{2+}$ signals to 'downstream' cellular responses. Based upon the previously recognized structure-activity response of CaMKII to T287 phosphorylation, it was hypothesized that oxidation directly modifies the autoinhibitory motif to confer $Ca^{2+}/CaM$ independent CaMKII activity by a mechanism analogous to autophosphorylation. A novel direct molecular mechanism for reactive oxygen species (ROS)-dependent, $Ca^{2+}$ independent CaMKII activation by modification of M281/282 was identified. These findings show that direct activation of CaMKII by ROS engenders $Ca^{2+}$ autonomous activity, a clear but previously unrecognized molecular mechanism by which CaMKII can integrate $Ca^{2+}$ and ROS signals.

Elevated levels of ROS have been measured and contribute to adverse outcomes after myocardial infarction (Kinugawa e.g., 2000) and in models of heart failure (Maack e.g., 2003). Angiotensin II (AngII) also increases ROS in heart (Doerries e.g., 2007), while AngII antagonist drugs are a mainstay for reducing mortality in patients with structural heart disease (Pfeffer e.g., 1992; Pfeffer e.g., 2003). It was hypothesized that CaMKII is a downstream signal for ischemic and AngII stimulated apoptosis in heart and that CaMKII responses were dependent upon this newly identified M281/282 activation mechanism. Methionine sulfoxide reductase A (MsrA) specifically reverses Met oxidation, suggesting that $MsrA^{-/-}$ mice would show increased CaMKII oxidation after AngII and ischemic stress. The data presented here demonstrate that CaMKII inhibition protects against AngII initiated apoptosis in heart and that pathological AngII responses recruit CaMKII activity by M281/282 oxidation in vitro and in vivo. $MsrA^{-/-}$ mice show increased CaMKII oxidation and apoptosis with AngII and ischemia and increased mortality, greater left ventricular dilation and worse in vivo mechanical function after myocardial infarction, compared to controls. The data also establish CaMKII as a downstream signal for AngII and ischemic stress and establish ROS modification of CaMKII at M281/282 as a dynamic mechanism for regulating myocardial responses to common forms of heart disease.

C. Methods

1. Mouse Models

Mice lacking the p47 gene ($p47^{-/-}$) were purchased from Jackson Labs. Mice lacking the MsrA ($MsrA^{-/-}$) were supplied by NIH (Bethesda, Md.). Mice with genetic CaMKII inhibition (AC3-I) were generated by us as previously described (Zhang e.g., 2005).

2. CaMKII Activity Assays and Protein Analysis

Mutant CaMKII cDNAs were generated using a QuikChange site-directed mutagenesis kit (Stratagene). CaMKIIδ (GenBank #NP_001020609) was generated using the Bac-to-Bac baculovirus system (Invitrogen) and purified on a calmodulin-agarose column. For CaMKII activity assays, purified CaMKII was pretreated with 200 μM $CaCl_2$ and 1 μM CaM on ice for 1 minute. The protein was then exposed to ATP, $H_2O_2$, or water at the described concentrations for 10 minutes. Samples exposed to ATP or $H_2O_2$ were then treated with 10 mM EGTA for 10 minutes. CaMKII activity was measured as a function of $^{32}P$-ATP incorporation into a synthetic substrate (syntide-2) at 30° C., as previously described (Wu e.g., 2002).

3. Oxidized M281/282 Immune Serum Production and Immune Staining

Antigenic peptide with the sequence CQRSTVASMM-HRQETVD (SEQ ID NO:5) (Epitomics, Inc.) was generated and exposed to 100 μM $H_2O_2$ for one hour. Rabbits were immunized and antiserum titer was monitored using standard ELISA procedures. Antiserum was collected after 75 and 96 days. Commercial antibodies were used for blots and immunostaining for total (Stressgen Biotechnologies) and phosphorylated (Santa Cruz) CaMKII.

4. Detection of ROS

Changes in ROS levels in cultured primary cardiac myocytes after agonist stimulation were measured using the fluorogenic probe dihydroethidium (DHE, 5 μM, Molecular Probes), as previously described (Zimmerman e.g., 2004). DHE fluorescent images were acquired using confocal microscopy (Zeiss LSM510).

5. Intracellular Calcium Concentration Measurements

Intracellular calcium concentration was assessed by Fura-2 fluorescence ratio imaging using a microscopic digital imaging system (Photon Technology International), as described previously (Sharma e.g., 1995). Briefly, cultured primary cardiac myocytes were loaded with the $Ca^{2+}$-specific dye Fura-2 by incubating with 1 μM Fura-2AM (Molecular Probes) at 37° C. for 30 minutes. $[Ca^{2+}]_i$ values over the entire cell were calculated from the 340/380-nm ratio images of Fura-2 fluorescence captured before, during and after Iso (100 nM) or AngII (100 nM) stimulation.

6. Fluorescence Measurements

Spectra were collected at 30° C. using a Fluorolog 3 (Jobin Yvon, Horiba) spectrofluorometer. For intrinsic fluorescence shift experiments, excitation wavelength was 270 nm. Emission spectra were generated at 1 nm increments from 280 nm to 400 nm. Background traces were subtracted from CaMKII spectra to eliminate the contribution from intrinsic fluorescence of CaM. For fluorescence anisotropy experiments, baseline traces of 100 nM dansylated CaM in 15 mM HEPES buffer, pH 7.2 were measured at baseline and after the addition of 200 μM $CaCl_2$ at 60 s. At 180 s, 100 nM purified CaMKII was added to the CaM solution. For some trials, CaMKII became phosphorylated by the addition of 10 mM ATP. 100 μM $H_2O_2$ or an equivalent volume of buffer was added at 250 s. Finally, addition of 10 mM EGTA at 300 s was used to remove free calcium from the solution, uncoupling CaM/CaMKII binding.

7. Cardiomyocyte TUNEL Immunostaining

Figure 12:
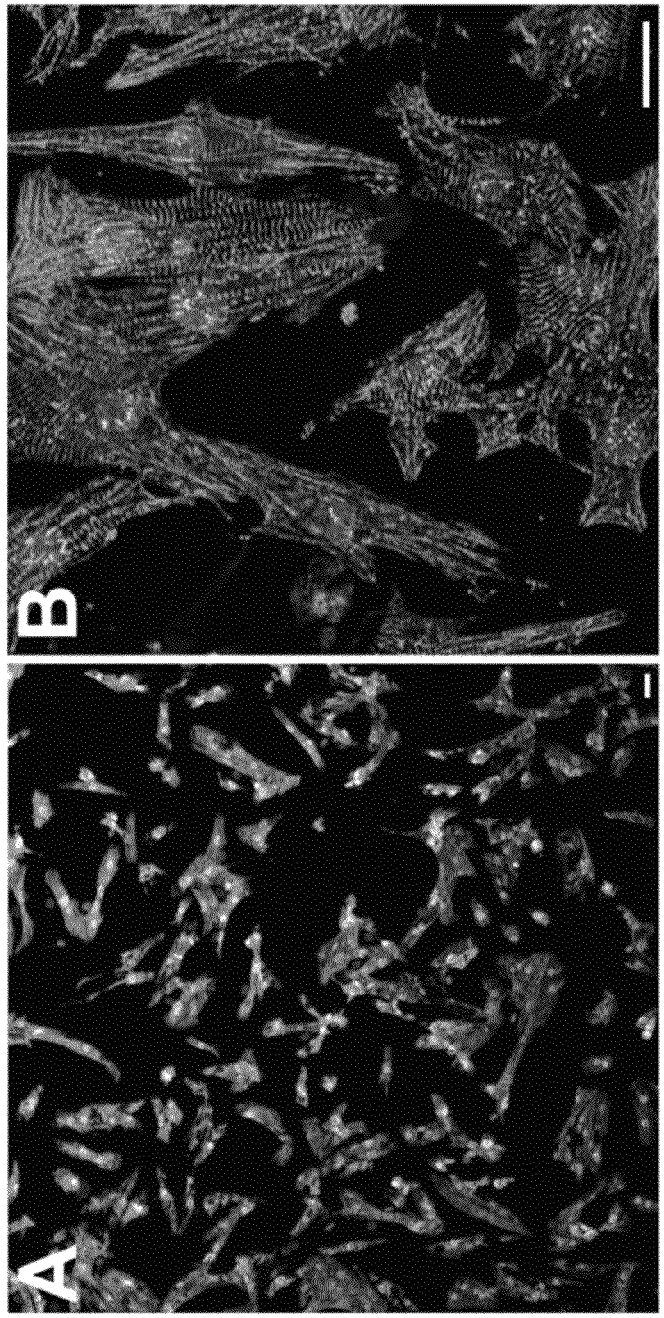
FIG. 12. The identity of cultured neonatal mouse cardiomyocytes is confirmed by confocal microscopy after immunostaining. Green stain is α-actinin and purple stain is nuclei. Over 90% of nuclei fall clearly within striated cardiomyocytes. Calibration bars are 20 μm.

Myocyte isolations from neonatal mouse or rat pups were modified from previously described methods (Mohler e.g., 2007). To generate the primary cardiomyocyte cultures, hearts were dissected from P1 animals and placed in 1 mL of Ham's F-10. Atrial tissue was removed and the ventricular chambers were rinsed to remove any remaining blood. Hearts were transferred into 1.5 mL of 0.05% Trypsin, 200 µM EDTA in Ham's F-10 medium (Mediatech). Hearts were minced into approximately 20 small pieces using forceps and small scissors and incubated in the Trypsin/EDTA medium at 37° C. Following 15 min, the heart pieces were mixed by a Pasteur pipette and incubated for an additional 15 min. A mixture of 200 µL of soybean trypsin inhibitor (2 mg/mL; Worthington) and 200 µL of collagenase (0.2 mg/mL; 1980 units/mg; Sigma) was incubated with the cells for 35-50 min at 37° C. The cell suspension was pelleted, resuspended in "Complete Medium" (40% DMEM, 40% Ham's F-10, 20% FCS), and plated on plastic dishes. Following five hours, the non-adhered cells (cardiomyocytes) were aspirated from the plate, pelleted, resuspended in Complete Medium, and plated on Mattek tissue culture plates (fibronectin-coated; Roche). Cardiomyocytes were washed with Ham's F-10 and Medium was replaced with "Defined Medium" to prevent the growth of fibroblasts. 100× Defined Medium consists of 100 µg/mL insulin, 500 µg/mL transferrin, 100 nM LiCl, 100 nM $NaSeO_4$, and 10 nM thyroxine. To ensure that pure populations of cardiomyocytes were obtained, cultures were immunolabeled with alpha-actinin Ig (cardiomyocyte-specific marker). Only cultures with >90% cardiomyocytes were used in experiments. (See FIG. 12.) Lentiviral treatments (shRNA, rescue constructs) and apoptosis inducing agents (Iso, AngII) were used for 24 hours. Cells were fixed in 4% paraformaldehyde, permeabilized in 0.1% Triton X-100 and sodium citrate, and stained using In Situ cell death detection kits, TMR Red (Roche). TUNEL stain assays were interpreted as previously described (Yang e.g., 2006). Nuclei were co-stained with DAPI. Investigators were blinded to the genetic identity and treatment of the mice in all studies.

8. shRNA Targets and CaMKII cDNA Constructs

The CaMKIIδ-specific shRNA target sequence was selected based on the algorithm of Chalk, Wahlestedt, and Sonnhammer and others (Hammond e.g., 2000; Bernstein e.g., 2001; Brummelkamp e.g., 2002). Five target sequences were tested and the most effective target shRNA was used for experiments in this manuscript (CaMKIIδ 920-938 CUAUGCUGGCUACGAGAAA (SEQ ID NO:6)). Sense and anti-sense sequences were created and ligated into a modified pFIV lentiviral vector (SBI). For rescue experiments, full-length rat CaMKIIδ was cloned into pCDH1-MCS1-EF1-copGFP (SBI) and completely sequenced. The resulting construct was then modified to be shRNA resistant by engineering conserved residue wobble base changes at four positions in the template (CTG[A]-GCT[C]-ACG[A]-AGA[G] (SEQ ID NO:7))→LATR to LATR. The resulting construct was then fully re-sequenced. The fidelity of the viral knock-down and rescue construct were confirmed in primary cardiomyocytes.

9. Virus Generation

The most efficacious shRNA construct was engineered into the pFIV lentiviral vector and packaged into viral pseudoparticles using the System Biosciences viral packaging kit (SBI LV100A-1). Specifically the constructs were co-transfected with packaging plasmid mix from the kit into HEK293 FT cells using Effectene anionic lipid transfection reagent. After 16 hours the serum free media was changed to fresh DMEM with 10% FBS and 1% penicillin/streptomycin. 48 hours later the pseudoparticle containing supernatant was concentrated using Amicon Centriplus YM-30 columns spun at 2500×g for 3 hours at 4° C. The concentrate was then dispensed into 200 µl aliquots and stored at −80° C. Experiments were done with cells cultured 48 hours after infection.

10. Heart Section TUNEL Immunostaining

Figure 13:
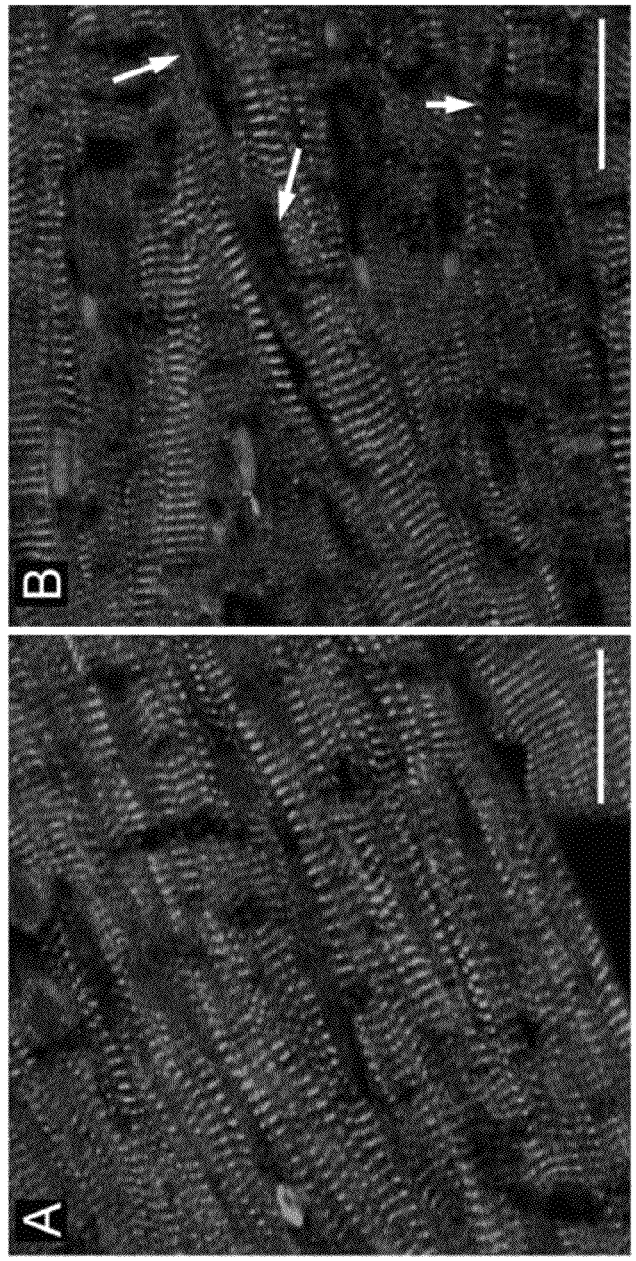
FIG. 13. The identity of cardiomyocytes from mouse heart sections is confirmed by confocal microscopy after immunostaining. (A) Green stain is α-actinin and blue stain is nuclei. (B) Green stain is α-actinin and red stain is TUNEL. Over 90% of nuclei fall clearly within striated cardiomyocytes. Calibration bars are 20 μm.

Mice were anesthetized with ketamine (87.5 mg/kg) and xylazine (12.5 mg/kg), and a small incision was made in the skin near the spine, approximately 1 cm above the hip. Minipumps containing saline or AngII (3 mg/kg/day) were inserted and the skin was sutured closed. Other mice were given daily injections of Iso (30 mg/kg/day, intraperitoneal) for 7 days. Animals were then sacrificed and the heart was removed, fixed, and embedded in paraffin. Transverse heart sections of 5 µm thickness were made. To confirm the identity of cardiomyocytes, heart sections were immunolabeled with alpha-actinin Ig (cardiomyocyte-specific marker). Only sections with >90% cardiomyocytes were used in experiments. (See FIG. 13.) Paraffin was removed, and TUNEL staining was performed using In Situ cell death detection kits, TMR Red (Roche). Nuclei were co-stained with DAPI. To determine percent of TUNEL positive nuclei, whole heart sections were divided into four quadrants and one image was taken at random within each quadrant. In the case of sections from post-MI mice, an average of 50% of the heart quadrants were from portions of the heart adjacent to the MI. An investigator blinded to the identity and treatment of the mice counted the number of total and TUNEL positive cells in each image.

Other sections were treated with either a general CaMKII antibody or oxidized CaMKII antiserum. Nuclei were co-stained with DAPI. Identity of cardiomyocytes was confirmed by co-stain with an antibody against α-actinin. Images were quantified for relative staining intensity using Image J (NIH, USA). Each image was divided into four quadrants, and one rectangular area of equal size and shape was randomly placed within the cytosolic area of each quadrant, excluding DAPI-stained nuclei. Relative intensity of an image was judged to be the mean of the intensity measurements taken in each quadrant. Both the investigators and technical personnel assigned to immunostaining and quantification were blinded to the genetic identity and treatment of the mice in all studies.

11. Myocardial Infarction and Echocardiography

Mice were anesthetized with ketamine/xylazine (87.5/12.5 mg/kg, respectively). Mice were then intubated and ventilated with room air (150 µl tidal volume, 120 breaths/min). An incision was made in the $3^{rd}$ intercostal space, and the ribs were retracted to expose the heart. The pericardial sac was opened, and the left anterior descending (LAD) branch of the coronary artery was ligated using 8-0 ethilon suture (Ethicon) along the anterolateral border of the heart as close to the left atrial appendage as possible. Successful ligation of the artery is confirmed by blanching of the myocardium. A chest tube was inserted into the thorax, and the muscle and skin were sutured closed around the tube to form a seal. Negative pressure was applied to reduce the pneumothorax. Mice were then extubated.

Transthoracic echocardiograms were recorded in conscious sedated mice as described previously (Weiss e.g., 2006), using a 15 MHz probe connected to a Sonos 5500 imager (Phillips Medical Systems, Bothell, Wash.) at a frame rate of 180-200 frames per second. Images were acquired by an operator blinded to mouse genotype and were analyzed off-line using custom-designed software (Freeland Medical Systems, Louisville, Colo.).

12. Cysteine Protection and Ellman's Reagent Assays

CaMKII was pretreated with 10 mM iodoacetic acid to block oxidation of available cysteine residues. Activity was determined as described in main text. To test the efficacy of cysteine residue blockage, a colorometric assay was performed with or without iodoacetic acid. Samples of CaMKII were incubated with Ellman's reagent (benzoic acid, Pierce)

for 15 minutes, and the absorbance was measured at 412 nm in a spectrophotometer. Molar ratios of available cysteine residues were determined by comparing to a standard curve of purified cysteine samples. Control experiments were performed with a peptide known to contain exactly one cysteine.

13. LC-MS-MS Analysis and Protein Identification

The synthetic peptide CQRSTVASMMHRQETVD (SEQ ID NO:5), with and without $H_2O_2$ treatment, was subjected to in solution trypsin digestion. LC-MS-MS analysis of the resulting peptides was performed using a Thermo Finnigan LTQ ion trap mass spectrometer as previously described (Greeter e.g., 2006) except that the mass spectrometer was equipped with a Thermo MicroAS autosampler and the peptides were separated on a packed capillary tip with C18 resin (Jupiter $C_{18}$, 5 micron, 300 angstrom, Phenomonex, Torrance, Calif.) using an inline solid phase extraction column that was 100 μm×4 cm packed with the same C18 resin using a frit generated with liquid silicate Kasil 1. The mass spectrometer was tuned prior to analysis using the synthetic peptide TpepK (AVAGKAGAR (SEQ ID NO:8)). Typical tune parameters were as follows: spray voltage of between 1.8 KV, a capillary temperature of 150° C., a capillary voltage of 50V and tube lens 100V. One full MS scan from 400-2000 m/z was acquired followed by the acquisition of MS/MS scans in a targeted fashion collecting MS/MS spectra for the doubly charged version of the STVASMMHR peptide (SEQ ID NO:1) (510.24 m/z) and it's corresponding oxidized species (518.24, 526.24, 534.24, 542.24 m/z). Fragment ion traces were extracted for each m/z value utilizing the $y_5$ and $y_6$ ions for relative quantification experiments. MS/MS spectra were collected using an isolation width of 3 m/z, an activation time of 30 ms, and activation Q of 0.250 and 30% normalized collision energy using 1 microscan and maximum injection time of 100 for each scan. For the relative quantification experiments, targeted MS/MS analyses of three normalization peptides, LLKHPNIVR (SEQ ID NO:9), GAFSVVR (SEQ ID NO:10) and IPTGQEYAAK (SEQ ID NO:11) (363.89, 368.21 and 539.28 m/z, respectively) in the same run as the methionine containing peptides were performed. Fragment ion traces for the normalization peptides were extracted utilizing the four most abundant ions (two most abundant ions for GAFSVVR) in each spectrum that were either b- or y-ions. The peptides were quantified by extracting the fragment ion traces, integrating the peaks in Xcalibur to obtain peak area for both the methionine containing peptides and the normalization peptides. Once the peak areas were extracted, the methionine containing peptides were normalized by dividing the peak area by each of the normalization peptides and then taking the ratio of each of these normalized signals in the treated vs. non-treated samples. The ratios for each of the normalized signals were then averaged for each replicate analysis.

14. Caspase-3 Activity Assays

Cells were lysed in assay lysis buffer (50 mM Tris-HCl pH 7.5, 100 mM KCl, 1 mM EDTA, 1 mM EGTA, 1 mM DTT, 0.1 mM PMSF, 0.5 mM benzamidine, 20 mg/L leupeptin, 1 μM microcystin, 20 mM sodium pyrophosphate, 50 mM NaF, and 50 mM sodium β-glycerophosphate) and total protein content was determined by Biuret assay. Caspase-3 activity was determined by Enz-Chek Caspase-3 kit (Invitrogen).

15. Statistical Analysis

Statistical significance for mortality study was determined by chi-squares test. All other statistical significance was determined by One-Way ANOVA with post hoc Bonferonni tests. A p value of <0.05 was considered statistically significant. All results are presented as mean±SEM.

D. Results

1. Oxidation Directly Activates CaMKII

CaMKII is activated by $Ca^{2+}$/CaM, but autophosphorylation at T287 sustains catalytic activity after dissociation of $Ca^{2+}$/CaM (FIG. 1A) because the negatively charged phosphate prevents reassociation of the catalytic domain and autoinhibitory region (Hudmon and Schulman, 2002). CaMKII activity may also be enhanced by pro-oxidant conditions (Zhu e.g., 2007); it therefore was hypothesized that oxidation of the regulatory domain in the vicinity of T287 could sustain CaMKII catalytic activity by an analogous mechanism. Exposure of purified CaMKII to $H_2O_2$ in the absence of any pretreatment yielded no discernable CaMKII activity (FIG. 1B). However, exposure to $H_2O_2$ after pretreatment with $Ca^{2+}$/CaM yielded persistent CaMKII activation even in the presence of EGTA. These data suggest that $Ca^{2+}$/CaM binding exposed a key segment of CaMKII for oxidation, and that oxidation interfered with the interaction of the autoinhibitory and catalytic domains. Activation of wild type (WT) CaMKII by $H_2O_2$ was dose-dependent (FIG. 1C). The concentration of EGTA used was sufficient to block CaMKII activity without the addition of $H_2O_2$ (FIG. 1B), suggesting that activity observed in the pro-oxidant condition was independent of sustained $Ca^{2+}$/CaM binding.

Figure 2:
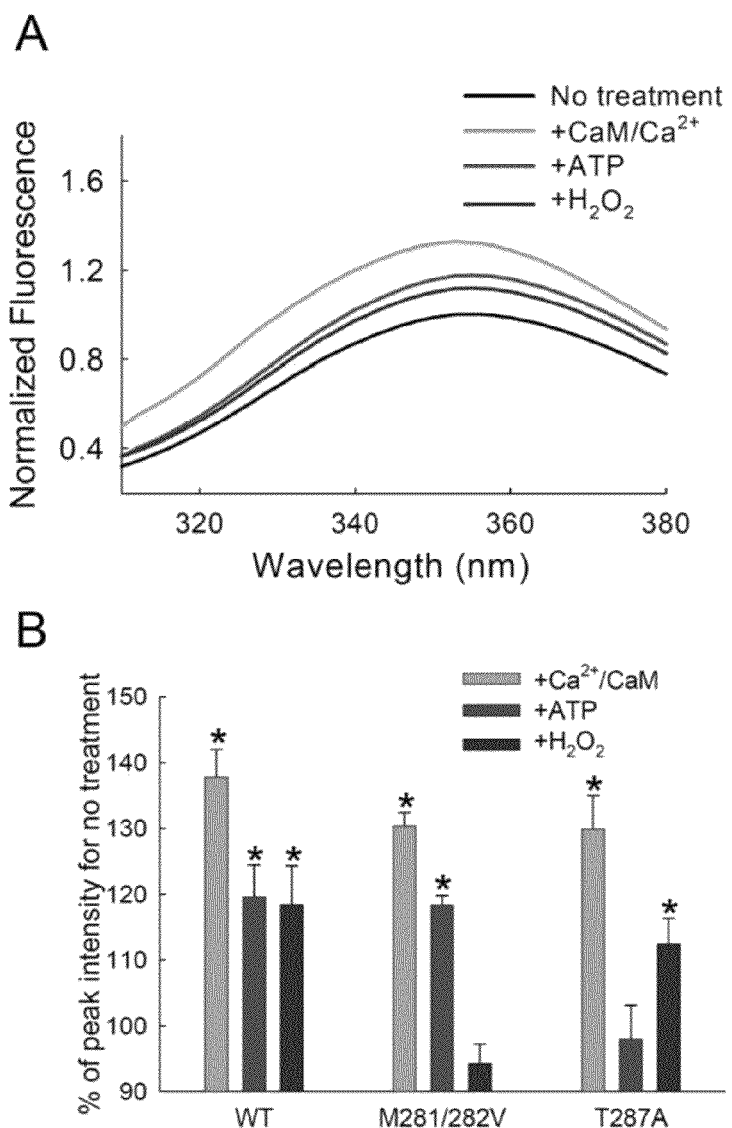
FIG. 2. Oxidation and autophosphorylation of CaMKII are associated with similar fluorescence shifts. (A) Sample emission fluorescence spectra of WT CaMKII after no treatment or in the presence of $Ca^{2+}$/CaM, ATP, or $H_2O_2$. No significant difference among CaMKII mutants for peak fluorescence with no treatment was observed (n=3 assays/group, not shown). (B) M281/282V CaMKII mutants do not show a shift in emission fluorescence intensity at peak fluorescence after treatment with 100 μM $H_2O_2$ (n=3 assays/group, * p<0.05 vs. WT no treatment). Response to $Ca^{2+}$/CaM and ATP activation are unchanged.

Pretreatment with $Ca^{2+}$/CaM was also necessary for autophosphorylation-dependent CaMKII activation, indicating that autophosphorylation and oxidation of CaMKII occur by parallel mechanisms. CaMKII bearing a T287A substitution underwent normal $Ca^{2+}$/CaM-dependent activation but did not maintain persistent $Ca^{2+}$-independent activity in the presence of ATP (FIG. 1D). However, the T287A mutant was activated by $H_2O_2$ (FIG. 1C), and the extent of this activation was statistically indistinguishable at all but the highest concentration of $H_2O_2$ tested (1 μM). These observations are interpreted as evidence that activation of CaMKII by ROS and autophosphorylation occur by a similar mechanism, but by independent modifications to nearby sites. Activation of the kinase by either mechanism requires the enzyme to be initially 'opened' by $Ca^{2+}$/CaM to allow access to the autoinhibitory domain for oxidation or autophosphorylation (FIG. 1A, E). Either of these modifications can prevent subsequent interaction of the autoinhibitory region with the catalytic domain, providing for sustained $Ca^{2+}$-independent activation of CaMKII. Consistent with these ideas, direct measurements of intrinsic fluorescence revealed that autophosphorylation and oxidation of CaMKII independently induce similar conformational changes in CaMKII. (See FIG. 2).

2. Chromatographic Analysis of CaMKII and M281/282V Mutant After Treatment with ATP or $H_2O_2$ Proteomic analysis of the synthetic peptide that contains the 281/282 methionine residues was used to probe for oxidative modification upon treatment with $H_2O_2$. Because an internal standard was not available, the change in oxidation with the synthetic peptide was not quantified. To compensate, the peptides for MS/MS fragmentation were targeted throughout the run. The number of spectra observed for a peptide or protein previously has been shown to be correlate with peptide and protein levels (Liu e.g., 2004). By targeting the peptides, multiple spectra across each peak were observed. Based on the chromatographic traces and on the change in the number of observed spectra, a clear decrease in the unoxidized form coupled with an increase in the various oxidized forms of this peptide was observed. (Data not shown). The MS/MS fragmentation spectra were verified by manual inspection of the SEQUEST results.

In addition to the synthetic peptide, the peptide containing the 281/282 methionine residues was analyzed after treatment of the whole protein with $H_2O_2$ followed by trypsin cleavage. To better quantify the change in the oxidation, several other unmodified tryptic peptides produced from the digestion (LLKHPNIVR (SEQ ID NO:9), GAFSVVR (SEQ ID NO: 10) and IPTGQEYAAK (SEQ ID NO:11)) were assessed to normalize the signal. The m/z values then were targeted throughout the chromatogram; fragment ion traces for a pseudo-MRM trace were extracted; and the peak area of the oxidized peptide to the normalizing peptides were compared to normalize the signal. By taking the ratio of the normalized signals, the relative change in oxidation of this peptide upon hydrogen peroxide treatment was determined. (See Tables 1 & 2).

TABLE 1

Oxidation of synthetic peptide methionines upon $H_2O_2$ treatment and trypsin digestion.

| Peptide | Spectral counts[a] | |
|---|---|---|
| | Untreated | $H_2O_2$ treated |
| STVASMMHR | 41 | 3 |
| STVASMMHR + 1 Oxygen | 13 | 0 |
| STVASMMHR + 2 Oxygen | 0 | 3 |
| STVASMMHR + 3 Oxygen | 0 | 52 |
| STVASMMHR + 4 Oxygen | 0 | 6 |

[a]Spectral counts are the number of times the spectrum for the corresponding peptide was observed after filtration criteria were applied as described in Methods.

TABLE 2

Oxidation of tryptically digested methionine-containing peptides after $H_2O_2$ treatment of intact protein.

| Peptide | Relative Change[a] |
|---|---|
| STVASMMHR | 0.36 ± 0.06 |
| STVASMMHR + 1 Oxygen | 6.4 ± 1.9 |
| STVASMMHR + 2 Oxygen | 115 ± 25 |
| STVASMMHR + 3 Oxygen | NQ[b] |
| STVASMMHR + 4 Oxygen | NO[c] |

[a]Relative change was calculated as described in the methods and is reported as average ± standard deviation from three replicate analyses.
[b]Observed in $H_2O_2$ treated sample, absent in control sample, so not quantified
[c]Not observed.

The MS/MS spectra of the oxidized forms of the peptide were identical to those from the synthetic peptide, verifying that the oxidized peptide was correctly identified. In addition to an increase in both singly and doubly oxidized forms of this peptide, a triply oxidized peptide in the $H_2O_2$-treated protein that was absent in the untreated protein MS/MS spectrum was observed. Because there was an absence of this peptide in the untreated sample, the relative increase in the triply oxidized peptide was not calculated.

Figure 3:
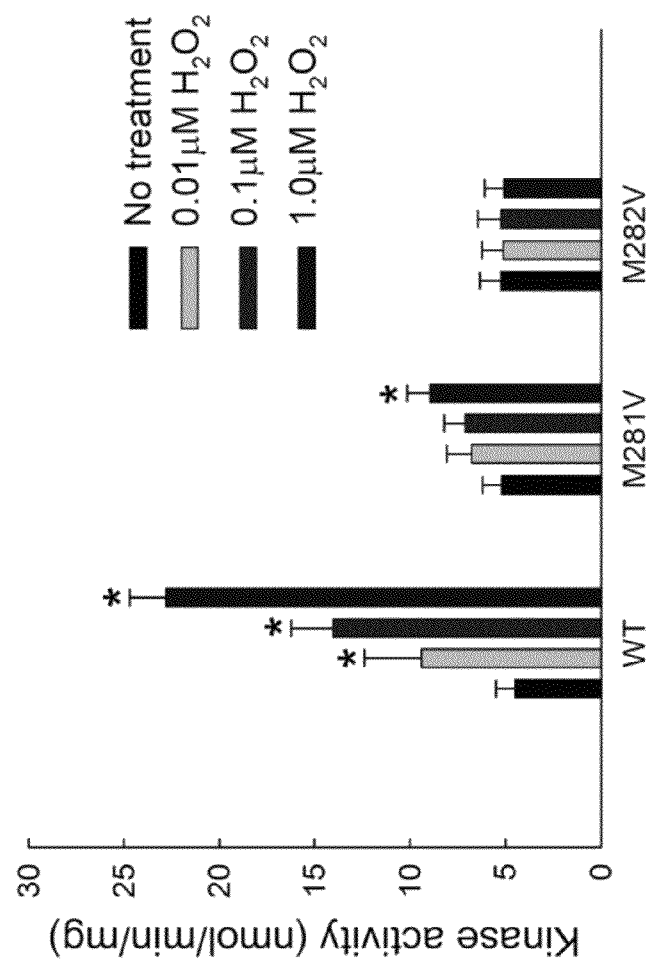
FIG. 3. ROS-dependent activity is ablated by M281V or M282V point mutation. Wild type CaMKII shows increased activity in response to $H_2O_2$ treatment, while this dose dependent activation is not seen in the M281V and M282V mutants. (n=3 assays/group, * p<0.05 vs. WT no treatment)

3. Mutant Forms of CaMKII that are Resistant to Activation by Oxidative Treatment Given these observations and the recognized susceptibility of methionine residues to oxidation (Hoshi and Heinemann, 2001), mutants having methionine to valine substitutions for the paired residues (M281/2/32V) and for another methionine (M308V) in the CaM-binding region were created. These mutants were exposed to $H_2O_2$ and assayed for activity in the presence of EGTA (FIG. 1C). The $H_2O_2$-dependent activation of CaMKII was preserved in the M308V mutant. However, oxidation-dependent CaMKII activity was completely abolished in the M281/282V and M281/282/308V mutants. These data, obtained in cell free assay conditions, point to direct oxidation of the M281/282 pair as the primary $H_2O_2$-dependent activation pathway for CaMKII. Importantly, all the methionine to valine mutants showed a normal activity response to autophosphorylation (FIG. 1D), further supporting the concept that $Ca^{2+}$ autonomous CaMKII activation by ROS or T287 autophosphorylation are independent events. While the paired methionine motif is conserved in the β, γ, and δ isoforms of CaMKII, the neuronal a isoform substitutes a cysteine residue for the first methionine of the pair (position 280 in CaMKIIα). The side chain of cysteine is also susceptible to oxidation. A M281C mutant of CaMKIIδ was generated to mimic the substitution in CaMKIIα. Additionally, CaMKIIα was generated and purified. Both the M281C CaMKIIδ mutant and the purified CaMKIIα were activated by $H_2O_2$, indicating that the cysteine substitution seen in CaMKIIα also supports ROS-dependent activation (FIG. 1C). To further elucidate the role of M281 and M282 in ROS-dependent activation, these sites were individually mutated. (See FIG. 3.) The M282V mutation completely ablated oxidation-dependent activation, while the M281V mutation partially reduced activation by 65%, indicating that a single oxidation event within the regulatory domain is insufficient to activate CaMKII.

Figure 4:
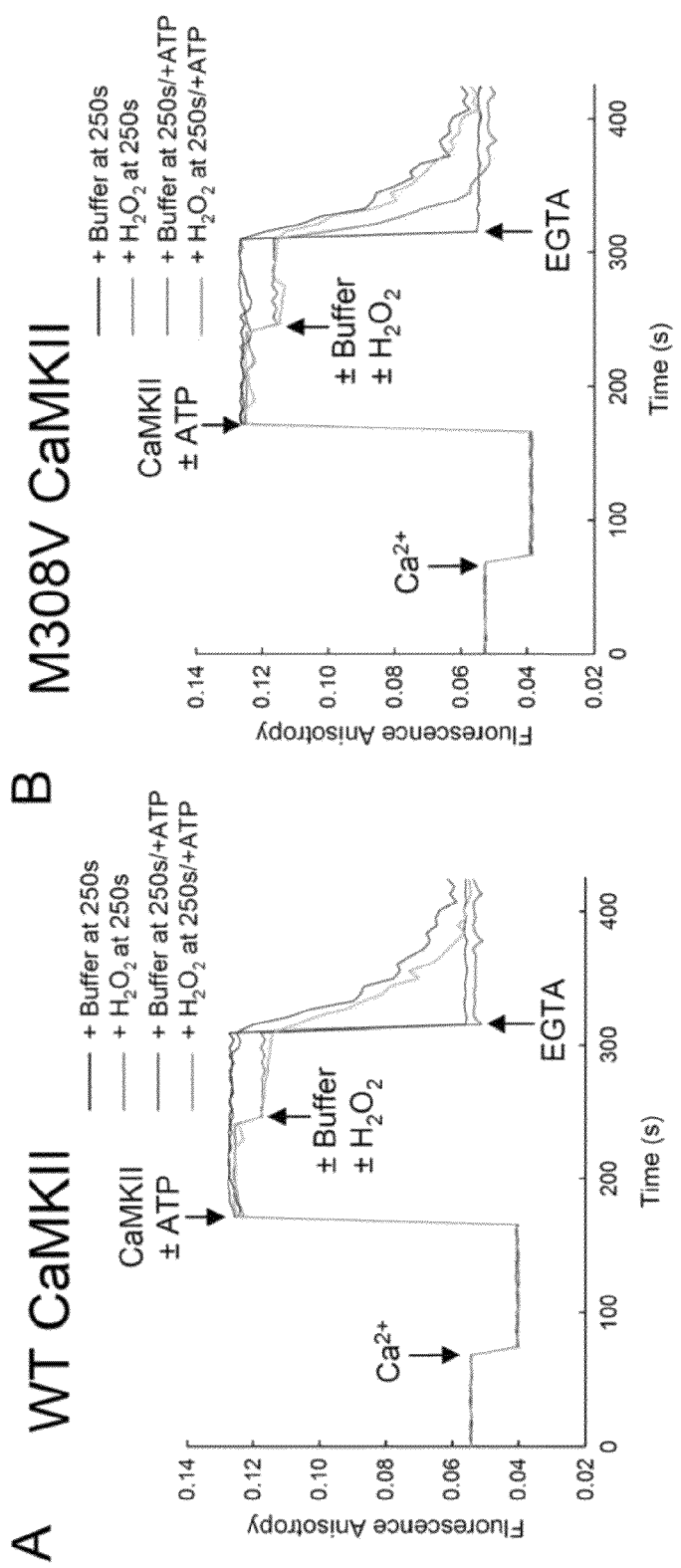
FIG. 4. Oxidation of CaMKII does not initiate CaM trapping during ROS-dependent CaMKII activation. (A) Real time fluorescence anisotropy measurement of CaM after the addition of $CaCl_2$, CaMKII, and EGTA (black line). Addition of $H_2O_2$ prior to EGTA (red line) does not result in CaM trapping. CaM trapping is seen when ATP is present (blue and green lines). (B) In contrast to WT CaMKII, an M308V mutant shows slowed $Ca^{2+}$/CaM/CaMKII dissociation after treatment with $H_2O_2$. (C) Half time to baseline fluorescence after addition of EGTA for $Ca^{2+}$/CaM/CaMKII dissociation with WT or M308V CaMKII (n=3 trials/group, * p<0.05 vs. half time for CaMKII in buffer only). (D) Pretreatment of CaMKII with iodoacetic acid blocks cysteine oxidation but does not affect ROS-dependent activity. Mutation of C290 does not affect CaMKII activity responses to $H_2O_2$.
Figure 4:
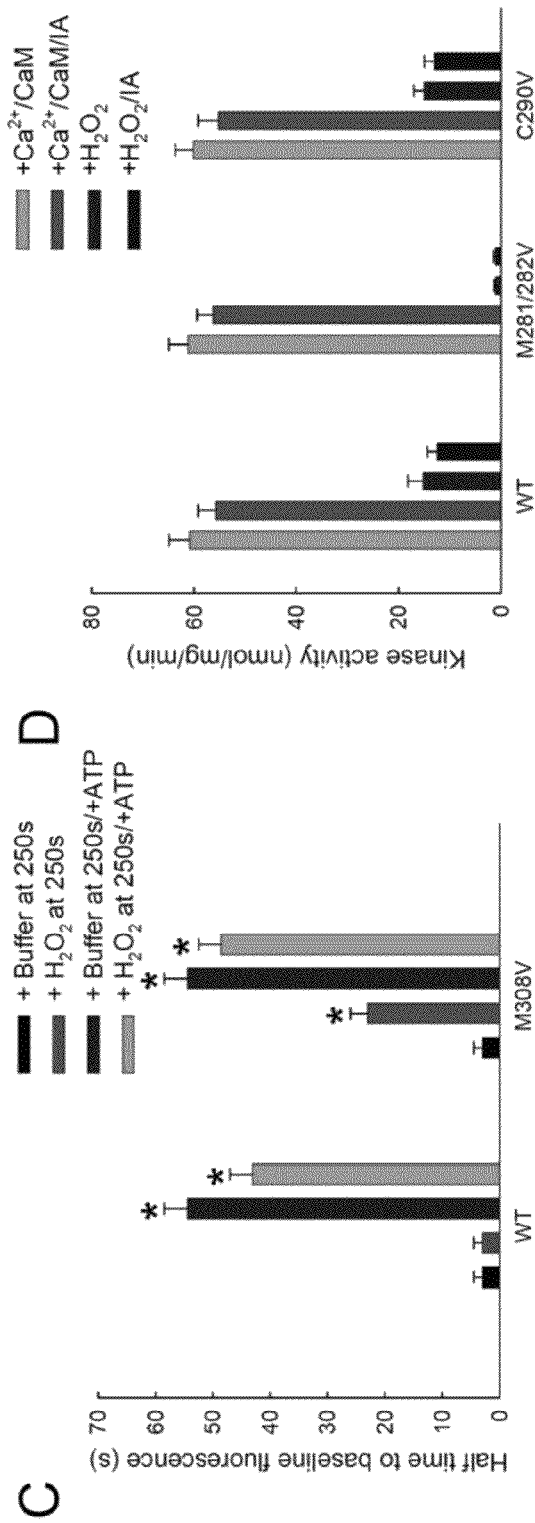

Autophosphorylation at T287 dramatically increases the binding affinity of CaMKII for CaM, a phenomenon known as "CaM trapping" (Meyer e.g., 1992). In the absence of ATP the $Ca^{2+}$/CaM/CaMKII complex was very rapidly dissociated following addition of EGTA, independent of the redox state, as measured by fluorescence anisotropy of dansylated CaM. (See FIG. 4A.) CaMKII exposure to $H_2O_2$ for 10 min induced $Ca^{2+}$/CaM-independent activity (as in FIG. 1B), but also failed to induce CaM trapping (not shown). These observations indicate that under normal experimental conditions, oxidation of CaMKII is not sufficient to induce CaM trapping. Dissociation of $Ca^{2+}$/CaM from autophosphorylated CaMKII and CaM was significantly slower than from non-phosphorylated enzyme, consistent with CaM trapping. However, pretreatment with $H_2O_2$ prior to EGTA had no significant effect on the dissociation kinetics. Thus, oxidation of CaM or CaMKII does not prevent or enhance CaM trapping by autophosphorylated CaMKII. CaM trapping is reduced by phosphorylation of T306/307 (Colbran 1993), suggesting that oxidation of M308 might prevent CaM trapping by a parallel mechanism. A significant slowing of dissociation of the CaM/CaMKII complex after $H_2O_2$ treatment of the M308 mutant was observed. (See FIGS. 4B, C.) These data suggest that the absence of CaM trapping during oxidation is partly due to M308.

It seemed possible that conditions capable of oxidizing methionine residues would also oxidize unprotected cysteine residues. Although mutation of methionine residues at 281 and 282 was sufficient to completely ablate ROS-dependent activation of CaMKII, a C290V mutant was created to determine whether this cysteine residue within the CaMKII regulatory domain could also play a role. Both the $Ca^{2+}$/CaM-dependent and ROS-dependent activity of the C290V mutant were indistinguishable from WT CaMKII. (See FIG. 4D.) This finding that oxidation of paired amino acids (M281/282 in CaMKIIδ) were required for activation by $H_2O_2$ support a view that oxidation of a lone residue is insufficient to confer $Ca^{2+}$/CaM autonomous CaMKII activity. In order to comprehensively test the potential role of all accessible cysteines in contributing to oxidation-dependent CaMKII activity, CaMKII activity responses to $H_2O_2$ in the presence of iodoacetic acid were measured. Iodoacetic acid is a reagent that blocks oxidation of unprotected cysteine residues (Zangerle e.g., 1992). Cysteine protected CaMKIIδ showed equivalent $H_2O_2$ activity responses compared to CaMKIIδ without iodoacetic acid. (Data not shown.) An established colorometric assay was used to quantify the available cysteine residues and verify that cysteine protection by iodoacetic acid was effective. These results confirmed that most or all of the 11 cysteines in CaMKIIδ were accessible to the Ellman's reagent after $Ca^{2+}$/CaM binding, while treatment with iodoacetic acid blocked the accessibility of cysteine residues to biochemical modification (data not shown). Taken together, these findings demonstrate that oxidative activation of CaMKIIδ is independent of cysteines.

4. Oxidation of CaMKII Occurs In Vivo

Figure 5:
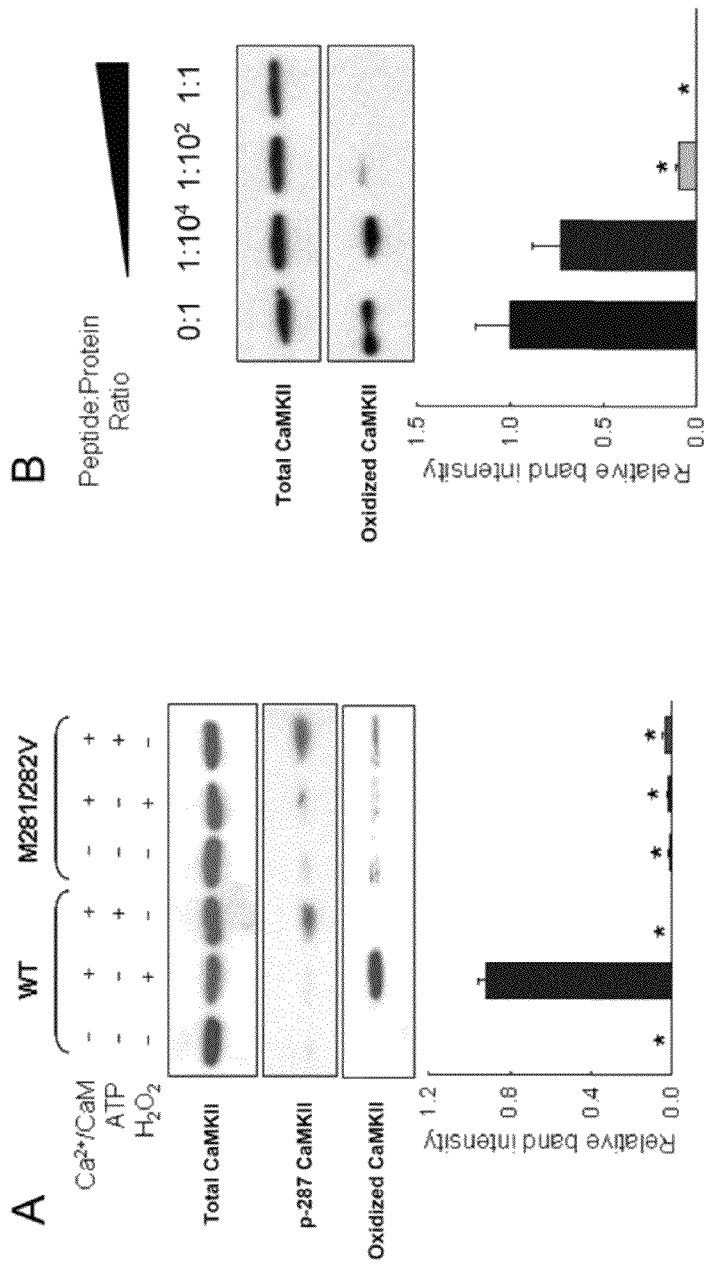
FIG. 5. AngII induces oxidation of CaMII in vivo. (A) Immunoblot of WT CaMKII and M281/282V mutant after no treatment, oxidation, or autophosphorylation probed with antibodies against total, autophosphorylated (p-T287), or oxidized CaMKII. Summary data shows relative band intensity using the oxidized CaMKII antibody (n=3 trials/group, * p<0.05 vs. band intensity of WT CaMKII treated with $H_2O_2$). (B) Immunoblot and summary data of oxidized WT CaMKII probed with antiserum against oxidized M281/282 with increasing ratios of oxidized antigen peptide. (n=3 trials/group, * p<0.05 vs. band intensity with no peptide). (C) Immunofluorescent staining of heart sections from mice treated with saline, AngII, or Iso and probed for oxidized or total CaMKII. Red staining is positive for oxidized or total CaMKII and blue staining is for nuclei. Calibration bars are 100 microns. (D) Immunoblot and summary data of heart lysates from mice treated with saline (Sal), Iso, or AngII probed with antibodies against total CaMKII, oxidized CaMKII, or actin (n=3 hearts/group, * p<0.05 vs. band intensity of saline treatment).
Figure 5:
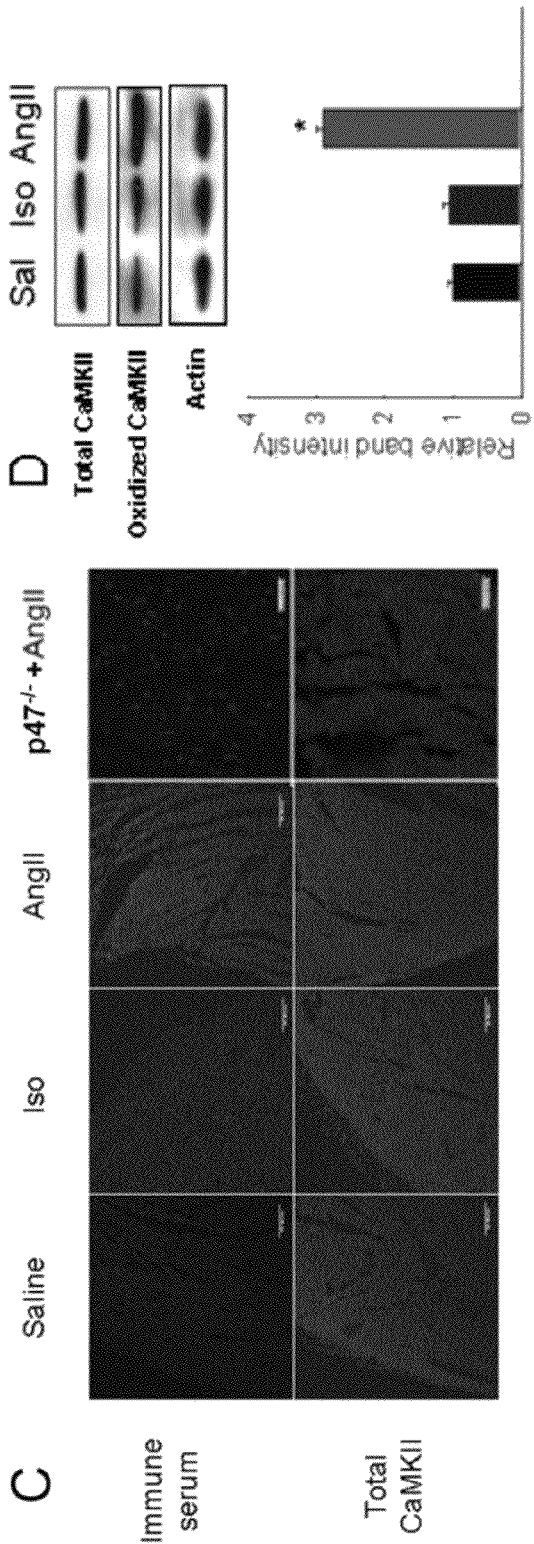

A new immune serum against oxidized M281/282 was prepared to detect ROS effects on CaMKII in vivo. The fidelity of the antiserum was validated using purified CaMKII protein by immunoblotting against WT CaMKII and the M281/282V mutant in control conditions and after treatment with $H_2O_2$ or $Ca^{2+}$/CaM/ATP. Blots were also assayed with a phospho- and site-specific antibody against T287 (p-287). WT CaMKII exposed to $H_2O_2$ after pretreatment with $Ca^{2+}$/CaM showed significant reactivity to oxidized M281/282 antiserum, but untreated and T287-phosphorylated CaMKII samples were not recognized by this antiserum. (See FIG. 5A). The M281/282V mutant had minimal reactivity to this antiserum among the three treatments. These findings demonstrated that phospho-T287 and oxidized M281/282 were immunologically distinct sites. Additional immunoblots were performed in which oxidized CaMKII was probed with the antiserum along with increasing concentrations of the peptide antigen (FIG. 5B). Band intensity decreased with increasing peptide concentration, indicating that the immune serum was specific for oxidized CaMKII.

To determine the role of CaMKII oxidation in apoptosis, mice were treated with saline, AngII, or isoproterenol (Iso) for one week, and transverse heart sections from these mice were probed for the production of oxidized CaMKII in vivo. WT mice treated with AngII produced more oxidized CaMKII than those treated with saline or Iso (FIG. 5C). Total CaMKII immunoreactivity remained constant regardless of treatment. Conversely, mice lacking a critical subunit of NADPH oxidase (p47$^{-/-}$) did not show increased levels of oxidized CaMKII in response to AngII. The p47$^{-/-}$ mice do not assemble the ROS-producing complex NADPH oxidase (Munzel and Keaney, 2001), the main source of ROS due to AngII stimulation in many cell types (Lyle and Griendling, 2006). Heart sections from WT mice showed increased staining for T287-phosphorylated CaMKII after AngII treatment, while p47$^{-/-}$ mice were unaffected. (See FIG. 6). Other studies have suggested that protein phosphatase activity is decreased by pro-oxidant conditions (Howe e.g., 2004), indicating the possibility of coordinate activation of CaMKII both by direct oxidation at the Met281/282 sites and by phosphatase inactivation leading to increased phosphorylation at the T287 site.

Homogenized hearts from mice treated with saline, AngII, or Iso, and whole heart lysates were analyzed by immunoblot for oxidized CaMKII. While total CaMKII was not significantly different among the three treatment groups, heart lysates from mice treated with AngII showed significantly increased oxidized CaMKII levels (FIG. 5D). Taken together, these findings demonstrate that oxidation of CaMKII occurs in vivo, and that elevated levels of AngII increase CaMKII oxidation at M281/282 compared to saline or Iso.

Figure 6:
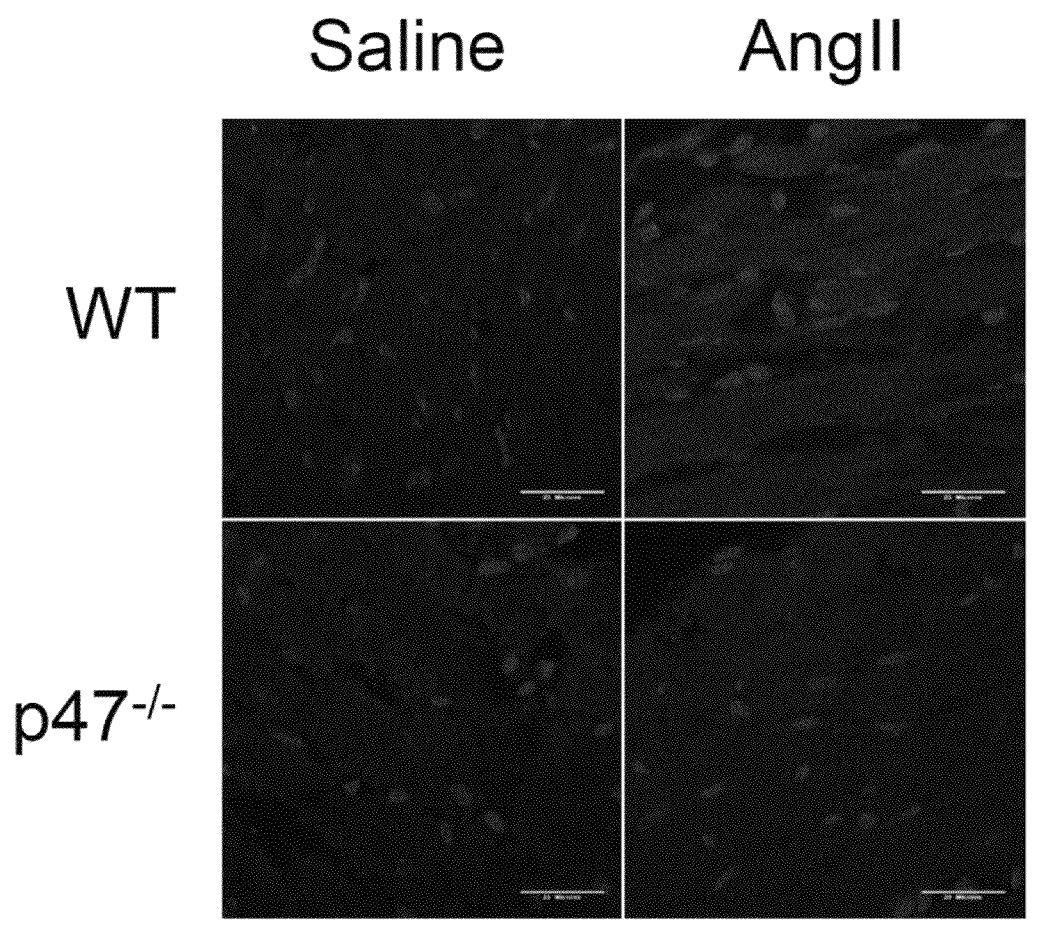
Figure 7:
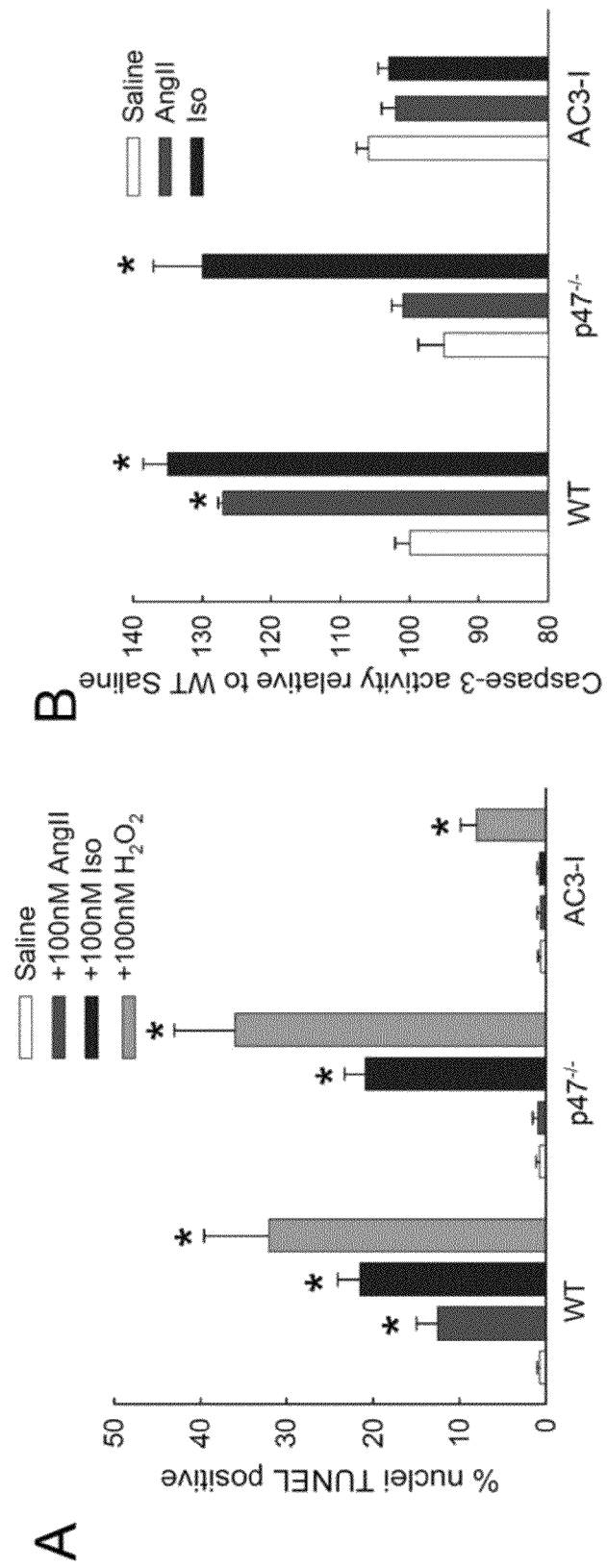
FIG. 7. AngII increases ROS production and apoptosis by a CaMKII-dependent pathway in cardiomyocytes. (A) Percent of total isolated cardiomyocytes positive for TUNEL staining after treatment with saline, AngII, Iso, or $H_2O_2$ (n=6 hearts/group, * p<0.05 vs. WT with saline). (B) Caspase-3 activity induced by saline, AngII, or Iso normalized to WT cells treated with saline (n=3 hearts/group, * p<0.05 vs. WT with saline). (C) DHE stained cardiomyocytes after treatment with 100 nM AngII or Iso. Red coloration indicates presence of ROS above control cells. Scale bars equal 50 μm. (D) Percent of total cells positive for DHE staining above control (n=3 assays/group, * p<0.05 vs. WT saline). (E) Example traces of intracellular calcium concentration of cultured WT cardiomyocytes treated with 100 nM AngII (red symbols) or Iso (blue symbols) measured by real-time calcium imaging. The arrow indicates addition of AngII or Iso. (F) Peak intracellular $Ca^{2+}$ concentration in response to either AngII or Iso for WT or p47$^{-/-}$ cells (n=3 trials/group, NS=not statistically different).
Figure 7:
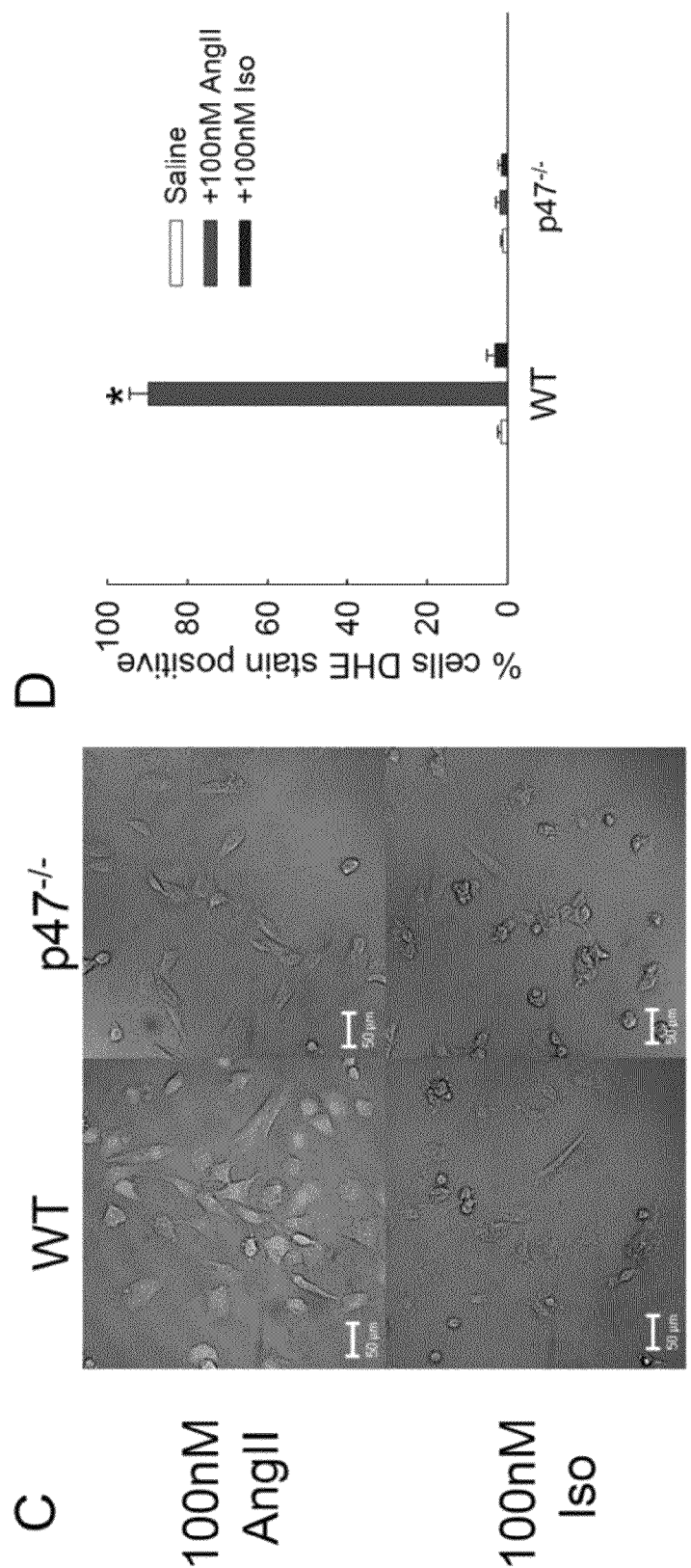
Figure 7:
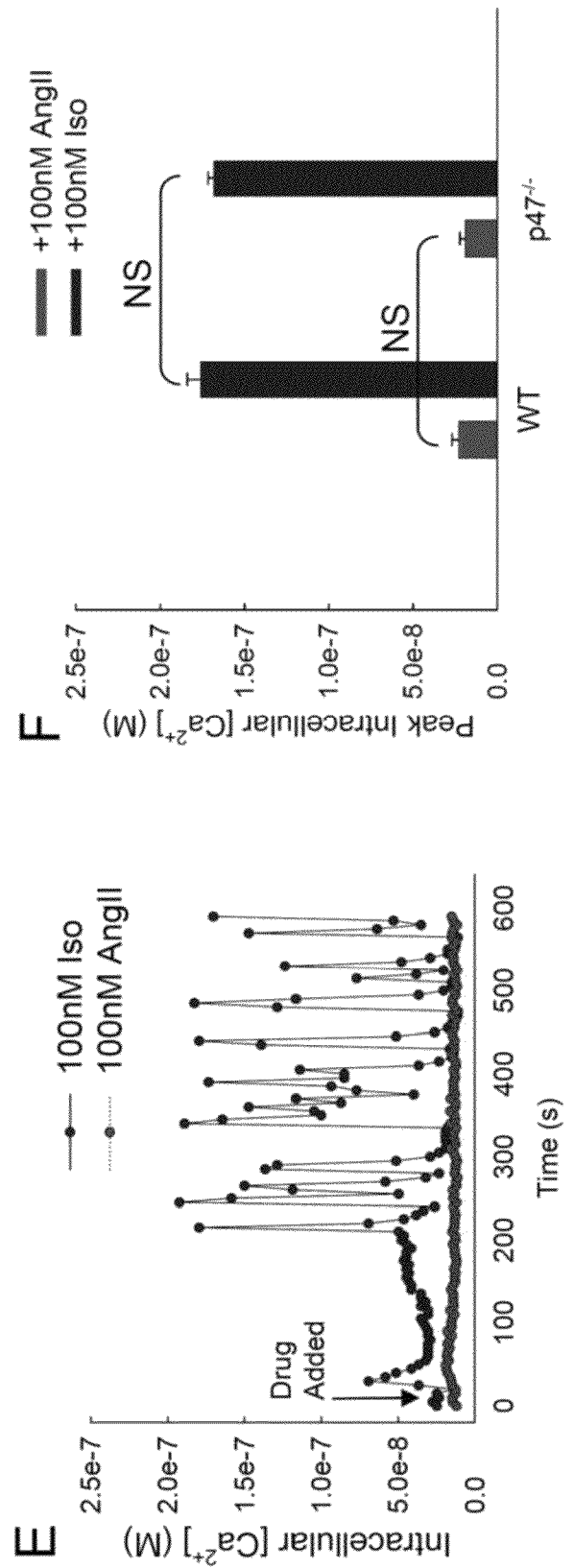

5. AngII Triggers ROS Production and CaMKII-Dependent Apoptosis in Cardiomyocytes Given these results, it was hypothesized that cells deficient in ROS production or CaMKII activity would be resistant to AngII mediated apoptosis. Cardiomyocytes from mice that express an inhibitory peptide against CaMKII (AC3-I, Zhang e.g., 2005) were treated with 100 nM AngII for 24 hours in parallel with isolated cardiomyocytes from WT and p47$^{-/-}$ mice. AngII caused a significant increase in the percent of TUNEL positive nuclei in WT cells but had no significant effect in p47$^{-/-}$ or AC3-I cardiomyocytes (FIG. 6). Activity assays for caspase-3, a downstream target enzyme in the CaMKII apoptotic signaling pathway in heart, recapitulated the results from the TUNEL assay (FIG. 7A). Importantly, direct addition of ROS in the form of $H_2O_2$ caused significant apoptosis in p47$^{-/-}$ cells, demonstrating that their resistance to AngII-induced apoptosis is a result of impaired ability to produce ROS rather than a lack of sensitivity to ROS. The apoptotic effect of $H_2O_2$ in AC3-I cells was blunted by more than half compared to WT or p47$^{-/-}$ cells (FIG. 7A), indicating the critical importance of CaMKII activation to ROS and Iso-dependent apoptosis.

In order to validate the connection between AngII and ROS in this experimental model, isolated cardiomyocytes from WT and p47$^{-/-}$ mice were treated with 100 nM AngII and monitored production of ROS by imaging DHE, a fluorescent reporter for superoxide and hydrogen peroxide (FIG. 7C). Wild-type cardiomyocytes were incubated with fura-2 AM, a cell-permeant calcium indicator to observe changes in intracellular $Ca^{2+}$ ($[Ca^{2+}]_i$). Treatment with AngII caused a significant increase in ROS production in WT but not in p47$^{-/-}$ cardiomyocytes (FIG. 7D). On the other hand, increases in $[Ca^{2+}]_i$ were significantly less after AngII compared to Iso treatment (FIG. 7E, F) for cardiomyocytes from both WT and p47 mice. These data show AngII signaling predominantly increases ROS, while Iso predominantly increases $[Ca^{2+}]_i$ under these experimental conditions.

6. CaMKII Knockdown Prevents AngII- and Iso-Induced Apoptosis

Figure 8:
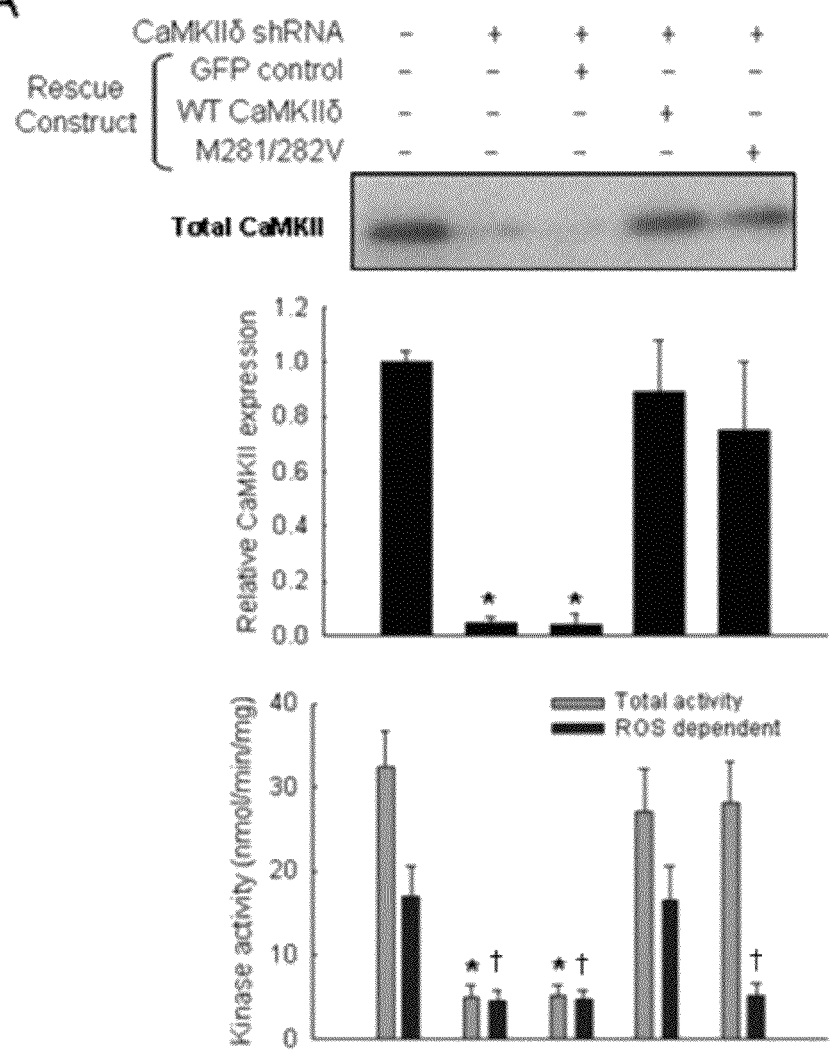
FIG. 8. AngII-induced apoptosis is blocked by CaMKII silencing. (A) Representative immunoblot with anti-CaMKII to measure protein expression after treatment with shRNA and shRNA-resistant rescue constructs. Immunoblot against actin was used as a loading control (not shown). Middle panel shows summary data of CaMKII expression relative to untreated cells (n=3 experiments/group, * p<0.05 vs. no treatment). Bottom panel shows summary data for CaMKII activity assays of lysates (n=3 experiments/group, * p<0.05 vs. total activity with no treatment, † p<0.05 vs. ROS-dependent activity with no treatment). Only the WT CaMKII construct was able to reconstitute both $Ca^{2+}$/CaM- and ROS-dependent activity observed in untreated cells. (B) Immunostaining and (C) summary data from isolated rat cardiomyocytes transduced with shRNA against CaMKII followed by rescue with WT CaMKII, M281/282V, or GFP control. Immunostaining shows total nuclei (DAPI) and DNA nicking (TUNEL) consistent with apoptosis. Scale bars equal 100 μm. Summary data show percent of total nuclei with positive TUNEL staining (n=6 hearts/group, * p<0.05 vs. GFP with AngII).

In order to further test the role of CaMKII and specifically define the effects of M281/282 on myocardial apoptosis, a knock down and replacement strategy in cultured neonatal cardiomyocytes was utilized. Rat cardiomyocytes were cultured and treated with shRNA encoding lentivirus against rat CaMKIIδ. After 48 hours CaMKII expression was significantly reduced, as measured by immunoblot and activity assays (FIG. 8A). Cells were then transduced with lentivirus encoding shRNA-resistant WT or M281/282V mutant CaMKII. Control cells were transduced with GFP encoding lentivirus. After 48 hours, cells transduced with CaMKII rescue constructs showed significant recovery of CaMKII expression compared to control cells. Addition of $Ca^{2+}$/CaM to lysates from cells transduced with either CaMKII encoding virus had similar total activity as native cells. However, $H_2O_2$-induced activity was only rescued in cells expressing the WT CaMKII construct. These cellular studies support this earlier finding with molecular CaMKII (FIG. 1) by showing that oxidation of M281/282 is critical for ROS triggered CaMKII activity. In addition, this strategy created cardiomyocytes expressing ROS-resistant CaMKII, providing a novel system for investigating ROS and CaMKII-dependent apoptosis.

Cardiomyocytes treated with shRNAs/CaMKIIδ encoding lentivirus were exposed to saline, AngII or Iso as above (FIG. 8B). The apoptotic response to AngII and Iso was significantly attenuated in CaMKII knockdown cells compared to myocytes without shRNA. Moreover, expression of shRNA-resistant WT CaMKII fully rescued apoptotic responses to both agonists (FIG. 8C). In contrast, expression of the ROS-resistant M281/282V CaMKII mutant rescued the apoptotic response to Iso but, importantly, failed to rescue the apoptotic response to AngII after 24 hours (FIG. 8C). Cells expressing the M281/282V CaMKII remain susceptible to Iso-induced apoptosis (FIG. 8B, C), indicating that elimination of these residues does not affect activation of CaMKII by catecholamine stimulation. These cellular studies are performed in a complex biological environment compared to studies with isolated CaMKII, but nevertheless support a concept that direct oxidation of CaMKII by AngII is sufficient to confer enhanced CaMKII activity and trigger apoptosis.

Figure 9:
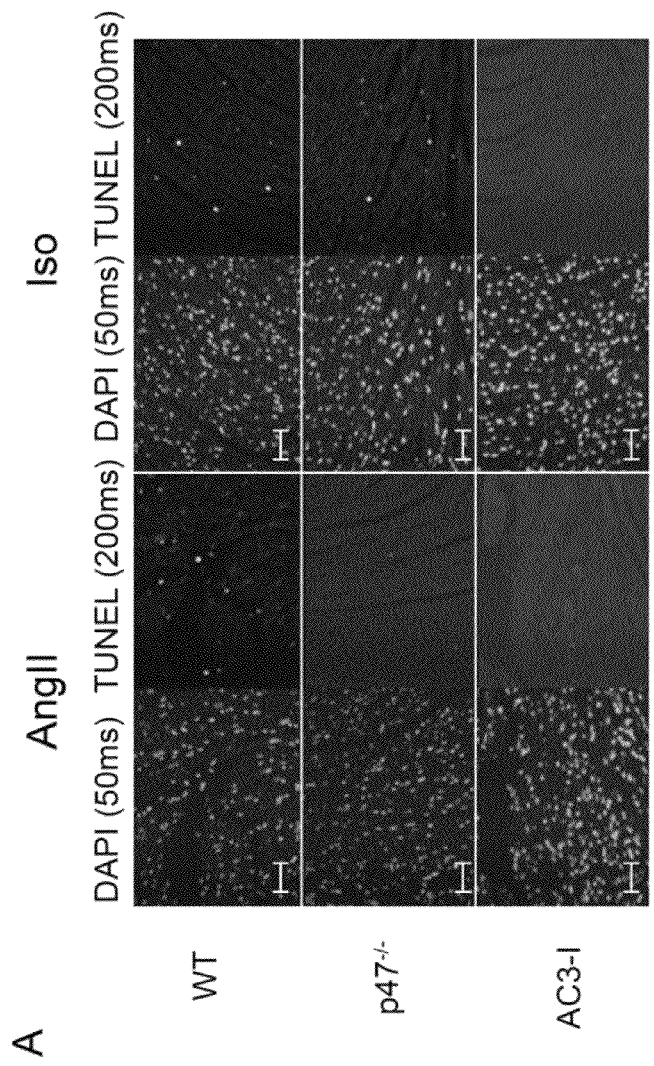
FIG. 9. AngII causes cardiac apoptosis in vivo via a ROS and CaMKII-mediated pathway. (A) Immunostaining of mouse heart sections for total nuclei (DAPI) and nuclear damage (TUNEL) consistent with apoptosis. WT, p47$^{-/-}$, and AC3-I mice were treated with Ang II (3 mg/kg/day) or Iso (30 mg/kg/day) for seven days. Scale bars equal 100 μm. (B) Percent of total nuclei that showed positive TUNEL staining (n=3 hearts/group, * p<0.05 vs. WT with saline).
Figure 9:
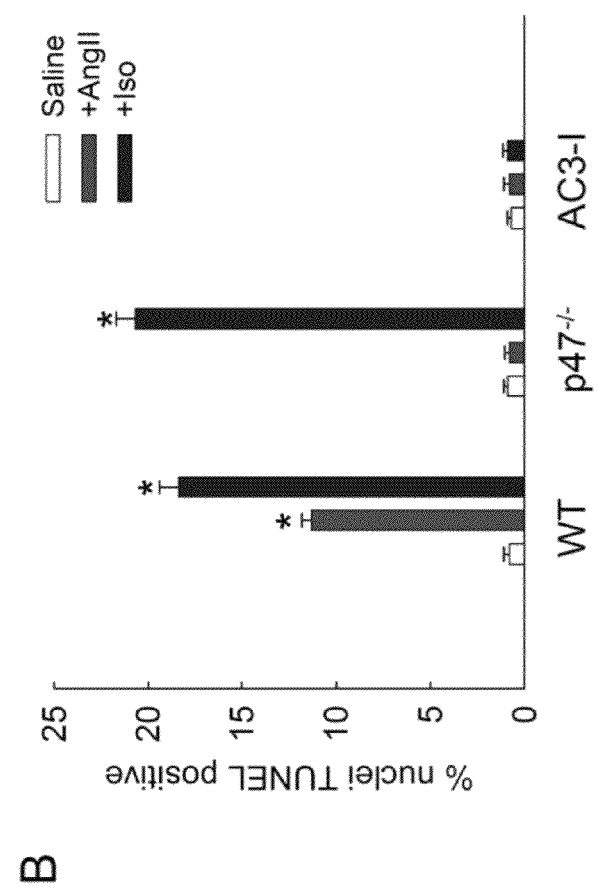

7. ROS Production and CaMKII Activity are Critical for AngII-Mediated Cardiac Apoptosis In Vivo Intracellular ROS levels increase dramatically in models of structural heart disease (Hare, 2001), particularly those initiated by AngII (Tojo e.g., 2002). Stimulation by AngII leads to activation of the NADPH oxidase complex, increasing intracellular superoxide and hydrogen peroxide levels. To establish an in vivo context for these previous findings and to test the role of CaMKII in AngII-stimulated cardiac apoptosis, $p47^{-/-}$, AC3-I, and WT mice were treated with saline, AngII or Iso for one week. Transverse heart sections from these mice were stained for evidence of apoptosis. After one week WT mice treated with either AngII or Iso showed significant cardiac apoptosis, as determined by TUNEL staining of heart sections (FIG. 9). The $p47^{-/-}$ mice had no significant increase in cardiac apoptosis after treatment with AngII, most likely because these mice were unable to produce ROS in response to AngII stimulation (FIG. 7D). However, the $p47^{-/-}$ mice showed a preserved apoptotic response to Iso, suggesting that Iso-induced apoptosis occurs independently of oxidative stress generated by NADPH oxidase in vivo under these conditions. In contrast, the AC3-I mice with CaMKII inhibition were resistant to apoptosis induced by either AngII or Iso, indicating that CaMKII is a necessary signal element for apoptosis initiated by AngII or Iso in vivo.

Figure 10:
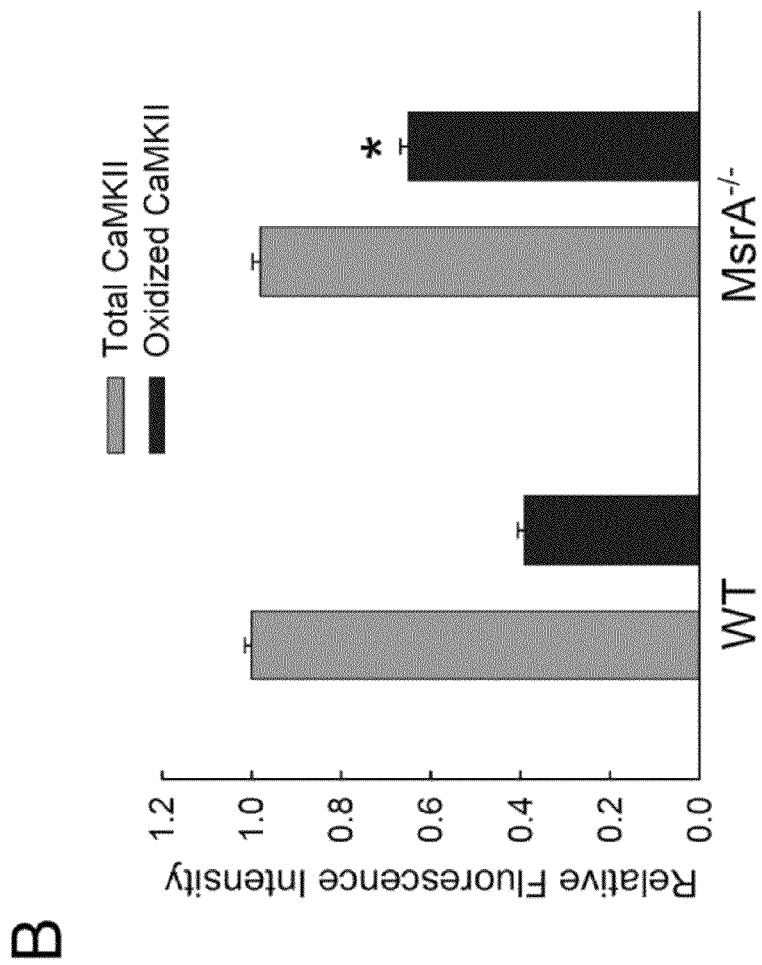
FIG. 10. MsrA$^{-/-}$ mice have increased susceptibility to AngII-mediated apoptosis. (A) Immunofluorescent staining of heart sections from WT and MsrA$^{-/-}$ mice treated with AngII and probed for oxidized or total CaMKII. Red staining is positive for oxidized or total CaMKII and blue staining is for nuclei. Calibration bars are 100 microns, (B) Quantification of average staining intensity for AngII treated hearts, relative to WT (n=3 hearts/group, * p<0.05 vs. WT with AngII). (C) Summary data for TUNEL staining of heart sections from WT and MsrA$^{-/-}$ mice treated with saline or AngII (n=5 hearts/group, * p<0.05 vs. WT with saline).
Figure 11:
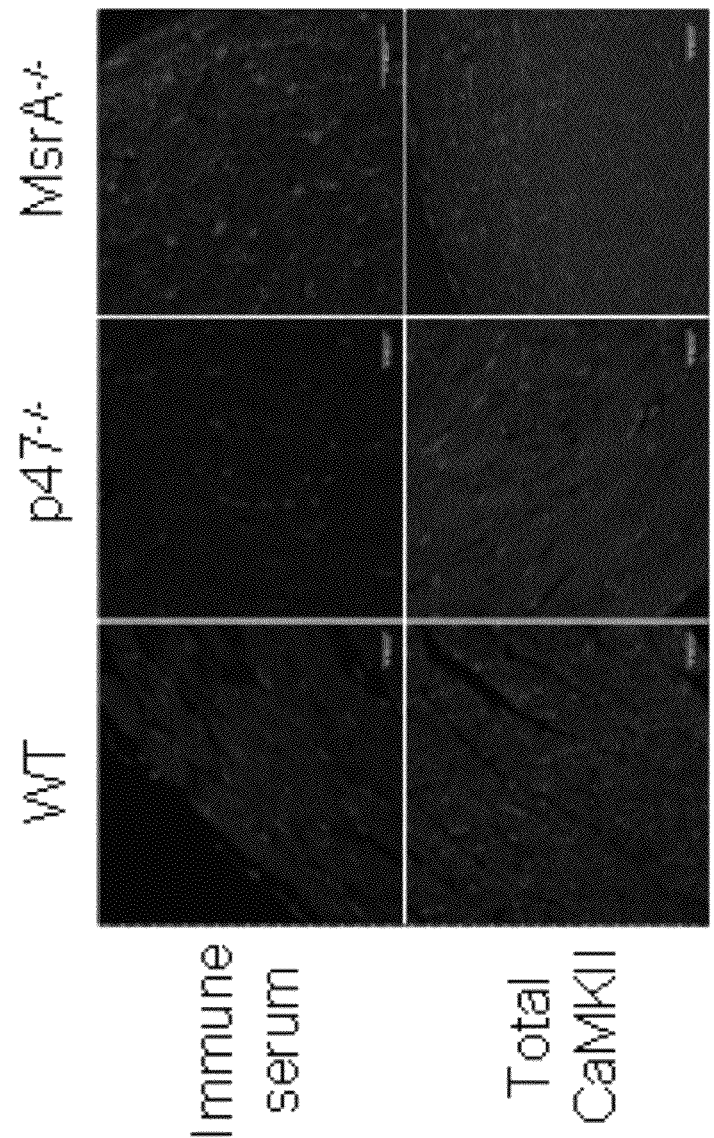
FIG. 11. Mice lacking MsrA have increased CaMKII oxidation, apoptosis, reduced survival and impaired heart function after myocardial infarction. (A) Immunostaining and (B) stain intensity quantification of oxidized CaMKII in heart sections from WT, $p47^{-/-}$, and $MsrA^{-/-}$ mice post-MI (n=3 hearts/group, * p<0.05 vs. WT). (C) Summary data for TUNEL staining of heart sections from WT, $p47^{-/-}$, and $MsrA^{-/-}$ mice post-MI (n=3 hearts/group, * p<0.05 vs. WT). (D) Mortality is significantly increased post-MI in $MsrA^{-/-}$ mice compared to WT controls. Numbers in bars represent post-MI deaths/total number of mice receiving MI. Post-MI left ventricular dilation (E) and function (F) were compromised in surviving $MsrA^{-/-}$ mice compared to WT controls three weeks after surgery (n=17 hearts/group for WT, n=9 hearts/group for $MsrA^{-/-}$).
Figure 11:
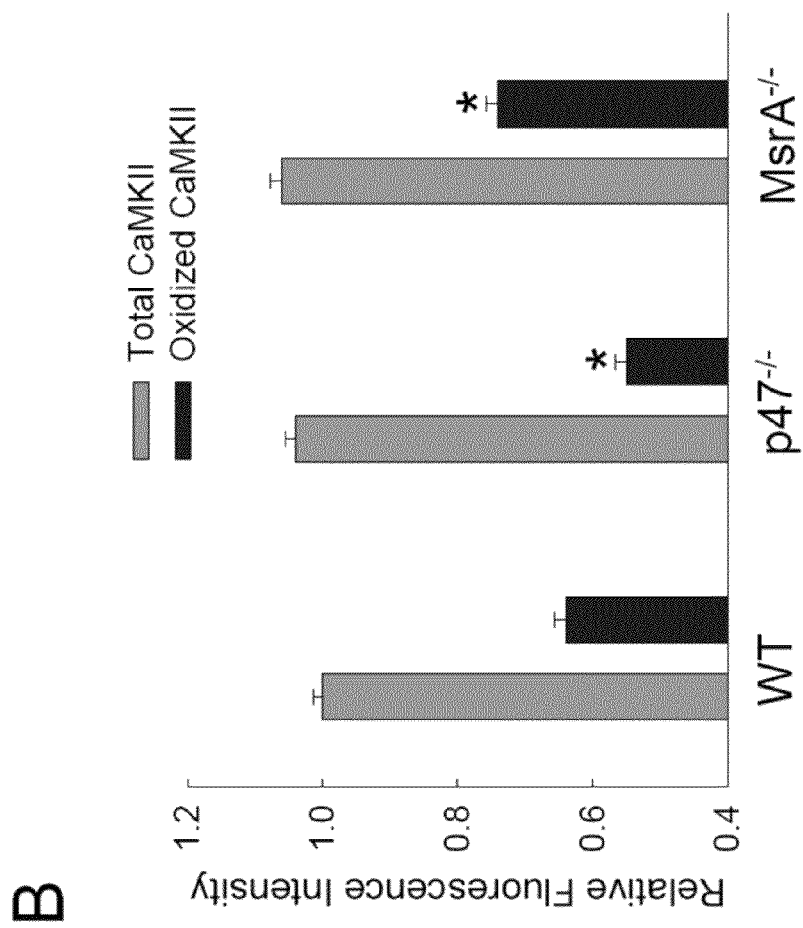
Figure 11:
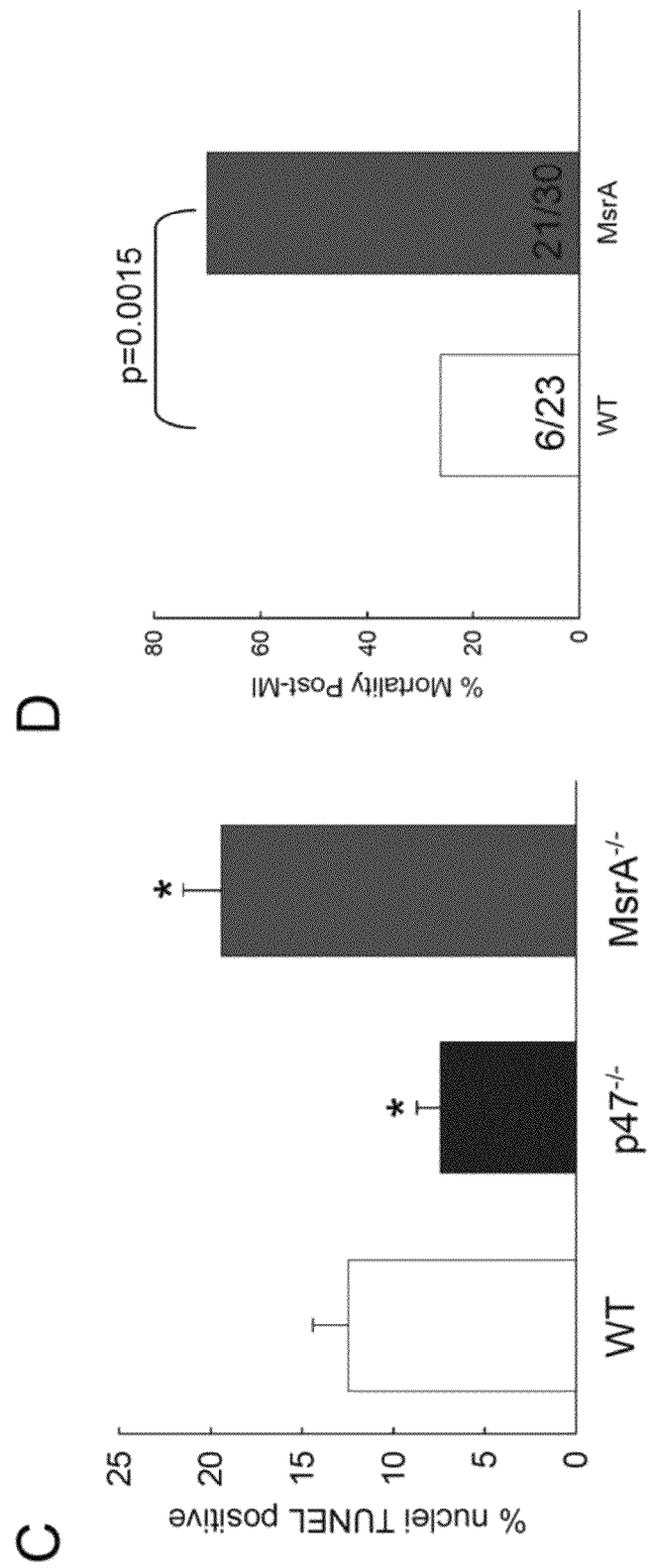
Figure 11:
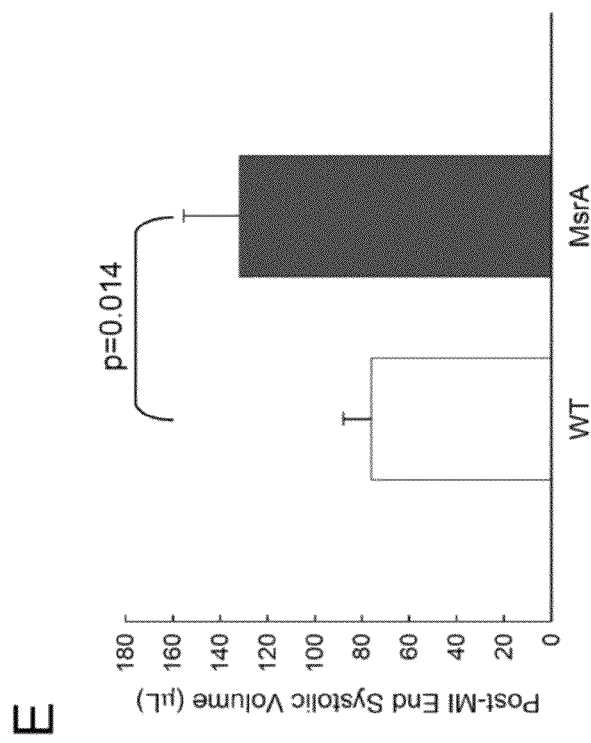

8. Increased CaMKII Oxidation, Apoptosis, Cardiac Dysfunction and Death in $MsrA^{-/-}$ Mice Methionine oxidation is specifically reversed by MsrA (Weissbach e.g., 2002), so it was hypothesized that $MsrA^{-/-}$ mice would show enhanced vulnerability to AngII-mediated CaMKII oxidation and apoptosis. In order to test this idea, $MsrA^{-/-}$ and WT control mice were implanted with AngII or saline eluting osmotic mini pumps. Hearts from $MsrA^{-/-}$ mice treated with AngII in vivo showed significantly more CaMKII oxidation (FIG. 10A,B) and increased TUNEL staining (FIG. 10C) compared to saline treated $MsrA^{-/-}$ mice and to saline or AngII treated control hearts. The increased CaMKII oxidation by AngII in $MsrA^{-/-}$ hearts showed that CaMKII oxidation is dynamically regulated by MsrA in myocardium in vivo, and suggested that $MsrA^{-/-}$ mice would be more vulnerable to severe myocardial stress due to increased methionine oxidation. Myocardial infarction is the most common cause of sudden cardiac death and heart failure in patients, and $p47^{-/-}$ (Doerries e.g., 2007) and AC3-I mice (Zhang e.g., 2005) are protected from left ventricular dilation and dysfunction after myocardial infarction surgery, suggesting that ROS activation of CaMKII may be important in myocardial infarction. In order to test if CaMKII oxidation and apoptosis were regulated by NADPH oxidase and MsrA in the setting of myocardial infarction, $MsrA^{-/-}$, $p47^{-/-}$, and WT mice were subjected to myocardial infarction surgery. $MsrA^{-/-}$ mice showed significantly more CaMKII oxidation (FIG. 11A,B) and myocardial apoptosis (FIG. 11C) compared to WT and $p47^{-/-}$ mice. These data indicate CaMKII oxidation is dynamically regulated by NADPH oxidase and MsrA in the setting of myocardial infarction. Myocardial infarction surgery was performed on a larger cohort of $MsrA^{-/-}$ and WT control mice to determine if increased CaMKII oxidation and apoptosis in $MsrA^{-/-}$ mice translated into poorer functional outcomes. $MsrA^{-/-}$ mice were significantly more likely to die after surgery compared to WT controls (FIG. 11D, p=0.0015) and exhibited significantly greater left ventricular dilation (FIG. 11E) and impaired systolic function (FIG. 11F) compared to controls, demonstrating that methionine oxidation increases the pathological impact of myocardial infarction in vivo.

E. Discussion

CaMKII was first identified by its dependence on $Ca^{2+}$/CaM for activation (Schulman and Greengard, 1978). Later it was recognized that autophosphorylation at T287 modified the enzyme so that activity persisted even in the absence of elevated $Ca^{2+}$/CaM (Saitoh and Schwartz, 1985; Lou e.g., 1986; Patton e.g., 1990). These findings unveil a new dimension to CaMKII signaling by showing that oxidation of M281/282 is a distinct molecular event, but with similar consequences to Thr287 autophosphorylation for sustaining $Ca^{2+}$/CaM independent activity. Oxidative activation likely is important in all known CaMKII isoforms, and relies upon paired, oxidation susceptible residues (MM in $\beta$, $\gamma$ and $\delta$). Because of the ability of CaMKII to transition between $Ca^{2+}$/CaM dependent and $Ca^{2+}$/CaM independent species, CaMKII is considered a 'memory molecule' for the history of intracellular $Ca^{2+}$ elevation. ROS facilitation of $Ca^{2+}$/CaM CaMKII activity suggests that the ability of CaMKII to respond to $Ca^{2+}$ elevation is enhanced in pro-oxidant conditions. Because increased CaMKII activity and oxidative stress are implicated in a wide variety of physiological and disease processes, these findings have potentially broad implications for improved understanding of connections between ROS and $Ca^{2+}$ in multiple cell types.

CaMKII is initially activated by $Ca^{2+}$/CaM binding, which blocks the autoinhibitory association between the regulatory and catalytic domains. Phosphorylation of T287 blocks the reassociation of the regulatory and catalytic domains, conferring $Ca^{2+}$/CaM independent activity on the enzyme (Hudmon and Schulman, 2002). In this study, a novel mechanism for CaMKII activation by oxidation of M281/282 was discovered. As is the case for T287-autophosphorylation, activating oxidation appears to require that the regulatory domain is first exposed by $Ca^{2+}$/CaM binding, whereupon oxidation at M281/282 leads to persistent $Ca^{2+}$/CaM-autonomous activation of CaMKII. Oxidation of methionine residues changes both the charge and flexibility of their side chains (Hoshi and Heinemann, 2001), apparently leading to steric blockage of reassociation between the regulatory and catalytic domains. Surprisingly, cysteine residues, a common target for oxidative regulation (Barford, 2004), do not appear to play any role in oxidative activation of CaMKII$\delta$ (or by inference CaMKII$\beta$ or $\gamma$). The regulatory domain of all CaMKII isoforms contains a single cysteine (C290 in CaMKII$\delta$), but oxidation of this unpaired cysteine is insufficient to activate CaMKII$\delta$. These data are aligned with the concept that $Ca^{2+}$/CaM-dependent exposure of the regulatory domain sets up the CaMKII molecule for subsequent modifications that confer persistent, $Ca^{2+}$ independent activity.

These findings identified a previously unrecognized mechanism of enhancing CaMKII by direct methionine oxidation, but oxidation may affect activity of kinases by multiple mechanisms. Pro-oxidant conditions can modify the activity levels of protein kinases by direct and indirect mechanisms. For example, direct thiol oxidation within the ATP binding pocket inhibits MEK kinase 1 activity (Cross and Templeton, 2004). Oxidative stress can induce activation of ERK1/2 (Engers e.g., 2006), while oxidation-dependent inactivation of protein phosphatases (Tonks, 2006) and upstream kinase kinases, such as IKK-β (Reynaert e.g., 2006) can indirectly lead to increased kinase activity. The present findings that AngII increases both CaMKII oxidation and autophosphorylation suggest that ROS inhibition of phosphatases further enhances CaMKII activity responses to oxidant stress in vivo.

Autophosphorylation at T287 is reversed by phosphatase activity (Zhabotinsky, 2000; Hudmon and Schulman, 2002). Because phosphorylation is a readily reversible process, activation by autophosphorylation represents a tunable regulatory mechanism for CaMKII. Oxidation of methionine residues is also a reversible biochemical modification, and the presence of methionine residues can confer functional sensitivity to oxidative stress (Santarelli e.g., 2006). Methionine sulfoxide reductase (Msr) reduces the side chain of methionine to its native state (Kryukov e.g., 2002), and is therefore a critical defense mechanism against cellular damage by oxidative stress. Mutant Drosophila overexpressing Msr had longer life spans, (Ruan e.g., 2002) while $MsrA^{-/-}$ mice show increased mortality in response to oxidant induced aging (Moskovitz e.g., 2001). The importance of MsrA in various biological systems suggests that reversible oxidation of methionine residues could complement a Thr287 phosphorylation/dephosphorylation cycle by serving as a ROS responsive regulatory mechanism for dynamically titering CaMKII activity. These studies show that MsrA is essential for reversing CaMKII oxidation in myocardium in vivo and that increased methionine oxidation worsens important clinical outcomes after myocardial infarction.

Structural heart disease is one of the largest public health problems in the developed world (Jessup and Brozena, 2003). AngII and PAR receptor antagonist drugs have significantly reduced mortality in patients with structural heart disease (Pfeffer e.g., 1992; Pfeffer e.g., 2003), and represent a remarkable success story for translating basic scientific understanding of cellular signaling into effective treatments for human disease. Increased cardiomyocyte apoptosis appears to be an important feature of advanced structural heart disease (Olivetti e.g., 1997). CaMKII is activated downstream to βAR receptor stimulation (Zhang e.g., 2005) by increased $Ca^{2+}$, (Zhu e.g., 2003). CaMKII inhibition reduces apoptosis (Zhu e.g., 2003; Yang e.g., 2006), and improves mortality (Khoo e.g., 2006) in structural heart disease models. These findings have contributed to a growing perception that CaMKII inhibition may be a novel therapeutic strategy for treating heart failure and arrhythmias (Bers, 2005). These data reveal the importance of M281/282 oxidation for CaMKII activation and thereby provide a new molecular mechanism for understanding the effects of AngII in cardiomyocytes and in structural heart disease. These present findings appear to increase the potential importance of CaMKII in structural heart disease by positioning CaMKII as a critical downstream nodal signal for enhancing cardiomyocyte death in response to excessive catecholamines, AngII and ROS. CaMKII has proven to be a remarkably versatile signaling molecule and the recently recognized role of ROS in activating CaMKII provides a new way of understanding the potential for oxidant stress to engage physiological and disease pathways in excitable cells.

F. References for Example I

1. Backs, J., Song, K., Bezprozvannaya, S., Chang, S., and Olson, E. N. (2006) CaM kinase II selectively signals to histone deacetylase 4 during cardiomyocyte hypertrophy. J. Clin. Invest 116, 1853-1864.
2. Barford, D. (2004) The role of cysteine residues as redox-sensitive regulatory switches. Curr. Opin. Struct. Biol. 14, 679-686.
3. Bernstein, E., Caudy, A. A., Hammond, S. M., and Hannon, G. J. (2001) Role for a bidentate ribonuclease in the initiation step of RNA interference. Nature 409, 363-366.
4. Bers, D. M. (2005) Beyond beta blockers. Nat. Med. 11, 379-380.
5. Brummelkamp, T. R., Bernards, R., and Agami, R. (2002) A system for stable expression of short interfering RNAs in mammalian cells. Science 296, 550-553.
6. Colbran, R. J. (1993) Inactivation of $Ca^{2+}$/calmodulin-dependent protein kinase H by basal autophosphorylation. J. Biol. Chem. 268, 7163-7170.
7. Cross, J. V. and Templeton, D. J. (2004) Oxidative stress inhibits MEKK1 by site-specific glutathionylation in the ATP-binding domain. Biochem. J. 381, 675-683.
8. Doenies, C., Grote, K., Hilfiker-Kleiner, D., Luchtefeld, M., Schaefer, A., Holland, S. M., Sorrentino, S., Manes, C., Schieffer, B., Drexler, H., and Landmesser, U. (2007) Critical role of the NAD(P)H oxidase subunit p47phox for left ventricular remodeling/dysfunction and survival after myocardial infarction. Circ. Res. 100, 894-903.
9. Engers, R., Springer, E., Kehren, V., Simic, T., Young, D. A., Beier, J., Klotz, L. O., Clark, I. M., Sies, H., and Gabbert, H. E. (2006) Rac upregulates tissue inhibitor of metalloproteinase-1 expression by redox-dependent activation of extracellular signal-regulated kinase signaling. FEBS J. 273, 4754-4769.
10. Grueter, C. E., Abiria, S. A., Dzhura, I., Wu, Y., Ham, A. J., Mohler, P. J., Anderson, M. E., and Colbran, R. J. (2006) L-Type $Ca^{2+}$ Channel Facilitation Mediated by Phosphorylation of the [beta] Subunit by CaMKII. Mol. Cell. 23, 641-650.
11. Hammond, S. M., Bernstein, E., Beach, D., and Hannon, G. J. (2000) An RNA-directed nuclease mediates post-transcriptional gene silencing in Drosophila cells. Nature 404, 293-296.
12. Hare, J. M. (2001) Oxidative stress and apoptosis in heart failure progression. Circ. Res. 89, 198-200.
13. Hoshi, T. and Heinemann, S. H. (2001) Regulation of cell function by methionine oxidation and reduction. J. Physiol. 531.1, 1-11.
14. Howe, C. J., Lahair, M. M., McCubrey, J. A., and Franklin, R. A. (2004) Redox regulation of the calcium/calmodulin-dependent protein kinases. J. Biol. Chem. 279, 44573-44581.
15. Hudmon, A. and Schulman, H. (2002) Structure-function of the multifunctional $Ca^{2+}$/calmodulin-dependent protein kinase II. Biochem. J. 364, 593-611.
16. Jessup, M. and Brozena, S. (2003) Heart failure. N. Engl. J. Med. 348, 2007-2018.
17. Khoo, M. S., Li, J., Singh, M. V., Yang, Y., Kannankeril, P., Wu, Y., Grueter, C. E., Guan, X., Oddis, C. V., Zhang, R., e.g. (2006) Death, cardiac dysfunction, and arrhythmias are increased by calmodulin kinase II in calcineurin cardiomyopathy. Circ. 114, 1352-1359.
18. Kinugawa, S., Tsutsui, H., Hayashidani, S., Ide, T., Suematsu, N., Satoh, S., Utsumi, H., and Takeshita, A. (2000) Treatment with dimethylthiourea prevents left ventricular remodeling and failure after experimental myocardial infarction in mice: role of oxidative stress. Circ. Res. 87, 392-398.
19. Kryukov, G. V., Kumar, R. A., Koc, A., Sun, Z., and Gladyshev, V. N. (2002) Selenoprotein R is a zinc-containing stereo-specific methionine sulfoxide reductase. Proc. Natl. Acad. Sci. 99, 4245-4250.
20. Liu, H., Sadygov, R. G., and Yates, J. R., III (2004) A model for random sampling and estimation of relative protein abundance in shotgun proteomics. Anal. Chem. 76, 4193-4201.
21. Lou, L. L., Lloyd, S. J., and Schulman, H. (1986) Activation of the multifunctional $Ca^{2+}$/calmodulin-dependent protein kinase by autophosphorylation: ATP modulates production of an autonomous enzyme. Proc. Nat. Acad. Sci. 83, 9497-9501. Lyle, A. N. and Griendling, K. K. (2006) Modulation of vascular smooth muscle signaling by reactive oxygen species. Physiology 21, 269-280.
22. Maack, C., Kartes, T., Kilter, H., Schafers, H. J., Nickenig, G., Bohm, M., and Laufs, U. (2003) Oxygen free radical release in human failing myocardium is associated with increased activity of rac1-GTPase and represents a target for statin treatment. Circ. 108, 1567-1574.
23. Meyer, T., Hanson, P. I., Stryer, L., and Schulman, H. (1992) Calmodulin trapping by calcium-calmodulin-dependent protein kinase. Science 256, 1199-1202.
24. Mohler, P. J., Le Scouarnec, S., Denjoy, I., Lowe, J. S., Guicheney, P., Caron, L., Driskell, I. M., Schott, J. J., Norris, K., Leenhardt, A., e.g. (2007) Defining the cellular phenotype of "ankyrin-B syndrome" variants: human ANK2 variants associated with clinical phenotypes display a spectrum of activities in cardiomyocytes. Circ. 115, 432-441.
25. Moskovitz, J., Bar-Noy, S., Williams, W. M., Requena, J., Berlett, B. S., and Stadtman, E. R. (2001) Methionine sulfoxide reductase (MsrA) is a regulator of antioxidant defense and lifespan in mammals. Proc. Natl. Acad. Sci. 98, 12920-12925.
26. Munzel, T. and Keaney, J. F., Jr. (2001) Are ACE inhibitors a "magic bullet" against oxidative stress? Circ. 104, 1571-1574.
27. Olivetti, G., Abbi, R., Quaini, F., Kajstura, J., Cheng, W., Nitahara, J. A., Quaini, E., Di, L. C., Beltrami, C. A., Krajewski, S., e.g. (1997) Apoptosis in the failing human heart. N. Engl. J. Med. 336, 1131-1141.
28. Patton, B. L., Miller, S. G., and Kennedy, M. B. (1990) Activation of type II calcium/calmodulin-dependent protein kinase by $Ca^{2+}$/calmodulin is inhibited by autophosphorylation of threonine within the calmodulin-binding domain. J. Biol. Chem. 265, 11204-11212.
29. Pfeffer, M. A., Braunwald, E., Moye, L. A., Basta, L., Brown, E. J., Jr., Cuddy, T. E., Davis, B. R., Geltman, E. M., Goldman, S., e.g. (1992) Effect of captopril on mortality and morbidity in patients with left ventricular dysfunction after myocardial infarction. Results of the survival and ventricular enlargement trial. The SAVE Investigators. N. Engl. J. Med. 327, 669-677.
30. Pfeffer, M. A., McMurray, J. J., Velazquez, E. J., Rouleau, J. L., Kober, L., Maggioni, A. P., Solomon, S. D., Swedberg, K., Van de, W. F., White, H., e.g. (2003) Valsartan, captopril, or both in myocardial infarction complicated by heart failure, left ventricular dysfunction, or both. N. Engl. J. Med. 349, 1893-1906.
31. Reynaert, N. L., van, D., V, Guala, A. S., McGovern, T., Hristova, M., Pantano, C., Heintz, N. H., Heim, J., Ho, Y. S., Matthews, D. E., Wouters, E. F., and Janssen-Heininger, Y. M. (2006) Dynamic redox control of NF-kappaB through glutaredoxin-regulated S-glutathionylation of inhibitory kappaB kinase beta. Proc. Natl. Acad. Sci. 103, 13086-13091.
32. Rosenberg, O. S., Deindl, S., Sung, R. J., Nairn, A. C., and Kuriyan, J. (2005) Structure of the autoinhibited kinase domain of CaMKII and SAXS analysis of the holoenzyme. Cell 123, 849-860.
33. Ruan, H., Tang, X. D., Chen, M. L., Joiner, M. L., Sun, G., Brot, N., Weissbach, H., Heinemann, S. H., Iverson, L., Wu, C. F., and Hoshi, T. (2002) High-quality life extension by the enzyme peptide methionine sulfoxide reductase. Proc. Natl. Acad. Sci. 99, 2748-2753.
34. Saitoh, T. and Schwartz, J. H. (1985) Phosphorylation-dependent subcellular translocation of a $Ca^{2+}$/calmodulin-dependent protein kinase produces an autonomous enzyme in Aplysia neurons. J. Cell Biol. 100, 835-842.
35. Santarelli, L. C., Wassef, R., Heinemann, S. H., and Hoshi, T. (2006) Three methionine residues located within the regulator of conductance for $K^+$ (RCK) domains confer oxidative sensitivity to large-conductance $Ca^{2+}$-activated $K^+$ channels. J. Physiol 571, 329-348.
36. Schulman, H. and Greengard, P. (1978) $Ca^{2+}$-dependent protein phosphorylation system in membranes from various tissues, and its activation by "calcium-dependent regulator". Proc. Nat. Acad. Sci. 75, 5432-5436.
37. Sharma, R. V., Chapleau, M. W., Hajduczok, G., Wachtel, R. E., Waite, L. J., Bhalla, R. C., and Abboud, F. M. (1995) Mechanical stimulation increases intracellular calcium concentration in nodose sensory neurons. Neuroscience 66, 433-441.
38. Tojo, A., Onozato, M. L., Kobayashi, N., Goto, A., Matsuoka, H., and Fujita, T. (2002) Angiotensin II and oxidative stress in Dahl Salt-sensitive rat with heart failure. Hypertension 40, 834-839.
39. Tonks, N. K. (2006) Protein tyrosine phosphatases: from genes, to function, to disease. Nat. Rev. Mol. Cell. Biol. 7, 833-846.
40. Weiss, R. M., Ohashi, M., Miller, J. D., Young, S. G., and Heistad, D. D. (2006) Calcific aortic valve stenosis in old hypercholesterolemic mice. Circ. 114, 2065-2069.
41. Weissbach, H., Etienne, F., Hoshi, T., Heinemann, S. H., Lowther, W. T., Matthews, B., St John, G., Nathan, C., and Brot, N. (2002) Peptide methionine sulfoxide reductase: structure, mechanism of action, and biological function. Arch. Biochem. Biophys. 397, 172-178.
42. Wu, Y., Temple, J., Zhang, R., Dzhura, I., Zhang, W., Trimble, R. W., Roden, D. M., Passier, R., Olson, E. N., Colbran, R. J., and Anderson, M. E. (2002) Calmodulin kinase II and arrhythmias in a mouse model of cardiac hypertrophy. Circ. 106, 1288-1293.
43. Yang, Y., Zhu, W. Z., Joiner, M. L., Zhang, R., Oddis, C. V., Hou, Y., Yang, J., Price, E. E., Gleaves, L., Eren, M., e.g. (2006) Calmodulin kinase II inhibition protects against myocardial cell apoptosis in vivo. Am. J. Physiol Heart Circ. Physiol 291, H3065-H3075.
44. Zangerle, L., Cuenod, M., Winterhalter, K. H., and Do, K. Q. (1992) Screening of thiol compounds: depolarization-induced release of glutathione and cysteine from rat brain slices. J. Neurochem. 59, 181-189.
45. Zhabotinsky, A. M. (2000) Bistability in the $Ca^{2+}$/calmodulin-dependent protein kinase-phosphatase system. Biophy J 79, 2211-2221.
46. Zhang, R., Khoo, M. S., Wu, Y., Yang, Y., Grueter, C. E., Ni, G., Price, E. E., Thiel, W., Guatimosim, S., Song, L. S., e.g. (2005) Calmodulin kinase II inhibition protects against structural heart disease. Nat. Med. 11, 409-417.
47. Zhu, W. Z., Wang, S. Q., Chakir, K., Yang, D. M., Zhang, T., Brown, J. H., Devic, E., Kobilka, B. K., Cheng, H. P., and Xiao, R. P. (2003) Linkage of beta(1)-adrenergic stimulation to apoptotic heart cell death through protein kinase A-independent activation of Ca²⁺/calmodulin kinase II. J. of Clin. Inv. 111, 617-625.
48. Zhu, W. Z., Woo, A. Y., Yang, D. M., Cheng, H., Crow, M. T., and Xiao, R. P. (2007) Activation of CaMKII is a common intermediate of diverse death stimuli-induced heart muscle cell apoptosis. J. of Biol. Chem. 282, 10833-10839.
49. Zimmerman, M. C., Dunlay, R. P., Lazartigues, E., Zhang, Y., Sharma, R. V., Engelhardt, J. F., and Davisson, R. L. (2004) Requirement for Rac1-dependent NADPH oxidase in the cardiovascular and dipsogenic actions of angiotensin II in the brain. Circ. Res. 95, 532-539.

Example II

Characterization of Antiserum Against oxCaMKII

Rabbit Antiserum Against Oxidized Calcium/Calmodulin Dependent Kinase II was prepared as described in Example I and tested as follows.

A. Immunodetection of Oxidized CaMKII in Heart Tissues

Figure 14:
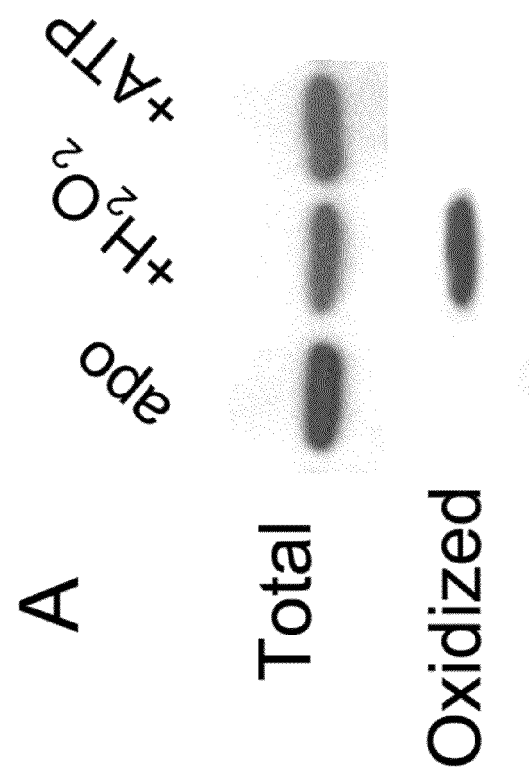
FIG. 14. A. Immunodetection of oxidized CaMKII (by $H_2O_2$) using antiserum (lower panel marked 'oxidized'). B. Immunodetection of oxidized CaMKII in heart in vivo after AngII infusion (right panel, red staining) compared to saline (left panel). Blue dapi staining indicates nuclei in both panels.
Figure 14:
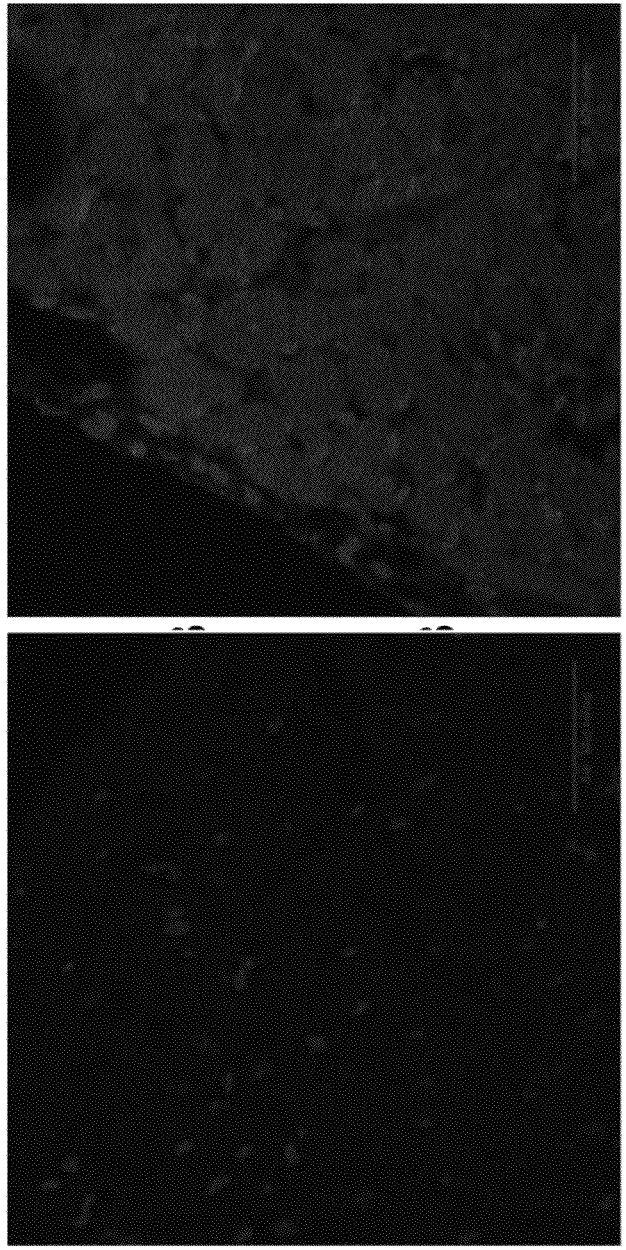

To test the specificity of this antiserum, Western blots of isolated CaMKII after no treatment, oxidation with $H_2O_2$, or phosphorylation with ATP were performed. CaMKII samples were probed for either total protein using a general CaMKII antibody or for oxidized CaMKII with anti-oxCaMKII antiserum. These results demonstrate the specificity of this antiserum for the oxidized form of CaMKII. (See FIG. 14A). To test the efficacy of the antiserum in tissue staining, mice were treated with either saline or angiotensin II, an oxidant stimulating agent in cardiac tissue, and stained heart sections and performed immunofluorescent stains for oxidized CaMKII. The heart treated with angiotensin II showed significant staining relative to the control. (See FIG. 14B).

Figure 15:
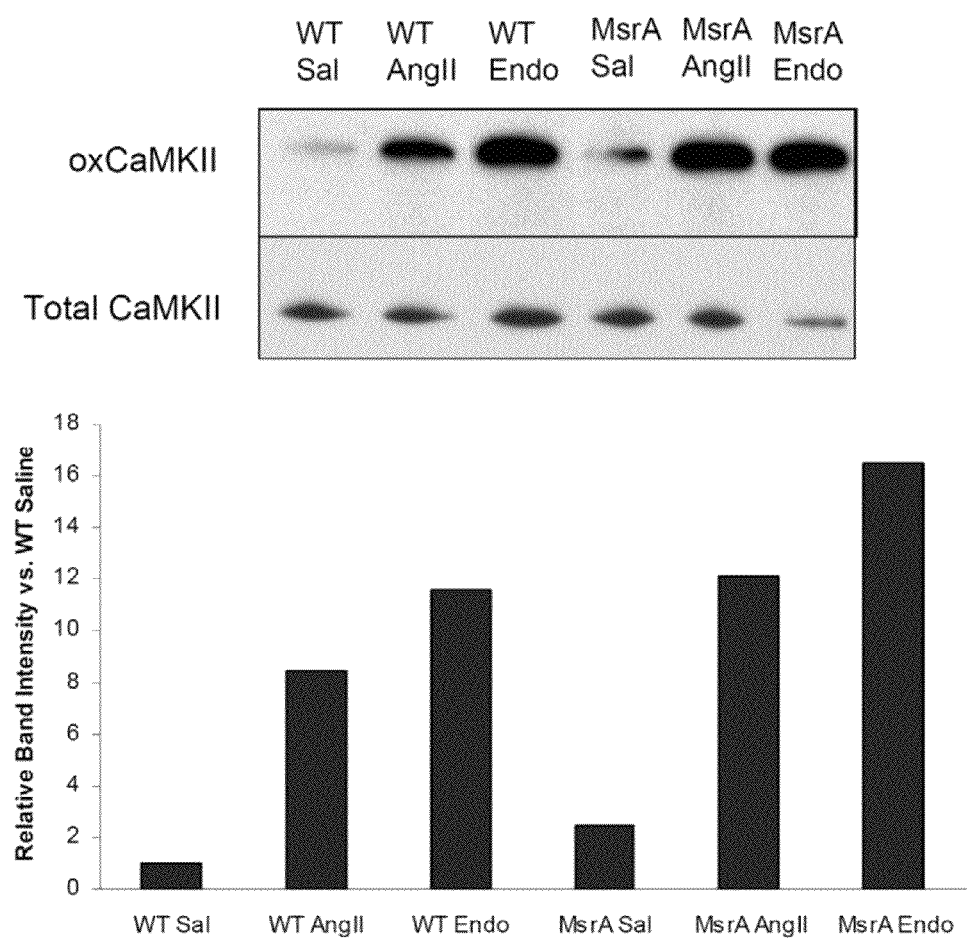
FIG. 15. Angiotensin II (AngII) and endotoxin (Endo) treatment results in increased oxidized CaMKII (oxCaMKII) in blood. Wild type (WT) and MsrA-/- mice were treated with saline, AngII, or Endo and sacrificed 6 hours later. The top (oxidized CaMKII) and bottom (total CaMKII) blots are of paired samples. From left to right: wild type mice treated with saline injection (lane 1); wild type mice treated with angiotensin II to mimic signaling in myocardial hypertrophy and heart failure (lane 2); wild type mice treated with bacterial endotoxin to mimic sepsis (lane 3); MsrA knock out mice—a model of premature aging—treated with saline (lane 4); MsrA knock out mice treated with angiotensin II—a model of heart disease as part of premature aging (lane 5); MsrA knock out mice treated with bacterial endotoxin—a model of sepsis in aging (lane 6). Western blot of blood samples and ImageJ analysis were used to quantify total and oxidized CaMKII. Summary data show the band intensity of oxCaMKII relative to WT treated with saline, normalized for total CaMKII present. N=1 for each group.

B. Angiotensin II (AngII) and Endotoxin (Endo) Treatment Results in Increased Oxidized CaMKII (oxCaMKII) in Blood In order to test whether the anti-oxCaMKII antiserum was suitable for detecting increased CaMKII oxidation in blood under disease conditions associated with enhanced oxidative stress, validated mouse models were utilized. Wild type (WT) and MsrA-/- mice were treated with saline, AngII, or Endo and sacrificed 6 hours later. (See FIG. 15). Western blot of blood samples and ImageJ analysis were used to quantify total and oxidized CaMKII. (See FIG. 15). Immunoblots of peripheral blood show increased oxidized CaMKII in heart failure, sepsis and premature aging disease models. (See FIG. 15).

Figure 16:
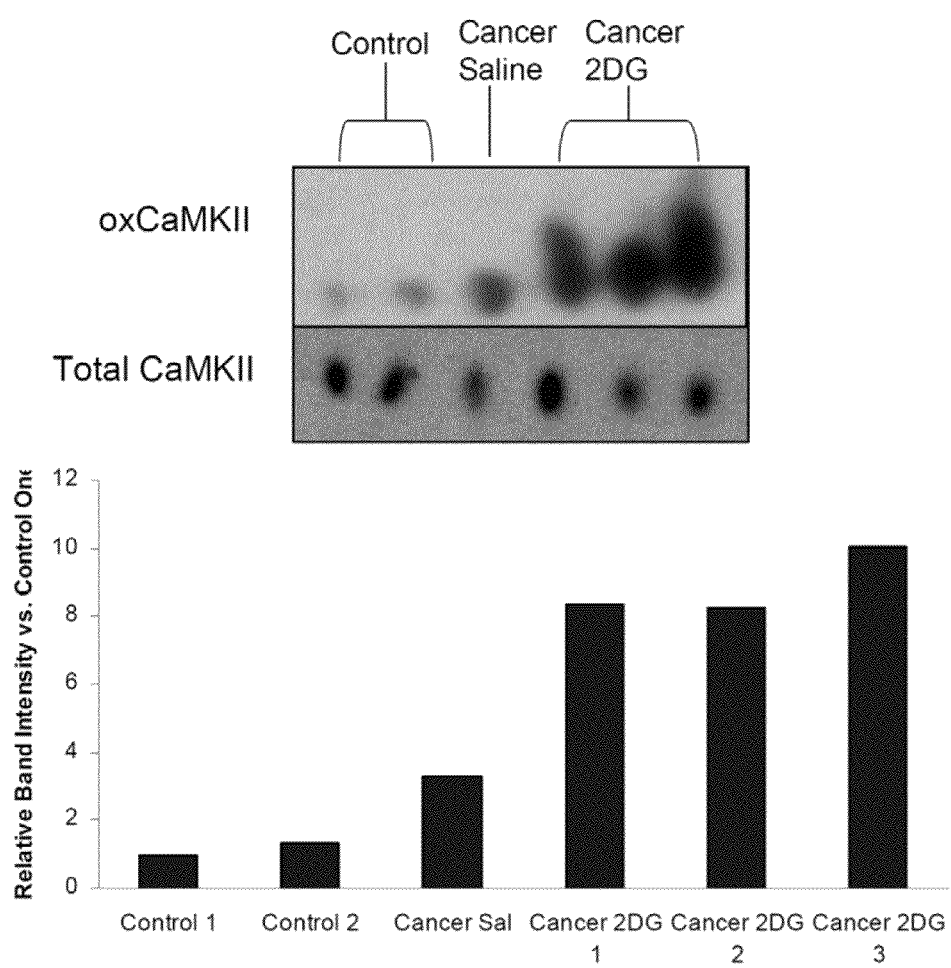
FIG. 16. Cancer and w-deoxyglucose (2DG) treatment are associated with concomitant increases in oxCaMKII in blood. Mice were exposed to cancer cells and treated with either saline or 2DG. Those mice that failed to develop tumors after 60 days were labeled as controls. The top (oxidized CaMKII) and bottom (total CaMKII) blots are of paired samples. From left to right: healthy control mice (lanes 1 and 2); increased oxidized CaMKII in a mouse with cancer (lane 3); mice with cancer treated with 2-deoxyglucose—an experimental cancer therapy—show markedly increased oxidized CaMKII (lanes 4 and 5). Western blot of blood samples and ImageJ analysis were used to quantify total and oxidized CaMKII. Summary data show the band intensity of oxCaMKII relative to Control 1, normalized for total CaMKII present. N=1 for each group.

C. Cancer and 2DG Treatment are Associated with Concomitant Increases in oxCaMKII in Blood Mice were exposed to cancer cells and treated with either saline or 2DG. Those mice that failed to develop tumors after 60 days were labeled as controls. (See FIG. 16). Western blot of blood samples and ImageJ analysis were used to quantify total and oxidized CaMKII. (See FIG. 16). Immunoblots of peripheral blood showed increased oxidized CaMKII in healthy mice and mice with cancer. (See FIG. 16).

D. Detection of oxCaMKII in Mice Bearing Cancer

Figure 17:
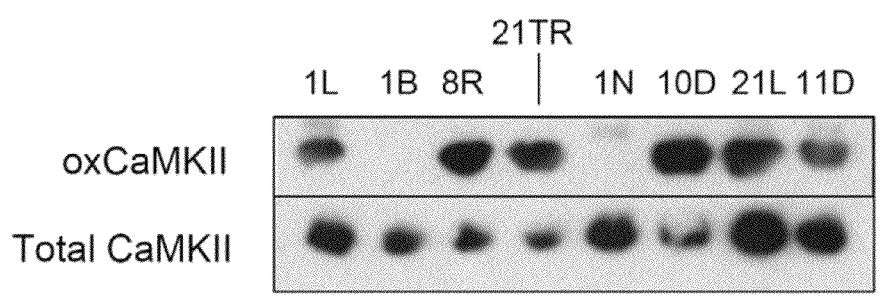
FIG. 17. A sample experiment to probe for the presence of oxCaMKII in mice bearing cancer and post-treatment. Mice with no cancer, FADU (head and neck cancer), or human lung cancer were treated with saline, 2DG, radiation (rad), or given a ketogenic diet (keto). The table indicates cancer type and treatment for each sample.

Mice with no cancer, FADU (head and neck cancer), or human lung cancer were treated with saline, 2DG, radiation (rad), or given a ketogenic diet (keto). Blood samples were collected from the mice and oxidized CaMKII and total CaMKII were measured by immunoassay. (See FIG. 17.)

E. Cancer and Varied Treatments Increase Blood oxCaMKII in an Additive Manner

Figure 18:
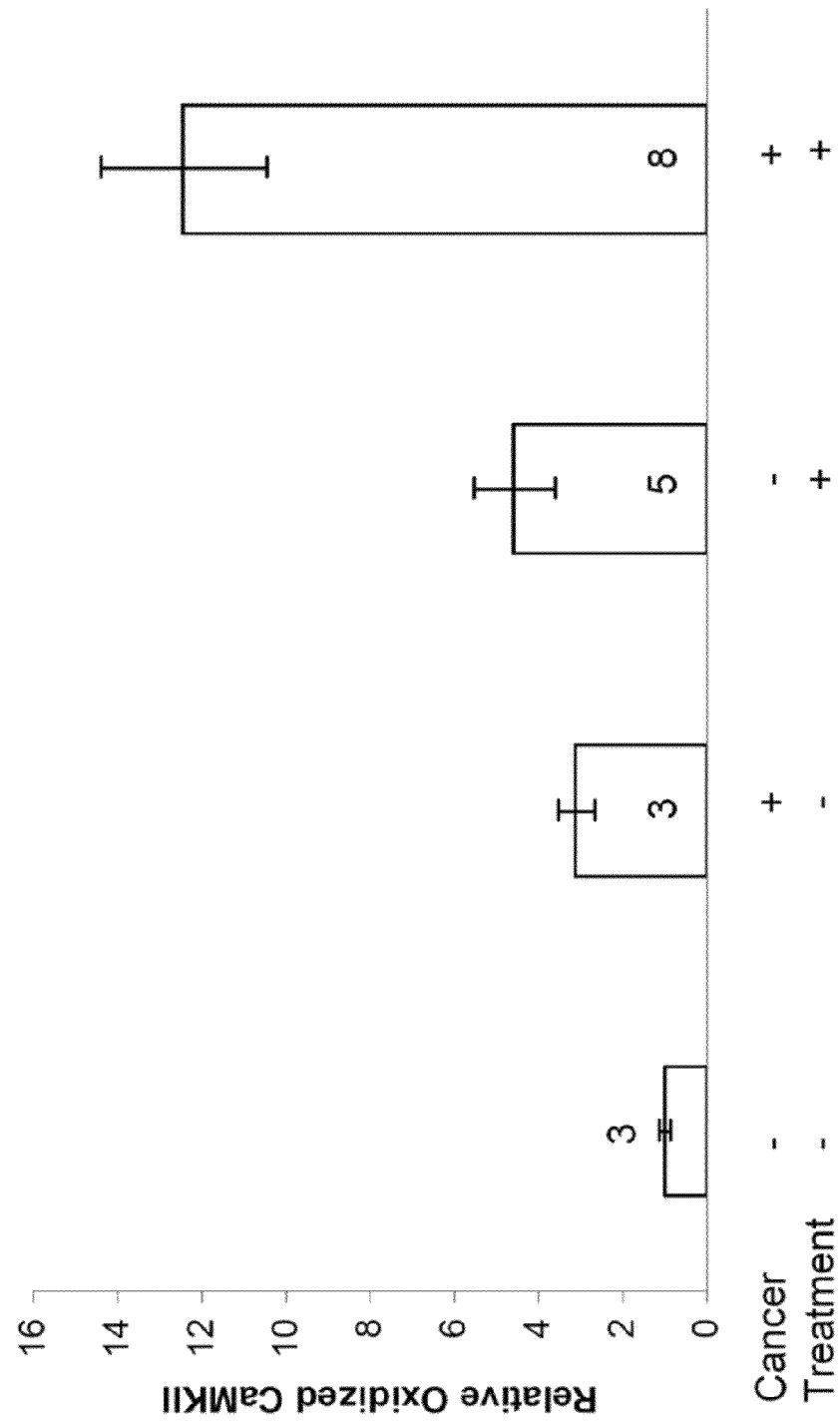
FIG. 18. Both cancer and varied treatments increase blood oxCaMKII in an additive manner. Mice were divided into four groups based on the presence or absence of cancer and whether or not they received treatment. Western blot of blood samples and ImageJ analysis were used to quantify total and oxidized CaMKII. Summary data show the mean band intensity of oxCaMKII relative to negative cancer/negative treatment, in all cases normalized for total CaMKII present. N values for each group are indicated. Error bars represent SEM.

Mice were divided into four groups based on the presence or absence of cancer and whether or not they received treatment. Western blot of blood samples and ImageJ analysis were used to quantify total and oxidized CaMKII. (See FIG. 18). Both cancer and varied treatments increase blood oxCaMKII in an additive manner.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member, any subgroup of members of the Markush group or other group, or the totality of members of the Markush group or other group.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A purified monoclonal antibody or antigen-binding fragment thereof that binds specifically to oxidized calcium/calmodulin-dependent protein kinase II (oxCaMKII), wherein the monoclonal antibody or antigen-binding fragment binds specifically to an oxidized peptide of CaMKII having the sequence of SEQ ID NO:5, and wherein the monoclonal antibody or antigen-binding fragment does not bind to a non-oxidized peptide of CaMKII having the sequence of SEQ ID NO:5.

2. A labeled monoclonal antibody or antigen-binding fragment thereof comprising the monoclonal antibody or antigen-binding fragment thereof according to claim 1 and a label.

3. A kit for detecting oxCaMKII, comprising:
   (a) a monoclonal antibody or antigen-binding fragment thereof that binds specifically to oxCaMKII to form a complex, wherein the monoclonal antibody or antigen-binding fragment binds specifically to an oxidized peptide of CaMKII having the sequence of SEQ ID NO:5, and wherein the monoclonal antibody or antigen-binding fragment does not bind to a non-oxidized peptide of CaMKII having the sequence of SEQ ID NO:5; and
   (b) a label for detecting the complex.

4. A pharmaceutical composition comprising:
   (a) a monoclonal antibody or antigen-binding fragment thereof that binds specifically to oxCaMKII, wherein the monoclonal antibody or antigen-binding fragment binds specifically to an oxidized peptide of CaMKII having the sequence of SEQ ID NO:5, and wherein the monoclonal antibody or antigen-binding fragment does not bind to a non-oxidized peptide of CaMKII having the sequence of SEQ ID NO:5; and
   (b) a pharmaceutically acceptable carrier.

5. The monoclonal antibody or antigen-binding fragment according to claim 1, wherein the antigen-binding fragment is selected from a group consisting of an Fab fragment, an F(ab')$_2$ fragment, a dAb fragment, and a single chain Fv (scFv).

6. The monoclonal antibody or antigen-binding fragment according to claim 1, wherein the antibody or antigen-binding fragment is humanized.

7. The labeled monoclonal antibody or antigen-binding fragment thereof of claim 2, wherein the label is selected from a group consisting of a radiolabel, a fluorophore, an enzyme, a colloidal metal, and a colored nanoparticle.

8. The monoclonal antibody or antigen-binding fragment according to claim 1, wherein the monoclonal antibody or antigen-binding fragment is immobilized on a solid support.

9. The kit according to claim 3, wherein the antigen-binding fragment is selected from a group consisting of an Fab fragment, an F(ab')$_2$ fragment, a dAb fragment, and a single chain Fv (scFv).

10. The kit according to claim 3, wherein the monoclonal antibody or antigen-binding fragment is humanized.

11. The kit according to claim 3, wherein the label is selected from a group consisting of a radiolabel, a fluorophore, an enzyme, a colloidal metal, and a colored nanoparticle.

12. The kit according to claim 3, wherein the monoclonal antibody or antigen-binding fragment is immobilized on a solid support.

13. The composition according to claim 4, wherein the antigen-binding fragment is selected from a group consisting of an Fab fragment, an F(ab')$_2$ fragment, a dAb fragment, and a single chain Fv (scFv).

14. The composition according to claim 4, wherein the monoclonal antibody or antigen-binding fragment is humanized.

* * * * *

SEQUENCE LISTING

<160> NUMBER OF SEQ ID NOS: 14

<210> SEQ ID NO 1
<211> LENGTH: 9
<212> TYPE: PRT
<213> ORGANISM: Artificial

```
<220> FEATURE:
<223> OTHER INFORMATION: Oligopeptide Corresponding to Amino Acid
      Sequence of Human CaMKII

<400> SEQUENCE: 1

Ser Thr Val Ala Ser Met Met His Arg
1               5

<210> SEQ ID NO 2
<211> LENGTH: 9
<212> TYPE: PRT
<213> ORGANISM: Artificial
<220> FEATURE:
<223> OTHER INFORMATION: Oligopeptide Corresponding to Consensus Amino
      Acid Sequence of Mammalian CaMKII
<220> FEATURE:
<221> NAME/KEY: Xaa
<222> LOCATION: (6)..(6)
<223> OTHER INFORMATION: "Xaa" is Cys or Met.

<400> SEQUENCE: 2

Ser Thr Val Ala Ser Xaa Met His Arg
1               5

<210> SEQ ID NO 3
<211> LENGTH: 10
<212> TYPE: PRT
<213> ORGANISM: Artificial
<220> FEATURE:
<223> OTHER INFORMATION: Oligopeptide Corresponding to Consensus Amino
      Acid Sequence of Mammalian CaMKII
<220> FEATURE:
<221> NAME/KEY: Xaa
<222> LOCATION: (5)..(5)
<223> OTHER INFORMATION: "Xaa" is Cys or Met.

<400> SEQUENCE: 3

Thr Val Ala Ser Xaa Met His Arg Gln Glu
1               5                   10

<210> SEQ ID NO 4
<211> LENGTH: 17
<212> TYPE: PRT
<213> ORGANISM: Artificial
<220> FEATURE:
<223> OTHER INFORMATION: Oligopeptide Corresponding to Consensus Amino
      Acid Sequence of Mammalian CaMKII
<220> FEATURE:
<221> NAME/KEY: Xaa
<222> LOCATION: (1)..(1)
<223> OTHER INFORMATION: "Xaa" in position #1 is Ser or Cys.
<220> FEATURE:
<221> NAME/KEY: Xaa
<222> LOCATION: (2)..(2)
<223> OTHER INFORMATION: "Xaa" in position #2 is His or Gln.
<220> FEATURE:
<221> NAME/KEY: Xaa
<222> LOCATION: (9)..(9)
<223> OTHER INFORMATION: "Xaa" in position #9 is Cys or Met.
<220> FEATURE:
<221> NAME/KEY: Xaa
<222> LOCATION: (17)..(17)
<223> OTHER INFORMATION: "Xaa" in position #17 is Asp or Glu.

<400> SEQUENCE: 4

Xaa Xaa Arg Ser Thr Val Ala Ser Xaa Met His Arg Gln Glu Thr Val
1               5                   10                  15

Xaa
```

```
<210> SEQ ID NO 5
<211> LENGTH: 17
<212> TYPE: PRT
<213> ORGANISM: Artificial
<220> FEATURE:
<223> OTHER INFORMATION: Oligopeptide Corresponding to Amino Acid
      Sequence of Human CaMKII

<400> SEQUENCE: 5

Cys Gln Arg Ser Thr Val Ala Ser Met Met His Arg Gln Glu Thr Val
1               5                   10                  15

Asp

<210> SEQ ID NO 6
<211> LENGTH: 19
<212> TYPE: RNA
<213> ORGANISM: Artificial
<220> FEATURE:
<223> OTHER INFORMATION: Oligonucleotide Targeting Human CaMKII

<400> SEQUENCE: 6
cuaugcuggc uacgagaaa                                                      19

<210> SEQ ID NO 7
<211> LENGTH: 12
<212> TYPE: DNA
<213> ORGANISM: Artificial
<220> FEATURE:
<223> OTHER INFORMATION: Oligonucleotide Targeting Human CaMKII
<220> FEATURE:
<221> NAME/KEY: r
<222> LOCATION: (1)..(12)
<223> OTHER INFORMATION: "r" is "a" or "g".
<220> FEATURE:
<221> NAME/KEY: y
<222> LOCATION: (1)..(12)
<223> OTHER INFORMATION: "y" is "c" or "t".

<400> SEQUENCE: 7
ctrgcyacra gr                                                             12

<210> SEQ ID NO 8
<211> LENGTH: 9
<212> TYPE: PRT
<213> ORGANISM: Artificial
<220> FEATURE:
<223> OTHER INFORMATION: Oligopeptide Corresponding to Amino Acid
      Sequence of Human CaMKII

<400> SEQUENCE: 8

Ala Val Ala Gly Lys Ala Gly Ala Arg
1               5

<210> SEQ ID NO 9
<211> LENGTH: 9
<212> TYPE: PRT
<213> ORGANISM: Artificial
<220> FEATURE:
<223> OTHER INFORMATION: Oligopeptide Corresponding to Amino Acid
      Sequence of Human CaMKII

<400> SEQUENCE: 9

Leu Leu Lys His Pro Asn Ile Val Arg
1               5
```

```
<210> SEQ ID NO 10
<211> LENGTH: 7
<212> TYPE: PRT
<213> ORGANISM: Artificial
<220> FEATURE:
<223> OTHER INFORMATION: Oligopeptide Corresponding to Amino Acid
      Sequence of Human CaMKII

<400> SEQUENCE: 10

Gly Ala Phe Ser Val Val Arg
1               5

<210> SEQ ID NO 11
<211> LENGTH: 10
<212> TYPE: PRT
<213> ORGANISM: Artificial
<220> FEATURE:
<223> OTHER INFORMATION: Oligopeptide Corresponding to Amino Acid
      Sequence of Human CaMKII

<400> SEQUENCE: 11

Ile Pro Thr Gly Gln Glu Tyr Ala Ala Lys
1               5                   10

<210> SEQ ID NO 12
<211> LENGTH: 499
<212> TYPE: PRT
<213> ORGANISM: Homo Sapiens

<400> SEQUENCE: 12

Met Ala Ser Thr Thr Thr Cys Thr Arg Phe Thr Asp Glu Tyr Gln Leu
1               5                   10                  15

Phe Glu Glu Leu Gly Lys Gly Ala Phe Ser Val Val Arg Arg Cys Met
                20                  25                  30

Lys Ile Pro Thr Gly Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
                100                 105                 110

Ala Ser His Cys Ile Gln Gln Ile Leu Glu Ser Val Asn His Cys His
            115                 120                 125

Leu Asn Gly Ile Val His Arg Asp Leu Lys Pro Glu Asn Leu Leu Leu
        130                 135                 140

Ala Ser Lys Ser Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Met Trp Ala Cys Gly Val Ile Leu Tyr Ile Leu Leu
        195                 200                 205

Val Gly Tyr Pro Pro Phe Trp Asp Glu Asp Gln His Arg Leu Tyr Gln
    210                 215                 220

Gln Ile Lys Ala Gly Ala Tyr Asp Phe Pro Ser Pro Glu Trp Asp Thr
225                 230                 235                 240
```

```
Val Thr Pro Glu Ala Lys Asp Leu Ile Asn Lys Met Leu Thr Ile Asn
            245                 250                 255

Pro Ala Lys Arg Ile Thr Ala Ser Glu Ala Leu Lys His Pro Trp Ile
        260                 265                 270

Cys Gln Arg Ser Thr Val Ala Ser Met Met His Arg Gln Glu Thr Val
    275                 280                 285

Asp Cys Leu Lys Lys Phe Asn Ala Arg Arg Lys Leu Lys Gly Ala Ile
290                 295                 300

Leu Thr Thr Met Leu Ala Thr Arg Asn Phe Ser Ala Ala Lys Ser Leu
305                 310                 315                 320

Leu Lys Lys Pro Asp Gly Val Lys Glu Ser Thr Glu Ser Ser Asn Thr
                325                 330                 335

Thr Ile Glu Asp Glu Asp Val Lys Ala Arg Lys Gln Glu Ile Ile Lys
        340                 345                 350

Val Thr Glu Gln Leu Ile Glu Ala Ile Asn Asn Gly Asp Phe Glu Ala
    355                 360                 365

Tyr Thr Lys Ile Cys Asp Pro Gly Leu Thr Ala Phe Glu Pro Glu Ala
370                 375                 380

Leu Gly Asn Leu Val Glu Gly Met Asp Phe His Arg Phe Tyr Phe Glu
385                 390                 395                 400

Asn Ala Leu Ser Lys Ser Asn Lys Pro Ile His Thr Ile Ile Leu Asn
                405                 410                 415

Pro His Val His Leu Val Gly Asp Asp Ala Ala Cys Ile Ala Tyr Ile
        420                 425                 430

Arg Leu Thr Gln Tyr Met Asp Gly Ser Gly Met Pro Lys Thr Met Gln
    435                 440                 445

Ser Glu Glu Thr Arg Val Trp His Arg Arg Asp Gly Lys Trp Gln Asn
450                 455                 460

Val His Phe His Arg Ser Gly Ser Pro Thr Val Pro Ile Lys Pro Pro
465                 470                 475                 480

Cys Ile Pro Asn Gly Lys Glu Asn Phe Ser Gly Gly Thr Ser Leu Trp
                485                 490                 495

Gln Asn Ile
```

<210> SEQ ID NO 13
<211> LENGTH: 499
<212> TYPE: PRT
<213> ORGANISM: Artificial
<220> FEATURE:
<223> OTHER INFORMATION: Mutant Form of Human CaMKII Having MetMet -->
      ValVal substitutions at positions 281/282

<400> SEQUENCE: 13

```
Met Ala Ser Thr Thr Thr Cys Thr Arg Phe Thr Asp Glu Tyr Gln Leu
1               5                   10                  15

Phe Glu Glu Leu Gly Lys Gly Ala Phe Ser Val Val Arg Arg Cys Met
                20                  25                  30

Lys Ile Pro Thr Gly Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95
```

-continued

Glu Leu Phe Glu Asp Ile Val Ala Arg Glu Tyr Tyr Ser Glu Ala Asp
                100                 105                 110

Ala Ser His Cys Ile Gln Gln Ile Leu Glu Ser Val Asn His Cys His
        115                 120                 125

Leu Asn Gly Ile Val His Arg Asp Leu Lys Pro Glu Asn Leu Leu Leu
    130                 135                 140

Ala Ser Lys Ser Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Met Trp Ala Cys Gly Val Ile Leu Tyr Ile Leu Leu
        195                 200                 205

Val Gly Tyr Pro Pro Phe Trp Asp Glu Asp Gln His Arg Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asp Leu Ile Asn Lys Met Leu Thr Ile Asn
                245                 250                 255

Pro Ala Lys Arg Ile Thr Ala Ser Glu Ala Leu Lys His Pro Trp Ile
            260                 265                 270

Cys Gln Arg Ser Thr Val Ala Ser Val Val His Arg Gln Glu Thr Val
        275                 280                 285

Asp Cys Leu Lys Lys Phe Asn Ala Arg Arg Lys Leu Lys Gly Ala Ile
    290                 295                 300

Leu Thr Thr Met Leu Ala Thr Arg Asn Phe Ser Ala Ala Lys Ser Leu
305                 310                 315                 320

Leu Lys Lys Pro Asp Gly Val Lys Glu Ser Thr Glu Ser Ser Asn Thr
                325                 330                 335

Thr Ile Glu Asp Glu Asp Val Lys Ala Arg Lys Gln Glu Ile Ile Lys
            340                 345                 350

Val Thr Glu Gln Leu Ile Glu Ala Ile Asn Asn Gly Asp Phe Glu Ala
        355                 360                 365

Tyr Thr Lys Ile Cys Asp Pro Gly Leu Thr Ala Phe Glu Pro Glu Ala
    370                 375                 380

Leu Gly Asn Leu Val Glu Gly Met Asp Phe His Arg Phe Tyr Phe Glu
385                 390                 395                 400

Asn Ala Leu Ser Lys Ser Asn Lys Pro Ile His Thr Ile Ile Leu Asn
                405                 410                 415

Pro His Val His Leu Val Gly Asp Asp Ala Ala Cys Ile Ala Tyr Ile
            420                 425                 430

Arg Leu Thr Gln Tyr Met Asp Gly Ser Gly Met Pro Lys Thr Met Gln
        435                 440                 445

Ser Glu Glu Thr Arg Val Trp His Arg Arg Asp Gly Lys Trp Gln Asn
    450                 455                 460

Val His Phe His Arg Ser Gly Ser Pro Thr Val Pro Ile Lys Pro Pro
465                 470                 475                 480

Cys Ile Pro Asn Gly Lys Glu Asn Phe Ser Gly Gly Thr Ser Leu Trp
                485                 490                 495

Gln Asn Ile

-continued

```
<210> SEQ ID NO 14
<211> LENGTH: 39
<212> TYPE: PRT
<213> ORGANISM: Artificial
<220> FEATURE:
<223> OTHER INFORMATION: Mutant Polypeptide Fragment of Human CaMKII

<400> SEQUENCE: 14

His Arg Ser Thr Val Ala Ser Met Met His Arg Gln Glu Thr Val Asp
1               5                   10                  15

Cys Leu Lys Lys Phe Asn Ala Arg Arg Lys Leu Lys Gly Ala Ile Leu
            20                  25                  30

Thr Thr Met Leu Ala Thr Arg
        35
```